United States Patent
Chang et al.

(10) Patent No.: US 9,751,948 B2
(45) Date of Patent: *Sep. 5, 2017

(54) CLASS OF MONOSPECIFIC AND BISPECIFIC HUMANIZED ANTIBODIES THAT TARGET THE INSULIN-LIKE GROWTH FACTOR TYPE I RECEPTOR (IGF-1R)

(71) Applicant: Immunomedics, Inc., Morris Plains, NJ (US)

(72) Inventors: Chien-Hsing Chang, Downingtown, PA (US); Michele J. Losman, South Orange, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/224,882

(22) Filed: Aug. 1, 2016

(65) Prior Publication Data
US 2016/0333098 A1  Nov. 17, 2016

Related U.S. Application Data

(60) Division of application No. 14/598,664, filed on Jan. 16, 2015, now Pat. No. 9,441,043, which is a (Continued)

(51) Int. Cl.
| | |
|---|---|
| *C07K 16/28* | (2006.01) |
| *A61K 39/395* | (2006.01) |
| *A61K 31/7068* | (2006.01) |
| *A61K 47/48* | (2006.01) |
| *A61K 51/10* | (2006.01) |
| *G01N 33/574* | (2006.01) |
| *A61K 45/06* | (2006.01) |
| *A61K 31/69* | (2006.01) |
| *C07K 16/30* | (2006.01) |
| *C07K 14/705* | (2006.01) |

(Continued)

(52) U.S. Cl.
CPC .......... *C07K 16/2863* (2013.01); *A61K 31/69* (2013.01); *A61K 31/7068* (2013.01); *A61K 39/3955* (2013.01); *A61K 39/39558* (2013.01); *A61K 45/06* (2013.01); *A61K 47/48561* (2013.01); *A61K 47/48569* (2013.01); *A61K 51/103* (2013.01); *A61K 51/1057* (2013.01); *A61K 51/1063* (2013.01); *A61K 51/1093* (2013.01); *C07K 16/30* (2013.01); *C07K 16/303* (2013.01); *C07K 16/3015* (2013.01); *C07K 16/3046* (2013.01); *C07K 16/3069* (2013.01); *G01N 33/57484* (2013.01); *A61K 2039/505* (2013.01); *C07K 14/475* (2013.01); *C07K 14/705* (2013.01); *C07K 16/28* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/522* (2013.01); *C07K 2317/53* (2013.01); *C07K 2317/55* (2013.01); *C07K 2317/56* (2013.01); *C07K 2317/565* (2013.01); *C07K 2317/64* (2013.01); *C07K 2317/76* (2013.01); *C07K 2319/735* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 4,046,722 A | 9/1977 | Rowland | |
| 4,699,784 A | 10/1987 | Shih et al. | |
| 4,868,109 A | 9/1989 | Lansdorp et al. | |
| 5,770,198 A | 6/1998 | Coller et al. | |
| 6,261,537 B1 | 7/2001 | Klaveness et al. | |
| 6,306,393 B1 | 10/2001 | Goldenberg et al. | |
| 6,310,185 B1 | 10/2001 | Wallace et al. | |
| 6,524,854 B1 | 2/2003 | Monia et al. | |
| 7,060,506 B2 | 6/2006 | Craig | |
| 7,521,056 B2 * | 4/2009 | Chang .................. | A61K 39/395 424/134.1 |
| 7,527,787 B2 * | 5/2009 | Chang .............. | A61K 47/48746 424/133.1 |
| 7,534,866 B2 | 5/2009 | Chang et al. | |

(Continued)

FOREIGN PATENT DOCUMENTS

| | | |
|---|---|---|
| WO | 00/68248 | 11/2000 |
| WO | 2006/069202 | 6/2006 |

(Continued)

OTHER PUBLICATIONS

Arteaga et al., "Blockade of the type I somatomedin receptor inhibits growth of human breast cancer cells in athymic mice", J. Clin. Invest. Nov. 1989;84(5):1418-23.

(Continued)

*Primary Examiner* — Zachary Howard
(74) *Attorney, Agent, or Firm* — Richard A. Nakashima

(57) ABSTRACT

The present invention provides compositions and methods of use of anti-IGF-1R antibodies or antibody fragments. Preferably the antibodies bind to IGF-1R but not IR; are not agonists for IGF-1R; do not block binding of IGF-1 or IGF-2 to isolated IGF-1R, but effectively neutralize activation of IGF-1R by IGF-1 in intact cells; and block binding of an R1 antibody to IGF-1R. The antibodies may be murine, chimeric, humanized or human R1 antibodies comprising the heavy chain CDR sequences DYYMY (SEQ ID NO:1), YITNYGGSTYYPDTVKG (SEQ ID NO:2) and QSNYDY-DGWFAY (SEQ ID NO:3) and the light chain CDR sequences KASQEVGTAVA (SEQ ID NO:4), WASTRHT (SEQ ID NO:5) and QQYSNYPLT (SEQ ID NO:6). Preferably the antibodies bind to an epitope of IGF-1R comprising the first half of the cysteine-rich domain of IGF-1R (residues 151-222). The anti-IGF-1R antibodies may be used for diagnosis or therapy of various diseases such as cancer.

20 Claims, 25 Drawing Sheets

Related U.S. Application Data continuation of application No. 14/061,176, filed on Oct. 23, 2013, now abandoned, which is a division of application No. 12/722,645, filed on Mar. 12, 2010, now abandoned, which is a continuation-in-part of application No. 12/689,336, filed on Jan. 19, 2010, now abandoned, said application No. 14/598,664 is a continuation-in-part of application No. 14/505,595, filed on Oct. 3, 2014, which is a division of application No. 13/688,812, filed on Nov. 29, 2012, now Pat. No. 8,883,162, and a continuation-in-part of application No. 13/483,761, filed on May 30, 2012, now abandoned, which is a division of application No. 12/949,536, filed on Nov. 18, 2010, now Pat. No. 8,211,440, which is a division of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. PCT/US2006/010762, filed on Mar. 24, 2006, and a continuation-in-part of application No. PCT/US2006/012084, filed on Mar. 29, 2006, and a continuation-in-part of application No. PCT/US2006/025499, filed on Jun. 29, 2006, and a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866.

(60) Provisional application No. 60/751,196, filed on Dec. 16, 2005, provisional application No. 60/864,530, filed on Nov. 6, 2006, provisional application No. 61/145,896, filed on Jan. 20, 2009, provisional application No. 61/566,273, filed on Dec. 2, 2011, provisional application No. 61/616,051, filed on Mar. 27, 2012.

(51) Int. Cl.
  *C07K 14/475* (2006.01)
  *A61P 35/00* (2006.01)
  *A61K 39/00* (2006.01)

(56) References Cited

U.S. PATENT DOCUMENTS

| | | |
|---|---|---|
| 7,550,143 B2 | 6/2009 | Chang et al. |
| 7,666,400 B2 | 2/2010 | Chang et al. |
| 7,816,333 B2 | 10/2010 | Kaneco et al. |
| 7,858,070 B2 | 12/2010 | Chang et al. |
| 7,871,622 B2 | 1/2011 | Chang et al. |
| 7,901,680 B2 | 3/2011 | Chang et al. |
| 7,906,118 B2 | 3/2011 | Chang et al. |
| 7,906,121 B2 | 3/2011 | Chang et al. |
| 7,981,398 B2 | 7/2011 | Chang et al. |
| 8,003,111 B2 | 8/2011 | Chang et al. |
| 8,034,352 B2 | 10/2011 | Chang et al. |
| 8,080,250 B1 | 12/2011 | Govindan et al. |
| 8,119,101 B2 | 2/2012 | Byrd et al. |
| 8,158,129 B2 | 4/2012 | Chang et al. |
| 8,163,291 B2 | 4/2012 | Chang et al. |
| 8,202,509 B2 | 6/2012 | McBride et al. |
| 8,211,440 B2 | 7/2012 | Chang et al. |
| 8,246,960 B2 | 8/2012 | Chang et al. |
| 8,277,817 B2 | 10/2012 | Chang et al. |
| 8,282,934 B2 | 10/2012 | Chang et al. |
| 8,287,865 B2 | 10/2012 | Hansen et al. |
| 8,349,332 B2 | 1/2013 | Chang et al. |
| 8,435,540 B2 | 5/2013 | Chang et al. |
| 8,444,956 B2 | 5/2013 | McBride et al. |
| 8,475,794 B2 | 7/2013 | Chang et al. |
| 8,481,041 B2 | 7/2013 | Chang et al. |
| 8,491,914 B2 | 7/2013 | Chang et al. |
| 8,551,480 B2 | 10/2013 | Chang et al. |
| 8,562,988 B2 | 10/2013 | Chang et al. |
| 8,591,892 B2 | 11/2013 | Alinari et al. |
| 8,597,659 B2 | 12/2013 | Chang et al. |
| 8,709,382 B2 | 4/2014 | D'Souza et al. |
| 8,758,726 B2 | 6/2014 | D'Souza et al. |
| 8,821,868 B2 | 9/2014 | Goldenberg et al. |
| 8,846,002 B2 | 9/2014 | Byrd et al. |
| 8,877,202 B2 | 11/2014 | Govindan et al. |
| 8,883,162 B2 | 11/2014 | Chang et al. |
| 8,945,554 B2 | 2/2015 | Hansen et al. |
| 8,986,669 B2 | 3/2015 | Huval et al. |
| 8,986,699 B2 | 3/2015 | Hansen et al. |
| 8,999,344 B2 | 4/2015 | Govindan et al. |
| 9,005,613 B2 | 4/2015 | Liu et al. |
| 9,089,618 B2 | 7/2015 | Gold et al. |
| 9,441,043 B2 * | 9/2016 | Chang ............... A61K 31/7068 |
| 2003/0133932 A1 | 7/2003 | Zhou et al. |
| 2003/0198956 A1 | 10/2003 | Makowski et al. |
| 2003/0232420 A1 | 12/2003 | Braun et al. |
| 2004/0018587 A1 | 1/2004 | Makowski et al. |
| 2004/0126361 A1 | 7/2004 | Saifer et al. |
| 2005/0003403 A1 | 1/2005 | Rossi et al. |
| 2005/0048050 A1 | 3/2005 | Fujita-Yamaguchi |
| 2005/0208585 A1 | 9/2005 | Adams et al. |
| 2006/0030015 A1 | 2/2006 | Uda et al. |
| 2006/0210475 A1 | 9/2006 | Goldenberg et al. |
| 2006/0228300 A1 | 10/2006 | Chang et al. |
| 2007/0072797 A1 | 3/2007 | Robinson et al. |
| 2007/0140966 A1 | 6/2007 | Chang et al. |
| 2007/0264265 A1 | 11/2007 | Goldenberg et al. |
| 2008/0233118 A1 | 9/2008 | Kavanaugh |
| 2009/0111143 A1 | 4/2009 | Goldenberg et al. |
| 2009/0175819 A1 | 7/2009 | Priest et al. |
| 2009/0202487 A1 | 8/2009 | Chang et al. |
| 2009/0291088 A1 | 11/2009 | Hariharan et al. |
| 2010/0226884 A1 | 9/2010 | Chang et al. |
| 2011/0020273 A1 | 1/2011 | Chang et al. |
| 2011/0064754 A1 | 3/2011 | Taylor et al. |
| 2011/0123436 A1 | 5/2011 | Chang et al. |
| 2011/0143417 A1 | 6/2011 | Chang et al. |
| 2011/0158905 A1 | 6/2011 | Goldenberg et al. |
| 2011/0189083 A1 | 8/2011 | Chang et al. |
| 2012/0093769 A1 | 4/2012 | Chang et al. |
| 2012/0196346 A1 | 8/2012 | Chang et al. |
| 2012/0276100 A1 | 11/2012 | Chang et al. |
| 2012/0276608 A1 | 11/2012 | Chang et al. |
| 2013/0078183 A1 | 3/2013 | Chang et al. |
| 2013/0164816 A1 | 6/2013 | Chang et al. |
| 2013/0177532 A1 | 7/2013 | Chang et al. |
| 2013/0217091 A1 | 8/2013 | Chang et al. |
| 2013/0295005 A1 | 11/2013 | Chang et al. |

FOREIGN PATENT DOCUMENTS

| | | |
|---|---|---|
| WO | 2006/107617 | 10/2006 |
| WO | 2006/107786 | 10/2006 |
| WO | 2007/046893 | 4/2007 |
| WO | 2007/075270 | 7/2007 |

OTHER PUBLICATIONS

Baxevanis, CN. "Antibody-based cancer therapy", Expert Opin Drug Discov. Apr. 2008;3(4):441-52.

Bendig, Methods: a Companion to Methods in Enzymology, vol. 8, pp. 83-93, 1995.

Benjamini et al., Immunology: A Short Course, 2nd Ed., 1991. p. 40.

Burtrum et al., "A fully human monoclonal antibody to the insulin-like growth factor I receptor blocks ligand-dependent signaling and inhibits human tumor growth in vivo", Cancer Res. Dec. 15, 2003;63(24):8912-21.

(56) References Cited

OTHER PUBLICATIONS

Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10):1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Cho et al., "The role of mammalian target of rapamycin inhibitors in the treatment of advanced renal cancer", Clin Cancer Res. Jan. 15, 2007;13(2 Pt 2):758s-763s.
Cohen et al., "Combination Therapy Enhances the Inhibition of Tumor Growth with the Fully Human Anti-Type 1 Insulin-Like Growth Factor Receptor Monoclonal Antibody CP-751,871", Clin. Cancer Res. Mar. 1, 2005;11(5):2063-73.
Eck and Wilson, Goodman & Gilman's The Pharmacological Basis of Therapeutics, 1996, McGraw-Hill, New York, pp. 77-101.
Ellis et al, Insulin-like growth factors in human breast cancer, Breast Cancer Res. Treat. 1998;52(1-3):175-84.
Gao et al., "Nonviral gene delivery: what we know and what is next", AAPS J. Mar. 23, 2007;9(1):E92-104.
Garber et al., "IGF-1: old growth factor shines as new drug target", J. Natl. Cancer Inst. Jun. 1, 2005;97(11):790-2.
Goldenberg et al., "Cancer Imaging and Therapy with Bispecific Antibody Pretargeting", Update Cancer Ther. Mar. 2007;2(1):19-31.
Govindan et al., "Designing immunoconjugates for cancer therapy", Expert Opin Biol Ther. Jul. 2012;12(7):873-90.
Haluska et al., "HER receptor signaling confers resistance to IGF-1R targeted therapy", J. Clin. Oncol., 2008 ASCO Annual Meeting Proceedings, vol. 26, No. 15S (May 20 Suppl.), 2008: 14510.
Jones et al., "Insulin-like growth factors and their binding proteins: biological actions", Endocr. Rev. Feb. 1995;16(1):3-34.
Kang et al., "IGF-1 inhibits the mitochondrial apoptosis program in mesangial cells exposed to high glucose", Am. J. Physiol. Renal Physiol. Nov. 2003;285(5):F1013-24.
Keyhanfar et al., "Precise mapping of an IGF-I-binding site on the IGF-1R", Biochem J. Jan. 1, 2007;401(1):269-77.
Liu et al., "Trop-2-targeting tetrakis-ranpirnase has potent antitumor activity against triple-negative breast cancer", Mol Cancer. Mar. 10, 2014;13:53.
Miller et al., "Type I insulin-like growth factor receptor as a therapeutic target in cancer", Cancer Res. Nov. 15, 2005;65(22):10123-7.
Niidome et al., "Gene therapy progress and prospects: nonviral vectors", Gene Ther. Dec. 2002;9(24):1647-52.
Parker et al., "Nonviral gene delivery: techniques and implications for molecular medicine", Expert Rev Mol Med. Sep. 3, 2003;5(22):1-15.
Paul, Fundamental Immunology, 3rd Edition, 1993, pp. 292-295.
Pollak et al., "Insulin-like growth factors and neoplasia", Nat. Rev. Cancer Jul. 2004;4(7):505-18.
Quek et al., "Combination mTOR and IGF-1R inhibition: phase I trial of everolimus and figitumumab in patients with advanced sarcomas and other solid tumors", Clin Cancer Res. Feb. 15, 2011;17(4):871-9.
Resnicoff et al., "The insulin-like growth factor I receptor protects tumor cells from apoptosis in vivo", Cancer Res. Jun. 1, 1995;55(11):2463-9.
Riedemann et al., "IGF1R signalling and its inhibition", Endocr. Relat. Cancer Dec. 2006;13 Suppl 1:S33-43.
Rossi et al., "CD20-targeted tetrameric interferon-alpha, a novel and potent immunocytokine for the therapy of B-cell lymphomas", Blood. Oct. 29, 2009;114(18):3864-71.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014;6(2):381-91.
Ryan et al., "Sorafenib with interferon alfa-2b as first-line treatment of advanced renal carcinoma: a phase II study of the Southwest Oncology Group", J Clin Oncol. Aug. 1, 2007;25(22):3296-301.
Ryan and Goss, "The emerging role of the insulin-like growth factor pathway as a therapeutic target in cancer", Oncologist Jan. 2008;13(1):16-24.
Sharkey et al., "Improved cancer therapy and molecular imaging with multivalent, multispecific antibodies", Cancer Biother Radiopharm. Feb. 2010;25(1):1-12.
Soos et al., "A panel of monoclonal antibodies for the type I insulin-like growth factor receptor. Epitope mapping, effects on ligand binding, and biological activity", J Biol Chem. Jun. 25, 1992;267(18):12955-63.
Van Golen et al., "IGF-I receptor activation and BCL-2 overexpression prevent early apoptotic events in human neuroblastoma", Cell Death Differ. Jul. 2000;7(7):654-65.
Wang et al.,Inhibition of insulin-like growth factor-I receptor (IGF-IR) signaling and tumor cell growth by a fully human neutralizing anti-IGF-IR antibody, Mol. Cancer Ther. 2005;4(8):1214-21.
Wu et al., "In vivo effects of the human type I insulin-like growth factor receptor antibody A12 on androgen-dependent and androgen-independent xenograft human prostate tumors", Clin. Cancer Res. Apr. 15, 2005;11(8):3065-74.
Zhang et al., "Tyrosine kinase signalling in breast cancer: insulin-like growth factors and their receptors in breast cancer", Breast Cancer Res. 2000;2(3):170-5.
Zhang et al., "In vivo gene delivery by nonviral vectors: overcoming hurdles?", Mol Ther. Jul. 2012;20(7):1298-304.
Adams et al., "Structure and function of the type 1 insulin-like growth factor receptor", Cell Mol Life Sci. Jul. 2000;57(7):1050-93.
McKern et al., "Crystallization of the first three domains of the human insulin-like growth factor-1 receptor", Protein Sci. Dec. 1997;6(12):2663-6.
Schumacher et al., "Insulin and insulin-like growth factor-1 binding specificity is determined by distinct regions of their cognate receptors", J Biol Chem. Oct. 15, 1991;266(29)19288-95.
Ullrich et al., "Insulin-like growth factor I receptor primary structure: comparison with insulin receptor suggests structural determinants that define functional specificity", EMBO J. Oct. 1986;5(10):2503-12.
Golay et al., "Mechanism of action of therapeutic monoclonal antibodies: promises and pitfalls of in vitro and in vivo assays", Arch Biochem Biophys. Oct. 15, 2012;526(2):146-53.
Jubala et al., "CD20 expression in normal canine B cells and in canine non-Hodgkin lymphoma", Vet Pathol. Jul. 2005;42(4):468-76.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes" EMBO J. 2001; 20:1651-1662.
Newlon et al., "The molecular basis for protein kinase A anchoring revealed by solution NMR" Nature Struct. Biol. 1999; 3:222-227.

(56) References Cited

OTHER PUBLICATIONS

Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region" FEBS Letters 246:57-64, 1989.
Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother. 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103(4):535-542 (1999).
Raefsky et al., "Studies of Interferon as a regulator of hematopoietic cells proliferation" J. Immunol. 135(4):2507-2512 (1985).
Rose et al., "Structural basis of dimerization, coactivator recognition and MODY3 mutations in HNF-1α" Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al., "Novel Designs of Multivalent Anti-CD20 Humanized Antibodies as Improved Lymphoma Therapeutics" Cancer Res. 68:8384-92 (2008).
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "A New Class of Hexavalent Bispecific Antibodies and Immunocytokines with Enhanced Pharmacokinetics and Improved Efficacy in Vivo", Blood (ASH Annual Meeting Abstracts) 2012 120: Abstract 2451.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the Gela-Goelams FL2000 study" Blood 2008; 112:4824-4831.
Santini et al., "Type I Interferon as a Powerful Adjuvant for Monocyte-derived Dendritic Cell Development and Activity In Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase" J. Biol. Chem. 265:21561-66 (1990).
Scott et al., "Cyclic nucleotide-dependent protein kinases" Pharmacol. Ther. 1991;50(1):123-45.

Seffernick et al., "Melamine Deaminase and Atrazine Chlorohydrolase: 98 Percent Identical but Functionally Different" J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody" Cancer Res. 68:5282-90 (2008).
Sharkey et al., "Metastatic Human Colonic Carcinoma: Molecular Imaging with Pretargeted SPECT and PET in a Mouse Model" Radiology 246:497-507 (2008).
Sidky et al., "Inhibition of Angiogenesis by Interferons: Effects on Tumor- and Lymphocyte-induced Vascular Responses" Cancer Res. 47:5155-5161, Oct. 1, 1987.
Stancovski et al., "Mechanistic aspects of the opposing effects of monoclonal antibodies to the ERBB2 receptor on tumor growth", Proc Natl Acad Sci U S A. Oct. 1, 1991;88(19):8691-5.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.
Stein et al., "Characterization of a humanized IgG4 anti-HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-α/β signalling to p53 responses in tumour suppression and antiviral defence" Nature Jul. 31, 2003;424(6948):516-23.
Taylor, S., "cAMP-dependent Protein Kinase" J. Biol. Chem. 1989;264(15):8443-8446.
Walsh et al., "An Adenosine 3', 5'-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody" J. Immunol. 165:4505-14 (2000).
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time" Nat. Rev. Mol. Cell Biol. 12:959-70 (2004).
Yu et al., "Interaction between bevacizumab and murine VEGF-A: a reassessment", Invest Ophthalmol Vis Sci. Feb. 2008;49(2):522-7.
Zhu et al., "Inhibition of tumor growth and metastasis by targeting tumor-associated angiogenesis with antagonists to the receptors of vascular endothelial growth factor" Invest. New Drugs 17:195-212, 1999.
Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract" FEBS Letters 2005; 579:3264-3270.
Banky et al., "Dimerization/Docking Domain of the Type Iα Regulatory Subunit of cAMP-dependent Protein Kinase" J. Biol. Chem. 273:35048-55, 1998.
Basu et al., "Structure-Function Engineering of Interferon-β-1b for Improving Stability, Solubility, Potency, Immunogenicity, and

(56) References Cited

OTHER PUBLICATIONS

Pharmacokinetic Properties by Site-Selective Mono-PEGylation" Bioconjugate Chem. 2006; 17:618-630.

Belardelli et al., "Interferon-alpha in tumor immunity and immunotherapy" Cytokine Growth Factor Rev. 13(2):119-134(2002).

Belardelli et al., "International Meeting on Cancer Vaccines: How Can We Enhance Efficacy of Therapeutic Vaccines?" Cancer Res. 64:6827-6830 (2004).

Belardelli et al., "The neglected role of type I interferon in the T-cell response: implications for its clinical use" Immunol. Today 17(8):369-72 (1996).

Biron et al., "Natural killer cells in antiviral defense: function and regulation by innate cytokines" Annu. Rev. Immunol. 17:189-220 (1999).

Brunda et al., "Modulation of Murine Natural Killer Cell Activity in Vitro and in Vivo by Recombinant Human Interferons" Cancer Res. 44:597-601 (1984).

Burns-Hamuro et al., "Distinct interaction modes of an AKAP bound to two regulatory subunit isoforms of protein kinase A revealed by amide hydrogen/deuterium exchange" Protein Science (2005), 14:2982-2992.

Carr et al., "Interaction of the Regulatory Subunit (RII) of cAMP-dependent Protein Kinase with RII-anchoring Proteins Occurs through an Amphipathic Helix Binding Motif" J. Biol. Chem. 266:14188-92 (1991).

Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).

Carrero et al., "Lymphocytes are detrimental during the early innate immune response against Listeria monocytogenes" J. Exp. Med. 203(4):933-940 (2006).

Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.

Chmura et al., "Antibodies with infinite affinity" Proc. Natl. Acad. Sci. USA 98(15):8480-8484 (2001).

Colledge et al., "AKAPs: from structure to function" Trends Cell Biol. 6:216-21 (1999).

Corbin et al., "Regulation of Adenosine 3',5'-Monophosphate-dependent Protein Kinase" J. Biol. Chem. 248:1813-21 (1973).

Dhalluin et al., "Structural and Biophysical Characterization of the 40 kDa PEG-Interferon-α2a and Its Individual Positional Isomers" Bioconjugate Chem. 2005;16:504-517.

Dodart et al., "Immunotherapy for Alzheimer's Disease: will vaccination work?" Trends Mol. Med. 9(3):85-87 (2003).

Doherty et al., "Site-Specific PEGylation of Engineered Cysteine Analogues of Recombinant Human Granulocyte-Macrophage Colony-Stimulating Factor" Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).

Ferrantini et al., "Interferon-α and cancer: Mechanisms of action and new perspectives of clinical use" Biochimie 89: 884-893 (2007).

Foser et al., "Improved biological and transcriptional activity of monopegylated interferon-α-2a isomers" The Pharmacogenomics J 3:312-319 (2003).

Gillies et al., "High-level expression of chimeric antibodies using adapted cDNA variable region cassettes" J. Immunol. Methods 125 (1989) 191-202.

Glennie et al., "Mechanisms of killing by anti-CD20 monoclonal antibodies" Mol. Immunol. 44:3823-3837 (2007).

Gold et al., "A Novel Bispecific, Trivalent Antibody Construct for Targeting Pancreatic Carcinoma", Cancer Res. 68:4819-26, 2008.

Gold et al., "Molecular Basis of AKAP Specificity for PKA Regulatory Subunits" Mol. Cell Nov. 3, 2006;24(3):383-95.

Goldenberg et al., "Multifunctional Antibodies by the Dock-and-Lock Method for Improved Cancer Imaging and Therapy by Pretargeting" J. Nucl. Med. 49:158-63, 2008.

Goldenberg et al., "Properties and structure-function relationships of veltuzumab (hA20), a humanized anti-CD20 monoclonal antibody" Blood 113:1062-70 (2009).

Goodson et al., "Site-Directed PEGylation of Recombinant Interleukin-2 at its Glycosylation Site" Nat. Biotechnology Apr. 1990;8(4):343-6.

Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.

Grimley et al., "Prolonged STAT1 Activation Related to the Growth Arrest of Malignant Lymphoma Cells by Interferon-α" Blood 91(8):3017-27 (1998).

Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).

Gutterman et al., "Cytokine therapeutics: Lessons from interferon α" Proc. Natl. Acad. Sci. USA 91:1198-205 (1994).

Harris et al., "Effect of pegylation on pharmaceuticals" Nat. Rev. Drug. Discov. 2:214-221 (2003).

Hausken et al. "Mutational Analysis of the A-Kinase Anchoring Protein (AKAP)-binding Site on RII" J. Biol. Chem. 271:29016-22 (1996).

Hodneland et al., Selective immobilization of proteins to self-assembled monolayers presenting active site-directed capture ligands, Proc. Natl. Acad. Sci. USA 2002; 99:5048-5052.

Huang et al., "Targeting IFN-α to B Cell Lymphoma by a Tumor-Specific Antibody Elicits Potent Antitumor Activities" J. Immunol. 179:6881-88 (2007).

Hundsrucker et al., "High-affinity AKAP7δ-protein kinase A interaction yields novel protein kinase A-anchoring disruptor peptides" Biochem. J. (2006) 396, 297-306.

Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).

Kinderman et al., "A Dynamic Mechanism for AKAP Binding to RII Isoforms of cAMP-Dependent Protein Kinase" Mol. Cell 24(3):397-408 (2006).

Kinstler et al., "Characterization and Stability of N-terminally PEGylated rhG-CSF" Pharm. Res. 1996;13(7):996-1002.

Kramer et al., "Cell and virus sensitivity studies with recombinant human alpha interferons" J. Interferon. Res. 3(4):425-35 (1983).

Le Bon et al., "Type I Interferons Potently Enhance Humoral Immunity and Can Promote Isotype Switching by Stimulating Dendritic Cells In Vivo" Immunity 14:461-470 (2001).

Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

Lohmann et al., "High-affinity binding of the regulatory subunit (RII) of cAMP-dependent protein kinase to microtubule-associated and other cellular proteins" Proc. Natl. Acad. Sci. USA 81:6723-27 (1984).

Luft et al., "Type I IFNs Enhance the Terminal Differentiation of Dendritic Cells" J. Immunol. 161:1947-1953 (1998).

Mason, Anthony J., "Functional Analysis of the Cysteine Residues of Activin A" Mol. Endocrinol. 8:325-32 (1994).

* cited by examiner

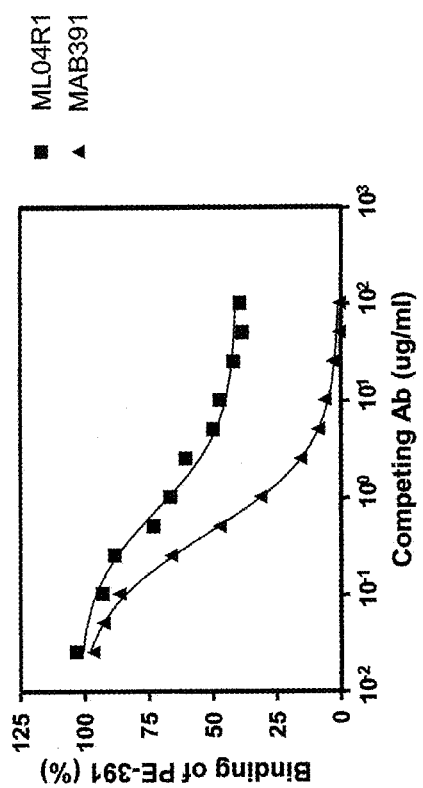
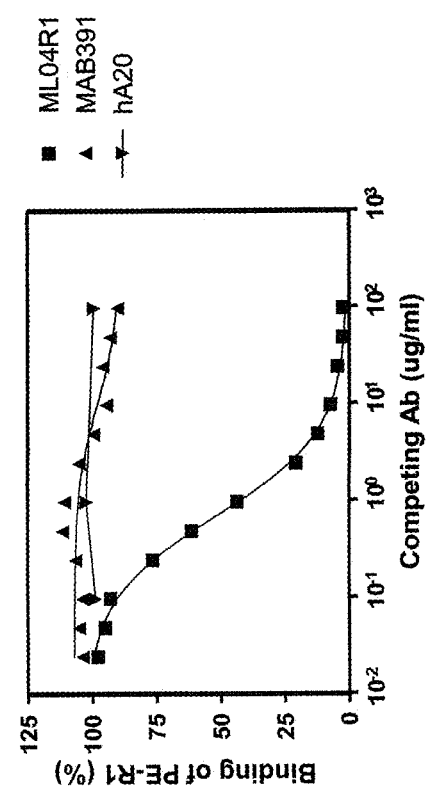
FIG. 8A
FIG. 8B

CLASS OF MONOSPECIFIC AND BISPECIFIC HUMANIZED ANTIBODIES THAT TARGET THE INSULIN-LIKE GROWTH FACTOR TYPE I RECEPTOR (IGF-1R)

RELATED APPLICATIONS

The present application is a divisional of U.S. patent application Ser. No. 14/598,664, filed Jan. 16, 2015, which was a continuation of U.S. patent application Ser. No. 14/061,176 (now abandoned), filed Oct. 23, 2013, which was a divisional of U.S. patent application Ser. No. 12/722,645 (now abandoned), filed Mar. 12, 2010, which was a continuation-in-part of U.S. patent application Ser. No. 12/689,336 (now abandoned), filed Jan. 19, 2010, which claimed the benefit under 35 U.S.C. 119(e) of Provisional U.S. Patent Application Ser. No. 61/145,896, filed Jan. 20, 2009. The present application is a continuation-in-part of U.S. patent application Ser. No. 14/505,595, filed Oct. 14, 2014, which was a divisional of U.S. patent application Ser. No. 13/688,812 (now issued U.S. Pat. No. 8,883,162), filed Nov. 29, 2012, which claimed the benefit under 35 U.S.C. 119(e) of U.S. Provisional Patent Application Ser. No. 61/566,273, filed Dec. 2, 2011, and 61/616,051, filed Mar. 27, 2012, and which was a continuation-in-part of U.S. patent application Ser. No. 13/483,761, filed May 30, 2012, which was a divisional of U.S. patent application Ser. No. 12/949,536 (now issued U.S. Pat. No. 8,211,440), filed Nov. 18, 2010, which was a divisional of U.S. patent application Ser. No. 12/396,605 (now issued U.S. Pat. No. 7,858,070), filed Mar. 3, 2009, which was a divisional of U.S. patent application Ser. No. 11/633,729 (now issued U.S. Pat. No. 7,527,787), filed Dec. 5, 2006, which was a continuation-in-part of PCT/US2006/010762, filed Mar. 24, 2006; PCT/US2006/012084, filed Mar. 29, 2006; PCT/US2006/025499, filed Jun. 29, 2006; U.S. patent application Ser. No. 11/389,358 (now issued U.S. Pat. No. 7,550,143), filed Mar. 24, 2006; Ser. No. 11/391,584 (now issued U.S. Pat. No. 7,521,056), filed Mar. 28, 2006 and Ser. No. 11/478,021 (now issued U.S. Pat. No. 7,534,866), filed Jun. 29, 2006. U.S. Ser. No. 11/633,729 claimed the benefit under 35 U.S.C. 119(e) of provisional U.S. Patent Application Ser. No. 60/751,196, filed Dec. 16, 2005 and 60/864,530, filed Nov. 6, 2006. The entire text of each priority application is incorporated herein by reference.

SEQUENCE LISTING

The instant application contains a Sequence Listing which has been submitted via EFS-Web and is hereby incorporated by reference in its entirety. Said ASCII copy, created on Jan. 14, 2015, is named IMM316US4_SL.txt, and is 31,769 bytes in size.

FIELD OF THE INVENTION

The present invention relates to antibodies and antigen-binding antibody fragments that bind to the insulin-like growth factor type I receptor (IGF-1R), but not to the insulin receptor (IR). In preferred embodiments, the anti-IGF-1R antibody is not an agonist for IGF-1R. In more preferred embodiments, the anti-IGF-1R antibody binds to an epitope of IGF-1R comprising the first half of the cysteine-rich domain of IGF-1R, between amino acid residues 151 and 222. In most preferred embodiments, the anti-IGF-1R antibody does not block binding of IGF-1 or IGF-2 to isolated IGF-1R, but effectively neutralizes the activation of IGF-1R by IGF-1 in situ in intact cells or tissues. In other embodiments, the mouse anti-IGF-1R antibody, designated as R1, comprises the heavy chain variable region complementarity determining region (CDR) sequences CDR1 (DYYMY, SEQ ID NO:1), CDR2 (YITNYGGSTYYPDTVKG, SEQ ID NO:2) and CDR3 (QSNYDYDGWFAY, SEQ ID NO:3) and the light chain variable region CDR sequences CDR1 (KASQEVGTAVA, SEQ ID NO:4), CDR2 (WASTRHT, SEQ ID NO:5) and CDR3 (QQYSNYPLT, SEQ ID NO:6). In more preferred embodiments, the anti-IGF-1R antibody is a humanized, chimeric or human R1 antibody, designated as hR1, comprising the CDR sequences recited above. In most preferred embodiments, the anti-IGF-R1 antibody is a humanized antibody comprising the recited CDR sequences and human antibody constant and framework (FR) region sequences.

Such antibodies and fragments are of use for detection and/or therapy of a wide variety of cancers where IGF-1R expression is important for cancer cell transformation, growth, survival, metastasis or resistance to other therapeutic agents, including but not limited to Wilms' tumor, Ewing sarcoma, neuroblastoma, neuroendocrine tumors, melanoma, glioblastomas, skin, breast, head-and-neck, colon, rectal, gastric, esophageal, ovarian, bladder, prostate, liver, renal, pancreatic and/or lung cancers, as well as lymphomas, leukemias, and myelomas. The anti-IGF-1R antibodies and/or antibody fragments may be used in compositions and therapeutic methods either alone or in conjunction with other cytotoxic agents such as cancer chemotherapeutic agents, pro-apoptotic agents, radionuclides, EGFR inhibitors (e.g. erlotinib or anti-EGFR antibodies), anti-angiogenesis agents (e.g., anti-VEGF and anti-PlGF peptides or antibodies) and/or other IGF-1R inhibitors such as tryphostins (e.g., AG1024, AG538), pyrrolo[2,3-d]-pyrimidine derivatives (e.g., NVP-AEW541) or other anti-IGF-1R antibodies or antibodies against other tumor-associated antigens (TAA). The anti-IGF-1R antibodies may be naked antibodies or may be conjugated to one or more therapeutic and/or diagnostic agents. The antibodies may be murine, chimeric, humanized or human anti-IGF-1R antibodies.

Other embodiments may relate to multispecific antibodies, bispecific antibodies, antibody fusion proteins or fragments thereof comprising at least one anti-IGF-1R monoclonal antibody (MAb) or fragment thereof, in some cases in combination with a second, different antibody or fragment. The antibodies, fragments or antibody fusion proteins may be administered alone, as a therapeutic immunoconjugate or in combination with one or more therapeutic agents, with other naked antibodies or other immunoconjugates. Still other embodiments relate to DNA sequences encoding anti-IGF-1R antibodies or antibody fusion proteins, vectors and host cells containing the DNA sequences, and methods of making the anti-IGF-1R antibodies. Further embodiments concern multivalent, multispecific and/or multifunctional constructs made by the dock-and-lock (DNL) technique that incorporate anti-IGF-1R antibodies, fusion proteins and/or fragments thereof.

RELATED ART

The insulin-like growth factor type I receptor (IGF-1R) is a member of the large class of tyrosine kinase receptors, which regulate a variety of intracellular pathways. IGF-1R binds IGF-1, a polypeptide hormone structurally similar to insulin (Laron, Mol Pathol. 2001, 54:311-16). The IGF-1 receptor is homologous to the insulin receptor (IR), sharing about 70% overall sequence homology with IR (Riedemann and Macaulay, Endocrine-Related Cancer, 2006, 13:S33-43). Not surprisingly, inhibitors developed against IGF-1R tend to show cross-reactivity with the insulin receptor, accounting for at least part of the toxicity profiles of such compounds (Miller and Yee, 2005, Cancer Res. 65:10123-27; Riedemann and Macaulay, 2006).

The IGF system plays an important role in regulating cell proliferation, differentiation, apoptosis and transformation (Jones et al, Endocrinology Rev. 1995. 16:3-34). The IGF system comprises two receptors, insulin like growth factor receptor 1 (IGF-1R; CD221) and insulin like growth factor receptor 2 (IGF-2R; CD222); two ligands, insulin like growth factor 1 (IGF-1) and IGF-2; and several IGF binding proteins (IGFBP-1 to IGFBP-6). In addition, a large group of IGFBP proteases (e.g., caspases, metalloproteinases, prostate-specific antigen) hydrolyze IGF bound IGFBP to release free IGFs, which then interact with IGF-1R and IGF-2R.

IGF-1R comprises two extracellular α subunits (130-135 kD) and two membrane spanning β-subunits (95 kD) that contain the cytoplasmic tyrosine kinase domain. IGF-1R, like the insulin receptor (IR), differs from other receptor tyrosine kinase family members by having a covalent dimeric (α2β2) structure. IGF-1R contains 84% sequence identity to IR in the kinase domain, while the membrane and C-terminal regions share 61% and 44% sequence identity, respectively (Ulrich et al., EMBO J., 1986, 5:2503-12; Blakesley et al., Cytokine Growth Factor Rev., 1996. 7:153-56).

IGF-1 and IGF-2 are activating ligands of IGF-1R. Binding of IGF-1 and IGF-2 to the α-chain induces conformational changes that result in autophosphorylation of each β-chain at specific tyrosine residues, converting the receptor from the unphosphorylated inactive state to the phosphorylated active state. The activation of three tyrosine residues in the activation loop (Tyr residues at 1131, 1135 and 1136) of the kinase domain leads to an increase in catalytic activity that triggers docking and phosphorylation of substrates such as IRS-1 and Shc adaptor proteins. Activation of these substrates leads to phosphorylation of additional proteins involved in the signaling cascade of survival (PI3K, AKT, TOR, S6) and/or proliferation (mitogen-activated protein kinase, p42/p44) (Pollak et al., Nature Reviews Cancer. 2004. 4:505-516; Baserga et al., Biochim Biophys Acta. 1997. 1332:F105-F126; Baserga et al, Int. J. Cancer. 2003. 107:873-77).

IGF-1R has anti-apoptotic effects in both normal and cancer cells (Resnicoff et al., 1995, Cancer Res. 55:2463-69; Kang et al., Am J Physiol Renal Physiol., 2003, 285:F1013-24; Riedemann and Macaulay, 2006). IGF-1R activation has been reported to be significant in the development of resistance to a variety of cytotoxic agents, such as chemotherapeutic agents, radionuclides and EGFR inhibitors (Jones et al., Endocr Relat Cancer 2004, 11:793-814; Warshamana-Greene et al., 2005, Clin. Cancer Res. 11:1563-71; Riedemann and Macaulay, 2006; Lloret et al., 2007, Gynecol. Oncol. 106:8-11). IGF-1R is overexpressed in a wide range of tumor lines, such as melanoma, neuroblastoma, colon cancer, prostate cancer, renal cancer, breast cancer and pancreatic cancer (Ellis et al., 1998, Breast Cancer Treat. 52:175-84; van Golen et al., 2000, Cell Death Differ. 7:654-65; Zhang et al., 2001, Breast Cancer Res. 2:170-75; Jones et al., 2004; Riedemann and Macaulay, 2006). A functional IGF-1R is required for transformation and promotes cancer cell growth, survival and metastasis (Riedemann and Macaulay, 2006).

Attempts have been made to develop IGF-1R inhibitors for use as anti-cancer agents, such as tyrphostins, pyrrolo [2,3-d]-pyrimidine derivatives, nordihydroguaiaretic acid analogs, diaryureas, AG538, AG1024, NVP-AEW541, NVP-ADW742, BMS-5326924, BMS-554417, OSI-906, INSM-18, luteolin, simvastatin, silibinin, black tea polyphenols, picropodophyllin, anti-IGF-1R antibodies and siRNA inhibitors (Arteaga et al., 1998, J Clin Invest. 84:1418-23; Warshamana-Greene et al., 2005; Klein and Fischer, 2002, Carcinogenesis 23:217-21; Blum et al., 2000, Biochemistry 39:15705-12; Garcia-Echeverria et al., 2004, Cancer Cell 5:231-39; Garber, 2005, JNCI 97:790-92; Bell et al., 2005, Biochemistry 44:930-40; Wu et al., 2005, Clin Cancer Res 11:3065-74; Wang et al., 2005, Mol Cancer Ther 4:1214-21; Singh and Agarwal, 2006, Mol Carinog. 45:436-42; Gable et al., 2006, Mol Cancer Ther 5:1079-86; Niu et al., Cell Biol Int., 2007, 31:156-64; Blecha et al., 2007, Biorg Med Chem Lett. 17:4026-29; Qian et al., 2007, Acta Biochim Biophys Sin, 39:137-47; Fang et al., 2007, Carcinogenesis 28:713-23; Cohen et al., 2005, Clin Cancer Res 11:2063-73; Sekine et al., Biochem Biophys Res Commun., 2008, 25:356-61; Haluska et al., 2008, J Clin Oncol. 26:May 20 suppl; abstr 14510; U.S. Patent Application Publ. No. 2006-233810, the Examples section of each of which is incorporated herein by reference). Typically, these agents have tended to cross-react to a greater or lesser extent with both IGF-1R and IR and/or to act as IGF-1R agonists. The use of such agents for cancer therapy has been limited by their toxicity (Riedemann and Macaulay, 2006). A need exists in the field for anti-IGF-1R antibodies that (i) do not cross-react with the insulin receptor, (ii) exhibit a lower toxicity profile, (iii) neutralize the effect of IGF-1 and IGF-2 on IGF-1R-expressing cells; (iv) preferably do not act as IGF-1R agonists; and (v) may not compete for binding to isolated IGF-1R with IGF-1 or IGF-2.

SUMMARY OF THE INVENTION

The present invention provides compositions and methods of use of anti-IGF-1R antibodies or antigen-binding fragments thereof. In preferred embodiments, the anti-IGF-1R antibodies bind to IGF-1R but not to IR. In more preferred embodiments the anti-IGF-1R antibodies are not agonists of IGF-1R. In most preferred embodiments, the anti-IGF-1R antibodies bind to an epitope of IGF-1R comprising the first half of the cysteine-rich domain of IGF-1R, between amino acid residues 151 and 222 of the human IGF-1R sequence. (See, e.g., Adams et al., Cell Mol Life Sci 57:1050-93, 2000; NCBI Accession No. AAB22215 (SEQ ID NO: 56)). Protease cleavage by furin results in production of the α-chain, comprising residues 1-706, and the β-chain, comprising residues 711-1337. Residues 151-222 consists of the N-terminal half of the cysteine-rich domain (residues 151-300).

Preferably, the anti-IGF-1R antibody is a murine, chimeric, humanized or human antibody or antigen-binding fragment thereof comprising the heavy chain CDR sequences CDR1 (DYYMY, SEQ ID NO:1), CDR2 (YIT-NYGGSTYYPDTVKG, SEQ ID NO:2) and CDR3 (QSNY-DYDGWFAY, SEQ ID NO:3) and the light chain CDR sequences CDR1 (KASQEVGTAVA, SEQ ID NO:4), CDR2 (WASTRHT, SEQ ID NO:5) and CDR3 (QQYSNYPLT, SEQ ID NO:6). In alternative embodiments, the anti-IGF-1R antibody is a chimeric, humanized or human antibody that binds to the same epitope and/or that blocks binding to IGF-1R of a murine R1 antibody comprising the heavy chain CDR sequences CDR1 (DYYMY, SEQ ID NO:1), CDR2

(YITNYGGSTYYPDTVKG, SEQ ID NO:2) and CDR3 (QSNYDYDGWFAY, SEQ ID NO:3) and the light chain CDR sequences CDR1 (KASQEVGTAVA, SEQ ID NO:4), CDR2 (WASTRHT, SEQ ID NO:5) and CDR3 (QQYSNYPLT, SEQ ID NO:6). The anti-IGF-1R antibody may be a naked antibody or may be an immunoconjugate attached to at least one therapeutic agent and/or at least one diagnostic agent.

Various embodiments may concern multispecific antibodies, bispecific antibodies or antibody fusion proteins comprising at least one anti-IGF-1R MAb or fragment thereof or a first anti-IGF-1R MAb or fragment thereof and a second MAb. Other embodiments may concern pharmaceutical compositions for or methods of use of a first anti-IGF-1R MAb or fragment thereof and a second MAb for therapy of cancer. The second MAb may bind to a tumor-associated antigen (TAA), or a hapten, for example on a targetable construct. A variety of tumor-associated antigens are known in the art and any such known TAA may targeted by a second MAb, including but not limited to carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, AFP, PSMA, CEACAM5, CEACAM-6, B7, ED-B of fibronectin, Factor H, FHL-1, Flt-3, folate receptor, GROB, HMGB-1, hypoxia inducible factor (HIF), HM1.24, insulin-like growth factor-1 (ILGF-1), IFN-$\gamma$, IFN-$\alpha$, IFN-$\beta$, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-$\alpha$, TRAIL receptor (R1 and R2), VEGFR, EGFR, PlGF, complement factors C3, C3a, C3b, C5a, C5, and an oncogene product.

The second MAb may be selected from any of a wide variety of anti-cancer antibodies known in the art, including but not limited to hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. Provisional Patent Application 61/145,896), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections. The second MAb may also be selected from any anti-hapten antibody known in the art, including but not limited to h679 (U.S. Pat. No. 7,429,381) and 734 (U.S. Pat. No. 7,405,320) or h734, the text of each of which is incorporated herein by reference. In certain embodiments, a second, different anti-IGF-1R antibody may be used, such as any of the anti-IGF-1R antibodies in clinical development (see, e.g., Ryan and Goss, The Oncologist, 2008, 13:16-24).

Other embodiments may concern therapeutic or diagnostic conjugates of anti-IGF-1R MAbs or fragments thereof or antibody fusion proteins, bound to at least one therapeutic agent or at least one diagnostic agent. Antibodies and fusion proteins with multiple therapeutic agents of the same or different type are also encompassed. In alternative embodiments, the antibodies, fragments or fusion proteins may be used in therapeutic or diagnostic pre-targeting methods, for example using bispecific antibodies with one arm that binds specifically to a tumor-associated antigen and a second arm that binds to a targetable construct attached to one or more diagnostic or therapeutic agents. Methods of pre-targeting with bispecific antibodies are well known in the art (see, e.g., U.S. Pat. Nos. 7,300,644; 7,138,103; 7,074,405; 7,052,872; 6,962,702; 6,458,933, the Examples section of each of which is incorporated herein by reference).

Various embodiments concern methods of using the anti-IGF-1R MAbs or fragments thereof or antibody fusion proteins for therapy or diagnosis, either alone or in combination with one or more other therapeutic agents. The anti-IGF-1R MAb may be used as a naked antibody or as an immunoconjugate attached to one or more therapeutic agents and/or diagnostic agents. Either naked anti-IGF-1R MAbs or immunoconjugates may be used in combination therapies administered before, simultaneously with or after one or more other therapeutic agents. Any therapeutic agent known in the art, as discussed in more detail below, may be utilized in combination with or attached to an anti-IGF-1R MAb, including but not limited to radionuclides, immunomodulators, anti-angiogenic agents, cytokines, chemokines, growth factors, hormones, drugs, prodrugs, enzymes, oligonucleotides, siRNAs, pro-apoptotic agents, photoactive therapeutic agents, cytotoxic agents, chemotherapeutic agents, toxins, other antibodies or antigen binding fragments thereof. In preferred embodiments the other therapeutic agent may be an EGFR inhibitor (e.g., erlotinib or anti-EGFR antibody, such as erbitux) and/or other IGF-1R inhibitors such as tryphostins (e.g., AG1024, AG538), pyrrolo[2,3-d]-pyrimidine derivatives (e.g., NVP-AEW541) or other anti-IGF-1R antibodies.

Any cancer or diseased cell that expresses IGF-1R may be treated and/or diagnosed with the anti-IGF-1R antibodies, including but not limited to Wilms' tumor, Ewing sarcoma, neuroendocrine tumors, glioblastomas, neuroblastoma, melanoma, skin, breast, colon, rectum, prostate, liver, renal, pancreatic and/or lung cancer, as well as lymphomas, leukemias, and myelomas. Other forms of cancer that may be treated include but are not limited to acute lymphoblastic leukemia, acute myelogenous leukemia, biliary cancer, cervical cancer, chronic lymphocytic leukemia, chronic myelogenous leukemia, endometrial cancer, esophageal cancer, gastric cancer, head and neck cancer, Hodgkin's lymphoma, medullary thyroid carcinoma, non-Hodgkin's lymphoma, ovarian cancer, glioma and urinary bladder cancer.

Certain embodiments may comprise the therapeutic and/or diagnostic use of chimeric, humanized or human R1 antibodies comprising the heavy chain CDR sequences CDR1 (DYYMY, SEQ ID NO:1), CDR2 (YITNYGGSTYYPDTVKG, SEQ ID NO:2) and CDR3 (QSNYDYDGWFAY, SEQ ID NO:3) and the light chain CDR sequences CDR1 (KASQEVGTAVA, SEQ ID NO:4), CDR2 (WASTRHT, SEQ ID NO:5) and CDR3 (QQYSNYPLT, SEQ ID NO:6). The use of chimeric antibodies is preferred because they do not elicit as strong a human anti-mouse antibody (HAMA) response as murine antibodies. The use of humanized antibodies is even more preferred, in order to further reduce the possibility of inducing a HAMA reaction. As discussed below, techniques for humanization of murine antibodies by replacing murine framework and constant region sequences with corresponding human antibody framework and constant region sequences are well known in the art and have been applied to numerous murine anticancer antibodies. Antibody humanization may also involve the substitution of one or more human framework amino acid residues with the corresponding residues from the parent murine framework region sequences.

Still other embodiments relate to DNA sequences encoding anti-IGF-1R antibodies or antibody fusion proteins, vectors and host cells containing the DNA sequences, and methods of making the anti-IGF-1R antibodies. In preferred embodiments, the DNA sequences may comprise sequences coding for the hR1 VH (SEQ ID NO:9) and hR1 VK (SEQ ID NO:10) variable region amino acid sequences. Further embodiments concern multivalent, multispecific and/or multifunctional constructs made by the dock-and-lock (DNL) technique that incorporate anti-IGF-1R antibodies, fusion proteins and/or fragments thereof. Compositions and methods for production and use of DNL constructs have been reported (see, e.g., U.S. Pat. Nos. 7,521,056; 7,550,143; 7,534,866; 7,527,787 and U.S. patent application Ser. No. 11/925,408, filed Oct. 26, 2007, and Ser. No. 12/418,877, filed Apr. 6, 2009; the Examples section of each of which is incorporated herein by reference).

BRIEF DESCRIPTION OF THE FIGURES

FIG. 8A. Binding of R1 antibody is not competitive with MAB391. Binding of fluorescently labeled R1 antibody to immobilized rhIGF-1R was determined in the presence of competing murine R1 antibody (ML04R1), MAB391, or control non-specific antibody hA20, which binds to CD20. The R1 antibody did not compete for binding to IGF-1R with MAB391.

FIG. 8B. Binding of R1 antibody is not competitive with MAB391. Binding of fluorescently labeled MAB391 antibody to immobilized rhIGF-1R was determined in the presence of competing murine R1 antibody (ML04R1) or MAB391. The R1 antibody did not compete for binding to IGF-1R with MAB391.

DETAILED DESCRIPTION OF THE INVENTION

Definitions

Figure 1:
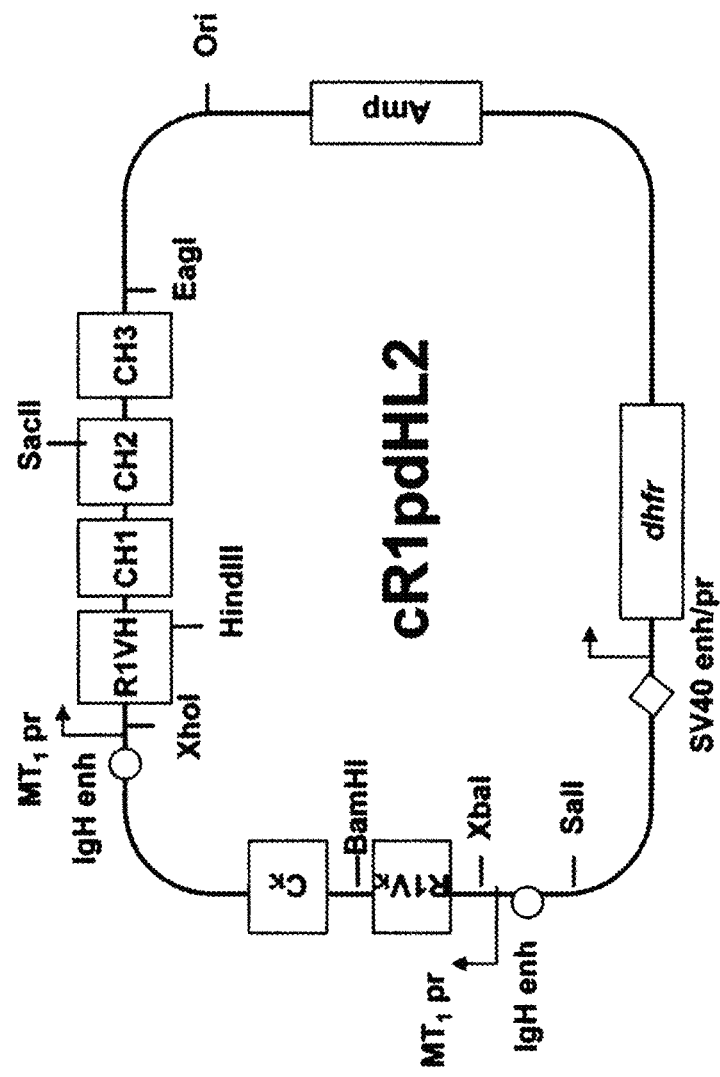
FIG. 1. Schematic diagram of plasmid cR1pdHL2.

As used herein, the terms "a", "an" and "the" may refer to either the singular or plural, unless the context otherwise makes clear that only the singular is meant.

As used herein, the term "about" means plus or minus ten percent (10%) of a value. For example, "about 100" would refer to any number between 90 and 110.

An antibody refers to a full-length (i.e., naturally occurring or formed by normal immunoglobulin gene fragment recombinatorial processes) immunoglobulin molecule (e.g., an IgG antibody) or an immunologically active, antigen-binding portion of an immunoglobulin molecule, like an antibody fragment.

An antibody fragment is a portion of an antibody such as F(ab')$_2$, F(ab)$_2$, Fab', Fab, Fv, scFv and the like. Regardless of structure, an antibody fragment binds with the same antigen that is recognized by the intact antibody. For example, an anti-IGF-1R monoclonal antibody fragment binds to IGF-1R. The term "antibody fragment" also includes isolated fragments consisting of the variable regions, such as the "Fv" fragments consisting of the variable regions of the heavy and light chains and recombinant single chain polypeptide molecules in which light and heavy variable regions are connected by a peptide linker ("scFv proteins"). As used herein, the term "antibody fragment" does not include portions of antibodies without antigen binding activity, such as Fc fragments or single amino acid residues.

A naked antibody or naked antibody fragment refers to an antibody or antigen binding fragment thereof which is not conjugated to a therapeutic agent. Naked antibodies may include murine monoclonal antibodies, as well as recombinant antibodies, such as chimeric, humanized or human antibodies.

A therapeutic agent is a molecule or atom which is administered separately, concurrently or sequentially with an antibody moiety or conjugated to an antibody moiety, i.e., antibody or antibody fragment, and is useful in the treatment of a disease. Non-limiting examples of therapeutic agents include antibodies, antibody fragments, drugs, toxins, nucleases, hormones, immunomodulators, chelators, boron compounds, photoactive agents, oligonucleotides (e.g. antisense oligonucleotides or RNAi) and radioisotopes.

A diagnostic agent is a detectable molecule or atom that may be conjugated to an antibody, antibody fragment, targetable construct or other moiety for delivery to a cell, tissue, pathogen or other target associated with a disease or medical condition. Useful diagnostic agents include, but are not limited to, radioisotopes, dyes, contrast agents, fluorescent compounds or molecules and enhancing agents (e.g. paramagnetic ions for magnetic resonance imaging). In certain embodiments, a diagnostic agent may be an F-18 labeled moiety (e.g., U.S. patent application Ser. Nos. 11/960,262; 12/112,289; PCT Patent Application Serial No. PCT/US08/62108; the Examples section of each of which is incorporated herein by reference.)

An immunoconjugate is a conjugate of an antibody component with at least one therapeutic or diagnostic agent. An antibody component may be conjugated with multiple therapeutic and/or diagnostic agents to form an immunoconjugate.

The term antibody fusion protein may refer to a recombinantly produced antigen-binding molecule in which one or more of the same or different single-chain antibody or antibody fragment segments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only bind with one epitope. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase. However, the term is not limiting and a variety of protein or peptide effectors may be incorporated into a fusion protein. In another non-limiting example, a fusion protein may comprise an AD or DDD sequence for producing a DNL construct as discussed below.

A multispecific antibody is an antibody that can bind simultaneously to at least two targets that are of different structure, e.g., two different antigens, two different epitopes on the same antigen, or a hapten and/or an antigen or epitope. One specificity may be for a B-cell, T-cell, myeloid-, plasma- or mast-cell antigen or epitope. Another specificity may be to a different antigen on the same cell type, such as IGF-1R, CD19, CD20, CD21, CD23, CD45, CD80, HLA-DR, CD74, MUC1, and CD22 on B-cells. However, the second antigen is not limiting and other target antigens of use may be selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, CD20, IGF-1R, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CEACAM5, CEACAM6, B7, ED-B fibronectin, Factor H, FHL-1, Flt-3, folate receptor, GROB, HMGB-1, hypoxia inducible factor (HIF), HM1.24, insulin-like growth factor-1 (ILGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, PAM4 antigen, NCA-95, NCA-90, PSMA, EGP-1, EGP-2, AFP, Ia, HM1.24, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product. Multispecific, multivalent antibodies are constructs that have more than one binding site, and the binding sites are of different specificity.

In various embodiments, the present invention provides humanized, chimeric or human anti-IGF-1R antibodies, and antibody fusion proteins thereof, useful for treatment of mammalian subjects, humans and domestic animals, alone, as a conjugate or administered in combination with other therapeutic agents, including other naked antibodies and antibody therapeutic conjugates.

Preferably, the anti-IGF-1R antibody exhibits one or more functional characteristics selected from the group consisting of: (i) binds to IGF-1R but not to IR; (ii) is not an agonist of IGF-1R; (iii) does not block binding of IGF-1 or IGF-2 to isolated IGF-1R; (iv) effectively neutralizes the activation of IGF-1R by IGF-1 in intact cells or tissues; and (v) binds to an epitope of IGF-1R comprising the first half of the cysteine-rich domain of IGF-1R, between amino acid residues 151 and 222 of the human IGF-1R sequence.

In other preferred embodiments, the anti-IGF-1R MAbs or fragments thereof comprise the heavy chain variable region complementarity determining region (CDR) sequences CDR1 (DYYMY, SEQ ID NO:1), CDR2 (YIT-NYGGSTYYPDTVKG, SEQ ID NO:2) and CDR3 (QSNY-DYDGWFAY, SEQ ID NO:3) and the light chain variable region CDR sequences CDR1 (KASQEVGTAVA, SEQ ID NO:4), CDR2 (WASTRHT, SEQ ID NO:5) and CDR3 (QQYSNYPLT, SEQ ID NO:6). In most preferred embodiments, the anti-IGF-1R antibody or fragment thereof is hR1.

The humanized anti-IGF-1R MAb or fragment thereof may comprise the CDRs of a murine anti-IGF-1R MAb and the framework (FR) and constant regions of the light and heavy chain variable regions of one or more human antibodies, while retaining the IGF-1R targeting specificity of the parent murine anti-IGF-1R MAb. The humanized anti-IGF-1R MAb or fragment thereof may further comprise at least one amino acid from the corresponding FRs of the parent murine MAb. The murine framework amino acid residues can be substituted in the human FR regions of the light and heavy variable chains if necessary to maintain proper binding or to enhance binding to the IGF-1R antigen. More preferably the humanized anti-IGF-1R MAb or fragment thereof comprises the amino acid sequences of hR1 VH (SEQ ID NO:9) and hR1 VK (SEQ ID NO:10).

Chimeric anti-IGF-1R MAbs or fragments thereof may comprise the variable region sequences of a murine anti-IGF-1R antibody, attached to human antibody constant region sequences. In preferred embodiments, the chimeric anti-IGF-1R MAb comprises the heavy and light chain variable region sequences of murine R1 VH (SEQ ID NO:7) and R1 VK (SEQ ID NO:8).

Certain embodiments may concern an anti-IGF-1R MAb or fragment thereof that blocks binding to IGF-1R of a murine, chimeric, humanized or human antibody comprising the heavy chain complementarity determining region (CDR) sequences CDR1 (DYYMY, SEQ ID NO:1), CDR2 (YIT-NYGGSTYYPDTVKG, SEQ ID NO:2) and CDR3 (QSNY-DYDGWFAY, SEQ ID NO:3) and the light chain CDR sequences CDR1 (KASQEVGTAVA, SEQ ID NO:4), CDR2 (WASTRHT, SEQ ID NO:5) and CDR3 (QQYSNYPLT, SEQ ID NO:6).

Other embodiments may encompass antibody fusion proteins comprising at least one anti-IGF-1R MAb or fragment thereof, as described above. The antibody fusion protein may comprise at least one first anti-IGF-1R MAb or fragment thereof and at least one second MAb or fragment thereof. More preferably the second MAb binds to an antigen selected from the group consisting of B7, CD4, CD5, CD8 CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD55, CD59, CD66a-e, CD70, CD74, CD79a, CD80, CD95, CD126, CD133, CD138, CD154, CEACAM5, CEACAM6, PAM4 antigen, PSMA, AFP, EGP-1, EGP-2, MIF, ED-B fibronectin, IL-2, IL-6, IL-25, MUC1, MUC2, MUC3, MUC4, MUC5, NCA-90, NCA-95, Ia, HM1.24, HLA-DR, tenascin, T101, TAC, TRAIL-R1, TRAIL-R2, VEGFR, EGFR, PlGF, Flt-3, ILGF, complement factor C5, and an oncogene product. Alternatively the second MAb may be an anti-IGF-1R MAb that is different than the anti-IGF-1R MAb described herein.

Amino Acid Substitutions

In certain embodiments, the disclosed methods and compositions may involve production and use of antibodies or antigen-binding fragments thereof with one or more substituted amino acid residues. As discussed below, methods for making monoclonal antibodies against virtually any target antigen are well known in the art. Typically, these result in production of murine antibodies against a target antigen. As is well known in the art, the antigen-binding specificity of murine monoclonal antibodies is determined largely by the hypervariable complementarity determining region (CDR) sequences. Murine antibodies generally comprise 6 CDR sequences, 3 on the antibody light chain and 3 on the heavy chain. As described in detail below, chimeric, humanized or human versions of murine antibodies may be constructed by techniques such as CDR grafting, where the murine CDR sequences are inserted into, for example, human antibody framework and constant region sequences, or by attaching the entire murine variable region sequences to human antibody constant region sequences. In alternative embodiments, the variable region sequences of an antibody may be constructed, for example, by chemical synthesis and assembly of oligonucleotides encoding the entire light and heavy chain variable regions of an antibody.

In various embodiments, the structural, physical and/or therapeutic characteristics of native, chimeric, humanized or human antibodies may be optimized by replacing one or more amino acid residues. For example, it is well known in the art that the functional characteristics of humanized antibodies may be improved by substituting a limited number of human framework region (FR) amino acids with the corresponding FR amino acids of the parent murine antibody. This is particularly true when the framework region amino acid residues are in close proximity to the CDR residues.

In other cases, the therapeutic properties of an antibody, such as binding affinity for the target antigen, the dissociation- or off-rate of the antibody from its target antigen, or even the effectiveness of induction of CDC (complement-dependent cytotoxicity) or ADCC (antibody dependent cellular cytotoxicity) by the antibody, may be optimized by a limited number of amino acid substitutions. Such substitutions may even occur, for example, in the CDR portions of the antibody. However, amino acid substitution is not limited to the CDR or framework region sequences of antibodies and may also occur, for example, in the Fc portion of an antibody.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan, tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For CDR residues, the residue in the free antibody would normally be assumed to be solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Preparation of Monoclonal Antibodies Including Chimeric, Humanized and Human Antibodies Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., Proc. Nat'l Acad. Sci. USA 6: 3833 (1989). Techniques for constructing chimeric antibodies are well known to those of skill in the art. As an example, Leung et al., Hybridoma 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., Nature 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the µ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XenoMouse® (e.g., Green et al., 1999, *J. Immunol. Methods* 231:11-23, incorporated herein by reference) from Abgenix (Fremont, Calif.). In the XenoMouse® and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

Production of Antibody Fragments

Antibody fragments which recognize specific epitopes can be generated by known techniques. The antibody fragments are antigen binding portions of an antibody, such as $F(ab')_2$, Fab', $F(ab)_2$, Fab, Fv, sFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science,* 246:1274-1281) to allow rapid and easy identification of monoclonal Fab' fragments with the desired specificity.

A single chain Fv molecule (scFv) comprises a $V_L$ domain and a $V_H$ domain. The $V_L$ and $V_H$ domains associate to form a target binding site. These two domains are further covalently linked by a peptide linker (L). Methods for making scFv molecules and designing suitable peptide linkers are described in U.S. Pat. No. 4,704,692, U.S. Pat. No. 4,946,778, R. Raag and M. Whitlow, "*Single Chain Fvs.*" FASEB Vol 9:73-80 (1995) and R. E. Bird and B. W. Walker, "*Single Chain Antibody Variable Regions*," TIBTECH, Vol 9: 132-137 (1991), incorporated herein by reference.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an enzymatic cleavage using papain produces two monovalent Fab fragments and an Fc fragment. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). Pre-targeting methods with bispecific antibodies comprising at least one binding site for a tumor-associated antigen or other disease target, as well as at one binding site for a targetable construct conjugated to therapeutic or diagnostic agents, are also well known in the art (see, e.g., U.S. Pat. Nos. 7,300,644; 7,138,103; 7,074,405; 7,052,872; 6,962,702; 6,458,933, the Examples section of each of which is incorporated herein by reference).

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature. 1985; 314:628-631; Perez, et al. Nature. 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405, the Examples section of each incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,550,143; 7,534,866; 7,527,787 and U.S. patent application Ser. No. 11/925,408, filed Oct. 26, 2007, and Ser. No. 12/418,877, filed Apr. 6, 2009; the Examples section of each of which is incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies, either as naked antibody moieties or in combination with a wide range of other effector molecules such as immunomodulators, enzymes, chemotherapeutic agents, chemokines, cytokines, diagnostic agents, therapeutic agents, radionuclides, imaging agents, anti-angiogenic agents, growth factors, oligonucleotides, hormones, peptides, toxins, pro-apoptotic agents, or a combination thereof. Any of the techniques known in the art for making bispecific or multispecific antibodies may be utilized in the practice of the presently claimed methods.

Bispecific or multispecific antibodies may incorporate any known antibody of therapeutic use. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226;

6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Figures and Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Dock-and-Lock (DNL)

In preferred embodiments, bispecific or multispecific antibodies or other constructs may be produced using the dock-and-lock technology (see, e.g., U.S. Pat. Nos. 7,521,056; 7,550,143; 7,534,866; 7,527,787 and U.S. patent application Ser. No. 11/925,408, filed Oct. 26, 2007, and Ser. No. 12/418,877, filed Apr. 6, 2009; the Examples section of each of which is incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). Interestingly, AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize DDD (for example, SEQ ID NO:15 and SEQ ID NO:16) and AD (for example, SEQ ID NO:17 and SEQ ID NO:18) sequences as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically.

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized to link other types of molecules together.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, 2$^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

DNL Sequence Variants

In alternative embodiments, sequence variants of the AD and/or DDD moieties may be utilized in construction of the DNL complexes. The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400:493-99; Gold et al., 2006, Mol Cell 24:383-95; Kinderman et al., 2006, Mol Cell 24:397-408.)

For example, Kinderman et al. (2006) examined the crystal structure of the AD-DDD binding interaction and concluded that the human DDD sequence contained a number of conserved amino acid residues that were important in either dimer formation or AKAP binding, underlined in SEQ ID NO:15 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

Human DDD Sequence from Protein Kinase A
SHIQIPPGLTELLQGYTVEVLRQQPPDLVEFAVEYFTR LREARA (SEQ ID NO:15)

Alto et al. (2003) performed a bioinformatic analysis of the AD sequence of various AKAP proteins to design an RH selective AD sequence called AKAP-IS (SEQ ID NO:17), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:17.

AKAP-IS Sequence
QIEYLAKQIVDNAIQQA (SEQ ID NO:17)

Similarly, Gold (2006) utilized crystallography and peptide screening to develop a SuperAKAP-IS sequence (SEQ ID NO:39), exhibiting a five order of magnitude higher selectivity for the RII isoform of PKA compared with the RI isoform. Underlined residues indicate the positions of amino acid substitutions, relative to the AKAP-IS sequence, that increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:40-42. Substitutions relative to the AKAP-IS sequence are underlined. It is anticipated that, as with the AKAP-IS sequence (SEQ ID NO:17), the AD moiety may also include the additional N-terminal residues cysteine and glycine and C-terminal residues glycine and cysteine, as shown in SEQ ID NO:18.

```
SuperAKAP-IS
                                    (SEQ ID NO: 39)
QIEYVAKQIVDYAIHQA Alternative AKAP sequences
                                    (SEQ ID NO: 40)
QIEYKAKQIVDHAIHQA (SEQ ID NO: 41)
QIEYHAKQIVDHAIHQA (SEQ ID NO: 42)
QIEYVAKQIVDHAIHQA
```

Stokka et al. (2006) also developed peptide competitors of AKAP binding to PKA, shown in SEQ ID NO:43-45. The peptide antagonists were designated as Ht31 (SEQ ID NO:43), RIAD (SEQ ID NO:44) and PV-38 (SEQ ID NO:45). The Ht-31 peptide exhibited a greater affinity for the RH isoform of PKA, while the RIAD and PV-38 showed higher affinity for RI.

```
Ht31
                                    (SEQ ID NO: 43)
DLIEEAASRIVDAVIEQVKAAGAY

RIAD
                                    (SEQ ID NO: 44)
LEQYANQLADQIIKEATE

PV-38
                                    (SEQ ID NO: 45)
FEELAWKIAKMIWSDVFQQC
```

Hundsrucker et al. (2006) developed still other peptide competitors for AKAP binding to PKA, with a binding constant as low as 0.4 nM to the DDD of the RII form of PKA. The sequences of various AKAP antagonistic peptides is provided in Table 1 of Hundsrucker et al. (incorporated herein by reference). Residues that were highly conserved among the AD domains of different AKAP proteins are indicated below by underlining with reference to the AKAP IS sequence. The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence are shown in SEQ ID NO:46-48.

```
AKAP-IS
                                    (SEQ ID NO: 17)
QIEYLAKQIVDNAIQQA

AKAP7δ-wt-pep
                                    (SEQ ID NO: 46)
PEDAELVRLSKRLVENAVLKAVQQY AKAP7δ-L304T-pep
                                    (SEQ ID NO: 47)
PEDAELVRTSKRLVENAVLKAVQQY AKAP7δ-L308D-pep
                                    (SEQ ID NO: 48)
PEDAELVRLSKRDVENAVLKAVQQY
```

Carr et al. (2001) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:15. Residues that were particularly conserved are further indicated by italics. The residues overlap with, but are not identical to those suggested by Kinderman et al. (2006) to be important for binding to AKAP proteins.

(SEQ ID NO: 15)
SH*IQI*PP*GLT*ELLQGY*TV*EVLRQQPP*DLV*EFAVE*YF*TRLR*EA*RA

The skilled artisan will realize that in general, those amino acid residues that are highly conserved in the DDD and AD sequences from different proteins are ones that it may be preferred to remain constant in making amino acid substitutions, while residues that are less highly conserved may be more easily varied to produce sequence variants of the AD and/or DDD sequences described herein.

scFv-Based AD Modules

Alternative embodiments may concern the use of scFV-based AD modules for pairing with DDD2 (SEQ ID NO:16) based cytokines or RNase to yield DNL conjugates that are smaller. The smaller sized DNL constructs may facilitate penetration into solid tumors. We have produced several types of scFv-based bispecific antibodies by expressing two discrete polypeptide chains comprising complementary variable domains with a 6-His tag (SEQ ID NO: 51) at the carboxyl terminus of each polypeptide chain. The same approach may be used to generate scFv-based AD modules by replacing one or both 6-His tags (SEQ ID NO: 51) with either an AD sequence or an AD-HHHHHH sequence (SEQ ID NO: 51). We can also fuse each polypeptide chain with a different AD sequence (e.g. AD2 (SEQ ID NO:18) and AD3 (SEQ ID NO:49)), which would allow the specific recognition by its cognate DDD sequence, thus providing further complexity of the final DNL conjugates. Table 1 below provides a non-exhaustive list of such scFv-based DNL constructs.

TABLE 1 scFv-based DNL constructs

| Configuration | | ScFv-AD | MW (kDa) | Note |
|---|---|---|---|---|
| BS2 | I | VH$_1$-VL$_2$-AD2 | 30 | Bispecific, 1 × 1 |
| | | VH$_2$-VL$_1$ | 25 | |
| | II | VH$_1$-VL$_2$-AD2 | 30 | |
| | | VH$_2$-VL$_1$-AD2 | 30 | |
| | III | VH$_1$-VL$_2$-AD2 | 30 | |
| | | VH$_2$-VL$_1$-AD3 | 30 | |
| "DVD" | I | VH$_1$-VH$_2$-AD2 | 30 | Bispecific, 1 × 1 |
| | | VL$_1$-VL$_2$ | 25 | |
| | II | VH$_1$-VH$_2$-AD2 | 30 | |
| | | VL$_2$-VL$_1$-AD2 | 30 | |
| | III | VH$_1$-VH$_2$-AD2 | 30 | |
| | | VL$_2$-VL$_1$-AD3 | 30 | |
| BS6 | I | VH$_1$-VL$_1$-VH$_2$-AD2 | 45 | Bispecific, 2 × 1 |
| | | VL$_2$-VH$_1$-VL$_1$ | 40 | |
| | II | VH$_1$-VL$_1$-VH$_2$-AD2 | 45 | |
| | | VL$_2$-VH$_1$-VL$_1$-AD2 | 45 | |
| | III | VH$_1$-VL$_1$-VH$_2$-AD2 | 45 | |
| | | VL$_2$-VH$_1$-VL$_1$-AD3 | | |
| BS8 | I | VH$_1$-VH$_1$-VH$_2$-AD2 | 45 | Bispecific, 2 × 1 |
| | | VL$_2$-VL$_1$-VL$_1$ | 40 | |
| | II | VH$_1$-VH$_1$-VH$_2$-AD2 | 45 | |
| | | VL$_2$-VL$_1$-VL$_1$-AD2 | 45 | |

TABLE 1-continued scFv-based DNL constructs

| Configuration | | ScFv-AD | MW (kDa) | Note |
|---|---|---|---|---|
| | III | VH$_1$-VH$_1$-VH$_2$-AD2 | 45 | |
| | | VL$_2$-VL$_1$-VL$_1$-AD3 | 45 | |
| BS18 | I | VH$_1$-CH$_1$-VH$_2$-AD2 | 55 | |
| | | VL$_1$-CL-VL$_2$ | 50 | |
| | II | VH$_1$-CH$_1$-VH$_2$-AD2 | 55 | |
| | | VL$_1$-CL-VL$_2$-AD2 | 55 | |
| | III | VH$_1$-CH$_1$-VH$_2$-AD2 | 55 | |
| | | VL$_1$-CL-VL$_2$-AD3 | 55 | |
| TS | I | VH$_1$-VH$_2$-VH$_3$-AD2 | 45 | Trispecific, 1 × 1 × 1 |
| | | VL$_3$-VL$_2$-VL$_1$ | 40 | |
| | II | VH$_1$-VH$_2$-VH$_3$-AD2 | 45 | |
| | | VL$_3$-VL$_2$-VL$_1$-AD2 | 45 | |
| | III | VH$_1$-VH$_2$-VH$_3$-AD2 | 45 | |
| | | VL$_3$-VL$_2$-VL$_1$-AD3 | 45 | |

Type I is designed to link one pair of DDD2 (SEQ ID NO:16) modules. Type II is designed to link two pairs of the same or different DDD2 modules. Type III is designed to link one pair of DDD2 modules and one pair of DDD3 (SEQ ID NO:50) modules. The two polypeptides chains are designed to associate in an anti-parallel fashion.

Pre-Targeting

Bispecific or multispecific antibodies may be utilized in pre-targeting techniques. Pre-targeting is a multistep process originally developed to resolve the slow blood clearance of directly targeting antibodies, which contributes to undesirable toxicity to normal tissues such as bone marrow. With pre-targeting, a radionuclide or other therapeutic agent is attached to a small delivery molecule (targetable construct or targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med. 30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256, 395; Stickney et al., Cancer Res. 51:6650, 1991; Yuan et al., Cancer Res. 51:3119, 1991; U.S. Pat. Nos. 6,077,499; 7,011, 812; 7,300,644; 7,074,405; 6,962,702; 7,387,772; 7,052, 872; 7,138,103; 6,090,381; 6,472,511; 6,962,702; 6,962, 702; 7,074,405; and U.S. Ser. No. 10/114,315 (now abandoned); the Examples section of each of which is incorporated herein by reference.

A pre-targeting method of treating or diagnosing a disease or disorder in a subject may be provided by: (1) administering to the subject a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents. The technique may also be utilized for antibody dependent enzyme prodrug therapy (ADEPT) by administering an enzyme conjugated to a targetable construct, followed by a prodrug that is converted into active form by the enzyme.

Avimers

In certain embodiments, the binding moieties described herein may comprise one or more avimer sequences. Avimers are a class of binding proteins somewhat similar to antibodies in their affinities and specificities for various target molecules. They were developed from human extracellular receptor domains by in vitro exon shuffling and phage display. (Silverman et al., 2005, Nat. Biotechnol. 23:1493-94; Silverman et al., 2006, Nat. Biotechnol. 24:220.) The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756 (now abandoned), 20050048512 (now abandoned), 20050053973 (now abandoned), 20050089932 and 20050221384 (now abandoned), the Examples section of each of which is incorporated herein by reference.

Phage Display

Certain embodiments of the claimed compositions and/or methods may concern binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257). In addition to peptides, larger protein domains such as single-chain antibodies may also be displayed on the surface of phage particles (Arap et al., 1998, Science 279:377-380).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In certain embodiments, a targeting moiety of use may be an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. No. 5,475,096 and U.S. Pat. No. 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S. Not all linkages in an oligomer need to be identical.

Therapeutic and Diagnostic Agents

In certain embodiments, the antibodies, antibody fragments or fusion proteins described herein may be administered alone, as a "naked" antibody, fragment or fusion protein. In alternative embodiments, the antibody, fragment or fusion protein may be administered either before, concurrently with, or after at least one other therapeutic agent. In other alternatives, an antibody, fragment or fusion protein may be covalently or non-covalently attached to at least one therapeutic and/or diagnostic agent to form an immunoconjugate.

Therapeutic agent are preferably selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a cytotoxic agent, which may be a chemotherapeutic agent or a toxin, and a combination thereof. The drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use include, but are not limited to, 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epidophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, taxol, temazolomide (an aqueous form of DTIC), transplatinum, thalidomide, thioguanine, thiotepa, teniposide, topotecan, uracil mustard, vinorelbine, vinblastine, vincristine and vinca alkaloids.

Toxins of use may include ricin, abrin, alpha toxin, saporin, ribonuclease (RNase), e.g., onconase, DNase I, *Staphylococcal* enterotoxin-A, pokeweed antiviral protein, gelonin, diphtheria toxin, *Pseudomonas* exotoxin, and *Pseudomonas* endotoxin.

Immunomodulators of use may be selected from a cytokine, a stem cell growth factor, a lymphotoxin, an hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -γ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rb, $^{142}$Pr, $^{143}$Pr, $^{161}$Tb, $^{166}$Ho, $^{199}$Ab, $^{57}$Co, $^{58}$Co, $^{51}$Cr, $^{59}$Fe, $^{75}$Fe, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$CU, $^{67}$Ga, $^{68}$Ga, $^{86}$Y, $^{89}$Zr, $^{94}$Tc, $^{94m}$Tc, $^{99m}$Tc, or $^{111}$In. In certain embodiments, anti-IGF-1R antibodies, such as hR1, may be of use in combination with therapeutic radionuclides for sensitization of tumors to radiation therapy (see, e.g., Allen et al., 2007, Cancer Res. 67:1155).

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., J. Immunol. (1983), 130:1473; idem., Cancer Res. (1985), 45:4380; Oseroff et al., Proc. Natl. Acad. Sci. USA (1986), 83:8744; idem., Photochem. Photobiol. (1987), 46:83; Hasan et al., Prog. Clin. Biol. Res. (1989), 288:471; Tatsuta et al., Lasers Surg. Med. (1989), 9:422; Pelegrin et al., Cancer (1991), 67:2529.

Corticosteroid hormones can increase the effectiveness of other chemotherapy agents, and consequently, they are frequently used in combination treatments. Prednisone and dexamethasone are examples of corticosteroid hormones.

In certain embodiments, anti-angiogenic agents, such as angiostatin, baculostatin, canstatin, maspin, anti-placenta growth factor (PlGF) peptides and antibodies, anti-vascular growth factor antibodies (such as anti-VEGF and anti-PlGF), anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Other useful therapeutic agents comprise oligonucleotides, especially antisense oligonucleotides that preferably are directed against oncogenes and oncogene products, such as bcl-2.

Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Immunoconjugates

Any of the antibodies, antibody fragments or antibody fusion proteins described herein may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

In some embodiments, a chelating agent may be attached to an antibody, antibody fragment or fusion protein or to a targetable construct and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MRI. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F—Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

Methods of Therapeutic Treatment

Various embodiments concern methods of treating a cancer in a subject, such as a mammal, including humans, domestic or companion pets, such as dogs and cats, comprising administering to the subject a therapeutically effective amount of an antibody, fragment or fusion protein. In preferred embodiments, the antibody or fragment is an anti-IGF-1R MAb. In certain embodiments, the therapy may utilize a "naked antibody" that does not have a therapeutic agent bound to it.

The administration of a "naked" anti-IGF-1R antibody can be supplemented by administering concurrently or sequentially a therapeutically effective amount of another "naked antibody" that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof.

The naked anti-IGF-1R therapy alone or in combination with other naked MAbs can be further supplemented with the administration, either concurrently or sequentially, of at least one therapeutic agent, as discussed above. Multimodal therapies may include therapy with naked anti-IGF-1R antibodies supplemented with administration of anti-CD22, anti-CD19, anti-CD20, anti-CD21, anti-CD74, anti-CD80, anti-CD23, anti-CD45, anti-CD46, anti-MIF, anti-EGP-1, anti-CEACAM5, anti-CEACAM6, PAM4, or anti-HLA-DR (including the invariant chain) antibodies in the form of naked antibodies, fusion proteins, or as immunoconjugates. The naked anti-IGF-1R antibodies or fragments thereof may also be supplemented with naked antibodies against a MUC1 or MUC5 antigen. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498 and U.S. Patent Application Publ. Nos. 20080131363; 20080089838; 20070172920; 20060193865; and 20080138333; the Examples section of each of which is incorporated herein by reference.

In another form of multimodal therapy, subjects receive naked anti-IGF-1R antibodies, and/or immunoconjugates, in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1. In a preferred multimodal therapy, both chemotherapeutic drugs and cytokines are co-administered with an antibody, immunoconjugate or fusion protein according to the present invention. The cytokines, chemotherapeutic drugs and antibody or immunoconjugate can be administered in any order, or together.

Immunoconjugates or naked antibodies can be formulated according to known methods to prepare pharmaceutically useful compositions, whereby the immunoconjugate or naked antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate or naked antibody of the present invention can be formulated for intravenous administration via, for example, bolus injection or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic conjugate or naked antibody. Control release preparations can be prepared through the use of polymers to complex or adsorb the immunoconjugate or naked antibody. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The immunoconjugate, antibody fusion proteins, or naked antibody may also be administered to a mammal subcutaneously or even by other parenteral routes. Moreover, the administration may be by continuous infusion or by single or multiple boluses. Preferably, the antibody is infused over a period of less than about 4 hours, and more preferably, over a period of less than about 3 hours.

More generally, the dosage of an administered immunoconjugate, fusion protein or naked antibody for humans will vary depending upon such factors as the patient's age, weight, height, sex, general medical condition and previous medical history. It may be desirable to provide the recipient with a dosage of immunoconjugate, antibody fusion protein or naked antibody that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, an antibody such as a naked anti-IGF-1R, may be administered as one dosage every 2 or 3 weeks, repeated for a total of at least 3 dosages. Or, the antibodies may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the anti-IGF-1R antibodies are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)). Such conditions in which cells begin to express, overexpress, or abnormally express IGF-1R, are particularly treatable by the disclosed methods and compositions.

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Kits

Various embodiments may concern kits containing components suitable for treating or diagnosing diseased tissue in a patient. Exemplary kits may contain at least one antibody, fragment or fusion protein as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

Expression Vectors

Still other embodiments may concern DNA sequences comprising a nucleic acid encoding an antibody, fragment, fusion protein or bispecific antibody. Exemplary sequences that may be encoded and expressed include an anti-IGF-1R MAb or fragment thereof, a fusion protein comprising at least one anti-IGF-1R antibody or fragment thereof, a fusion protein comprising at least one first antibody or fragment and at least one second antibody or fragment. The first and second antibodies may comprise an anti-IGF-1R antibody, an antibody against a tumor associated antigen and/or a hapten on a targetable construct. Fusion proteins may comprise an antibody or antibody fragment attached to a different peptide or protein, such as the AD and DDD peptides utilized for DNL construct formation as discussed in more detail in the Examples below.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express MAbs in a selected host cell, immunoglobulin enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969). In other embodiments, an IgG1 sequence may be converted to an IgG4 sequence as discussed below.

Also encompassed is a method of expressing antibodies or fragments thereof or fusion proteins. The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327; 7,537,930; and 7,608,425, the Examples section of each of which is incorporated herein by reference.

General Techniques for Construction of Anti-IGF-1R Antibodies

The Vκ (variable light chain) and $V_H$ (variable heavy chain) sequences for anti-IGF-1R antibodies may be obtained by a variety of molecular cloning procedures, such as RT-PCR, 5'-RACE, and cDNA library screening. The V genes of an anti-IGF-1R MAb from a cell that expresses a murine anti-IGF-1R MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA,* 86: 3833 (1989)). Based on the V gene sequences, a humanized anti-IGF-1R MAb can then be designed and constructed as described by Leung et al. (*Mol. Immunol.,* 32: 1413 (1995)).

cDNA can be prepared from any known hybridoma line or transfected cell line producing a murine anti-IGF-1R MAb by general molecular cloning techniques (Sambrook et al., Molecular Cloning, A laboratory manual, $2^{nd}$ Ed (1989)). The Vκ sequence for the MAb may be amplified using the primers VK1BACK and VK1FOR (Orlandi et al., 1989) or the extended primer set described by Leung et al. (*BioTechniques,* 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)).

PCR reaction mixtures containing 10 µl of the first strand cDNA product, 10 µl of 10×PCR buffer [500 mM KCl, 100 mM Tris-HCl (pH 8.3), 15 mM $MgCl_2$, and 0.01% (w/v) gelatin] (Perkin Elmer Cetus, Norwalk, Conn.), 250 µM of each dNTP, 200 nM of the primers, and 5 units of Taq DNA polymerase (Perkin Elmer Cetus) can be subjected to 30 cycles of PCR. Each PCR cycle preferably consists of denaturation at 94° C. for 1 min, annealing at 50° C. for 1.5 min, and polymerization at 72° C. for 1.5 min. Amplified Vκ and VH fragments can be purified on 2% agarose (BioRad, Richmond, Calif.). The humanized V genes can be constructed by a combination of long oligonucleotide template syntheses and PCR amplification as described by Leung et al. (*Mol. Immunol.,* 32: 1413 (1995)).

PCR products for Vκ can be subcloned into a staging vector, such as a pBR327-based staging vector, VKpBR, that contains an Ig promoter, a signal peptide sequence and convenient restriction sites to facilitate in-frame ligation of the Vκ PCR products. PCR products for $V_H$ can be subcloned into a similar staging vector, such as the pBluescript-based VHpBS. Individual clones containing the respective PCR products may be sequenced by, for example, the method of Sanger et al. (*Proc. Natl. Acad. Sci., USA,* 74: 5463 (1977)).

Expression cassettes containing the Vκ and $V_H$ sequences, together with the promoter and signal peptide sequences, can be excised from VKpBR and VHpBS, respectively, by double restriction digestion as HindIII-BamHI fragments. The Vκ and $V_H$ expression cassettes can be ligated into appropriate expression vectors, such as pKh and pG1g, respectively (Leung et al., Hybridoma, 13:469 (1994)). The expression vectors can be co-transfected into an appropriate cell, e.g., myeloma Sp2/0-Ag14 (ATCC, VA), colonies selected for hygromycin resistance, and supernatant fluids monitored for production of a chimeric, humanized or human anti-IGF-1R MAb by, for example, an ELISA assay. Alternatively, the Vκ and $V_H$ expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gillies et al. (*J. Immunol. Methods* 125:191 (1989) and also shown in Losman et al., *Cancer,* 80:2660 (1997)). Another vector that is useful is the GS vector, as described in Barnes et al., *Cytotechnology* 32:109-123 (2000). Other appropriate mammalian expression systems are described in Werner et al., Arzneim.-Forsch./Drug Res. 48(II), Nr. 8, 870-880 (1998).

Co-transfection and assay for antibody secreting clones by ELISA, can be carried out as follows. About 10 µg of VKpKh (light chain expression vector) and 20 µg of VHpG1g (heavy chain expression vector) can be used for the transfection of $5×10^6$ SP2/0 myeloma cells by electroporation (BioRad, Richmond, Calif.) according to Co et al., *J. Immunol.,* 148: 1149 (1992). Following transfection, cells may be grown in 96-well microtiter plates in complete HSFM medium (Life Technologies, Inc., Grand Island, N.Y.) at 37° C., 5% $CO_2$. The selection process can be initiated after two days by the addition of hygromycin selection medium (Calbiochem, San Diego, Calif.) at a final concentration of 500 units/ml of hygromycin. Colonies typically emerge 2-3 weeks post-electroporation. The cultures can then be expanded for further analysis. Transfectoma clones that are positive for the secretion of chimeric, humanized or human heavy chain can be identified by ELISA assay.

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2μ membrane. The filtered medium is passed through a protein A column (1×3 cm) at a flow rate of 1 ml/min. The resin is then washed with about 10 column volumes of PBS and protein A-bound antibody is eluted from the column with 0.1 M citrate buffer (pH 3.5) containing 10 mM EDTA. Fractions of 1.0 ml are collected in tubes containing 10 μl of 3 M Tris (pH 8.6), and protein concentrations determined from the absorbance at 280/260 nm. Peak fractions are pooled, dialyzed against PBS, and the antibody concentrated, for example, with the Centricon 30 (Amicon, Beverly, Mass.). The antibody concentration is determined by absorbance at 280 nm and its concentration adjusted to about 1 mg/ml using PBS. Sodium azide, 0.01% (w/v), is conveniently added to the sample as preservative.

EXAMPLES

Example 1. Generation and Initial Characterization of Anti-IGF-1R Antibodies: R1, cR1, and hR1

Three BALB/c mice were each immunized i.p. with 15 μg of recombinant human IGF-1R (R&D Systems, Catalog #391-GR), comprising a mixture of both processed and unprocessed extracellular domain of human IGF-1R, in complete Freund's adjuvant. Additional immunizations in incomplete Freund's adjuvant were done 14, 21, and 28 days after the initial immunization. Spleen cells from the immunized mice were fused with P3X63Ag8.653 cells to generate hybridomas according to standard protocols. One clone (C-11) expressing anti-IGF-1R but not anti-IR (insulin receptor) activity was isolated and expanded in cultures to obtain the mouse antibody designated ML04R1 or R1, which was shown to be an IgG1/k with the ability to inhibit the binding of radioiodinated IGF-1 to the IGF-1R expressing human breast cancer cell line MCF-7L (a subline of MCF-7) comparable to a commercially available mouse anti-IGF-1R monoclonal antibody (mAb) MAB391 (Table 2).

TABLE 2

Binding of $^{125}$I-IGF-1 to MCF-7L in the presence of MAB391 or R1

| [Ab] | MAB391[a] | R1 |
|---|---|---|
| 1000 ng/mL | 38% | 58% |
| 100 ng/mL | 54% | 71% |
| 10 ng/mL | 95% | 97% |
| 0 ng/mL | 100% | 100% |

[a]R&D clone 33255.111

To obtain cR1, the mouse-human chimeric mAb of R1, the $V_H$ and $V_K$ genes of R1 were cloned by 5'-RACE. The authenticity of the cloned $V_H$ and $V_K$ genes was confirmed by N-terminal protein sequencing that showed an exact match of the first 15 N-terminal amino acids with the corresponding amino acids deduced from DNA sequences (Table 3). The cloned $V_H$ and $V_K$ genes were inserted into the pdHL2 vector to generate cR1pdHL2 (FIG. 1), the expression vector for cR1.

TABLE 3

N-terminal protein sequencing of R1

| Cycle/position | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| (H + L)[a] | | D/E | I/V | K/V | L/M | T/V | E/Q | S | G/H | G/K | F/G | L/M | S/V | Q/T | P/S | G/V |
| $V_H$[b] (SEQ ID NO: 52) | E | V | K | L | V | E | S | G | G | G | L | V | Q | P | G |
| $V_K$[b] (SEQ ID NO: 53) | D | I | V | M | T | Q | S | H | K | F | M | S | T | S | V |

Figure 2:
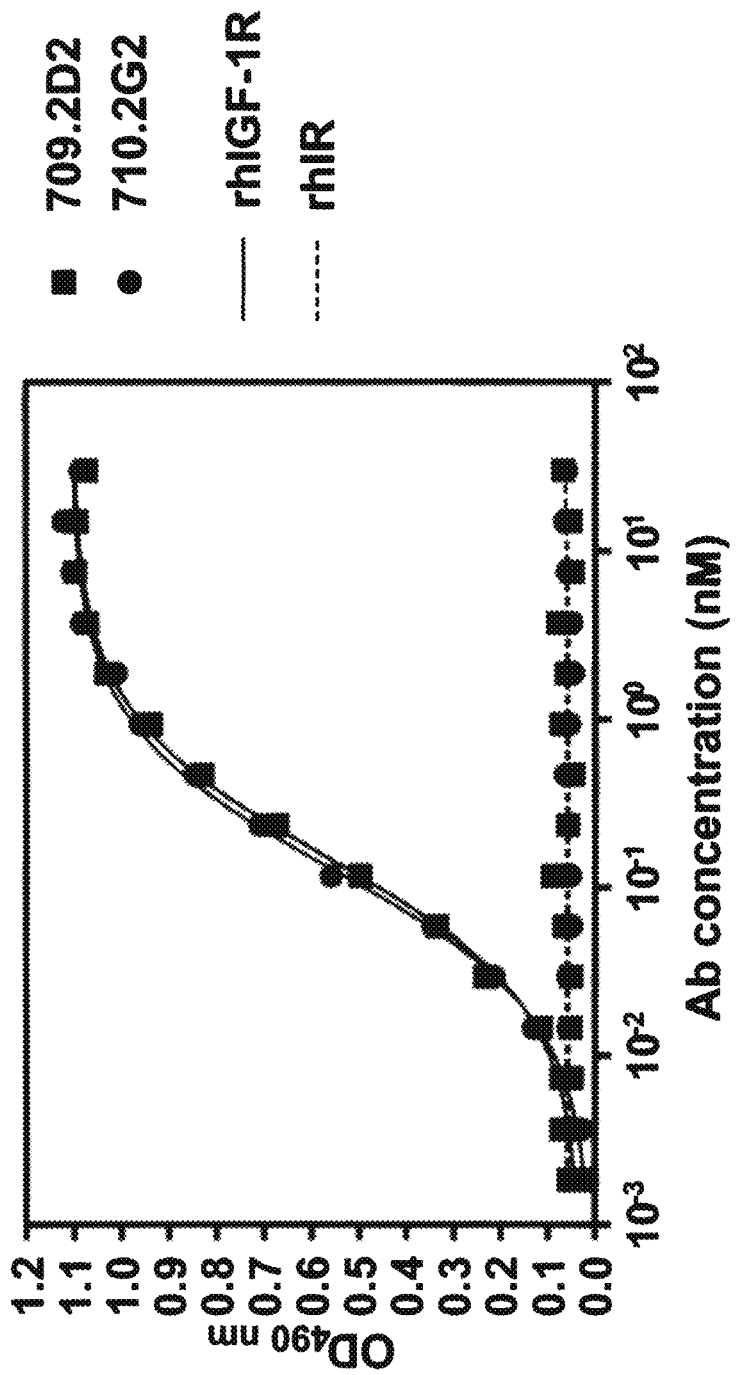
FIG. 2. Binding specificity of chimeric R1 (cR1) antibodies to immobilized recombinant human IGF-1R and recombinant human IR. The cR1 was obtained from two different clones—709.2D2 and 710.2G2. The cR1 antibodies bind to human IGF-1R but not to the human insulin receptor (IR).
Figure 3:
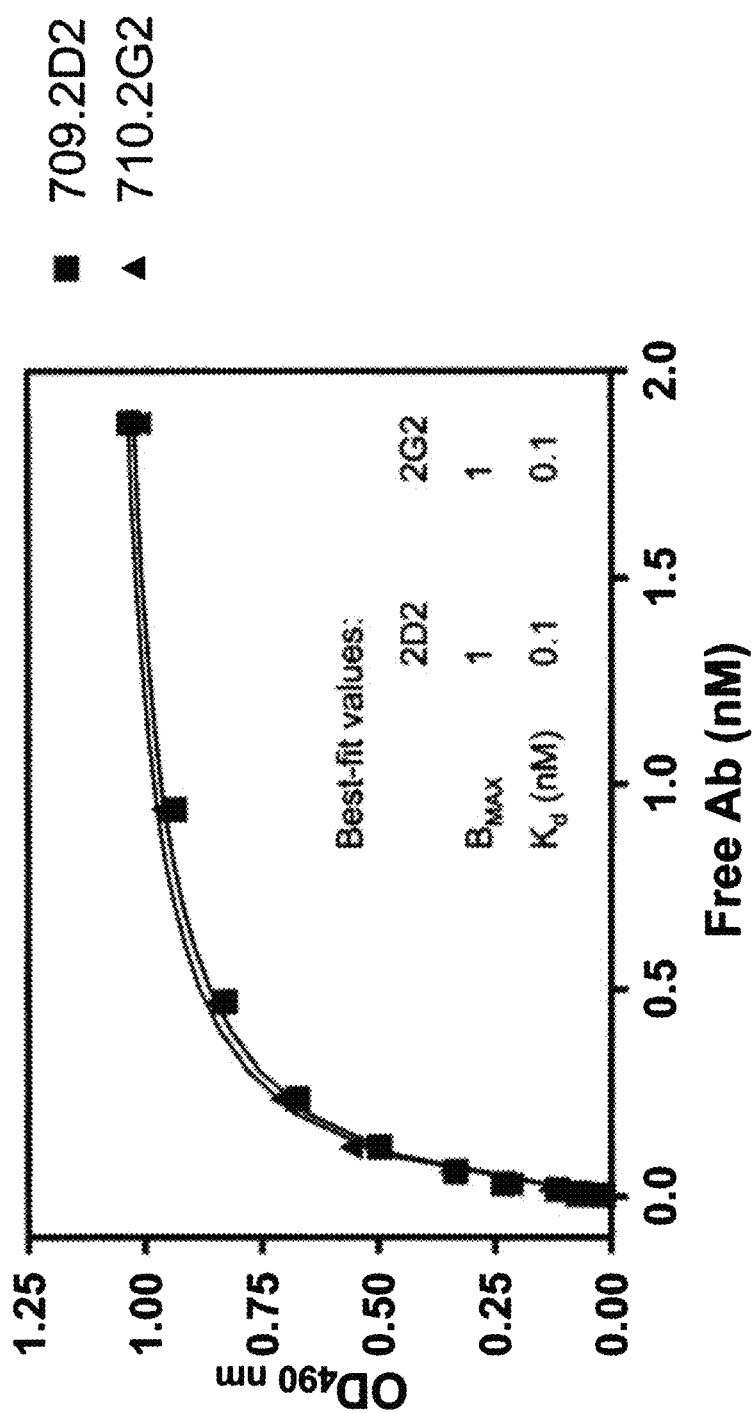
FIG. 3. Binding affinity of cR1 to immobilized recombinant human IGF-1R.
Figure 4:
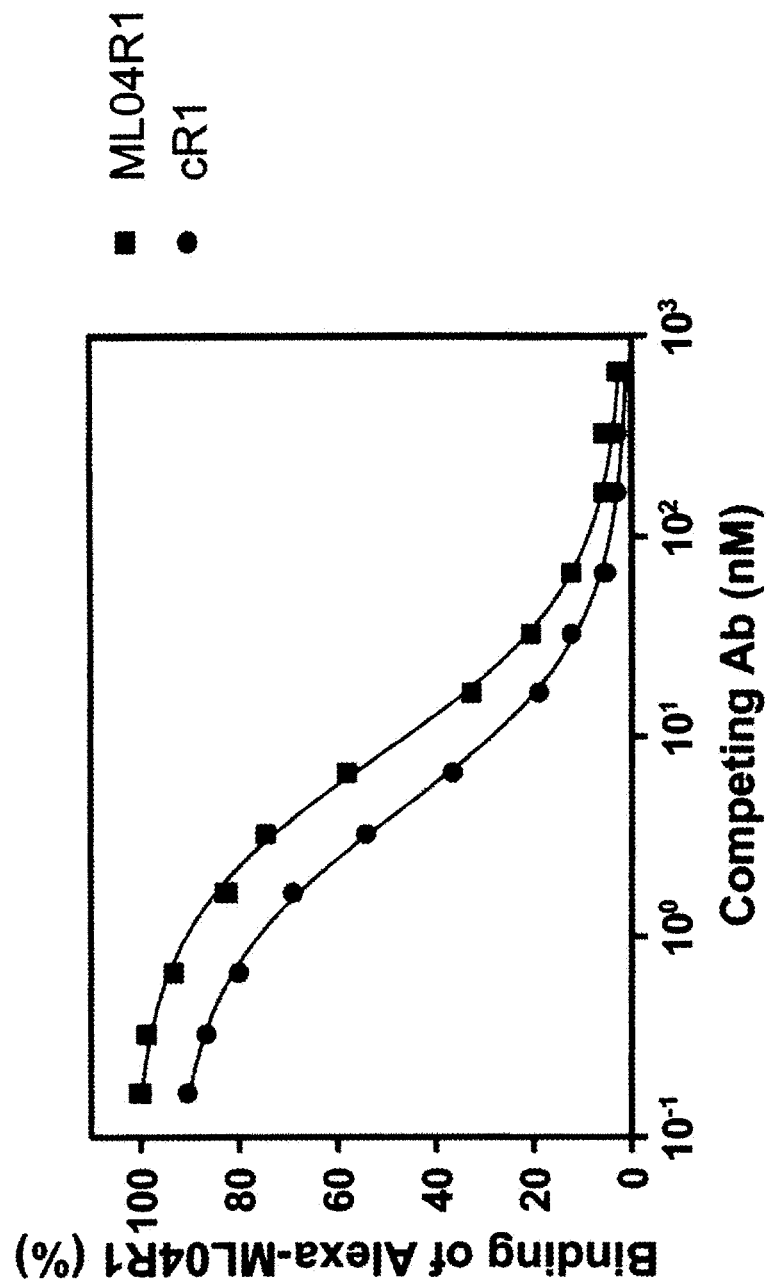
FIG. 4. Competitive binding of murine R1 (ML04R1) and chimeric R1 (cR1) antibodies to immobilized recombinant human IGF-1R.

[a]Purified R1 was subjected to N-terminal protein sequencing (15 cycles). Two residues were detected after each cycle of Edman degradation.
[b]Deduced from the DNA sequences.

cR1-producing clones were generated using SpE-26 (e.g., U.S. Pat. No. 7,531,327), a variant of Sp2/0-Ag14 that shows improved growth properties, as host cells. Briefly, approximately 30 μg of cR1pdHL2 was linearized by digestion with SalI restriction endonuclease and transfected into SpE-26 cells by electroporation. The transfectants were selected with 0.075 μM methotrexate (MTX), and screened by ELISA for human Fc binding activities. The higher producing clones were further expanded to pick the two best clones (709.2D2 and 710.2G2), from which cR1 was produced in batch cultures, purified by Protein A, and each confirmed by ELISA to bind specifically to immobilized rhIGF-1R, but not to immobilized rhIR, as shown in FIG. 2, with the same high affinity ($K_D$~0.1 nM) for immobilized rhIGF-1R, as shown in FIG. 3. Surprisingly, cR1 appears to have a higher affinity than R1 for rhIGF-1R immobilized onto polystyrene beads as shown by a competition assay in which the binding of R1 tagged with a fluorescent probe was measured by flow cytometry in the presence of varying concentrations of cR1 or R1 (FIG. 4).

Figure 5:
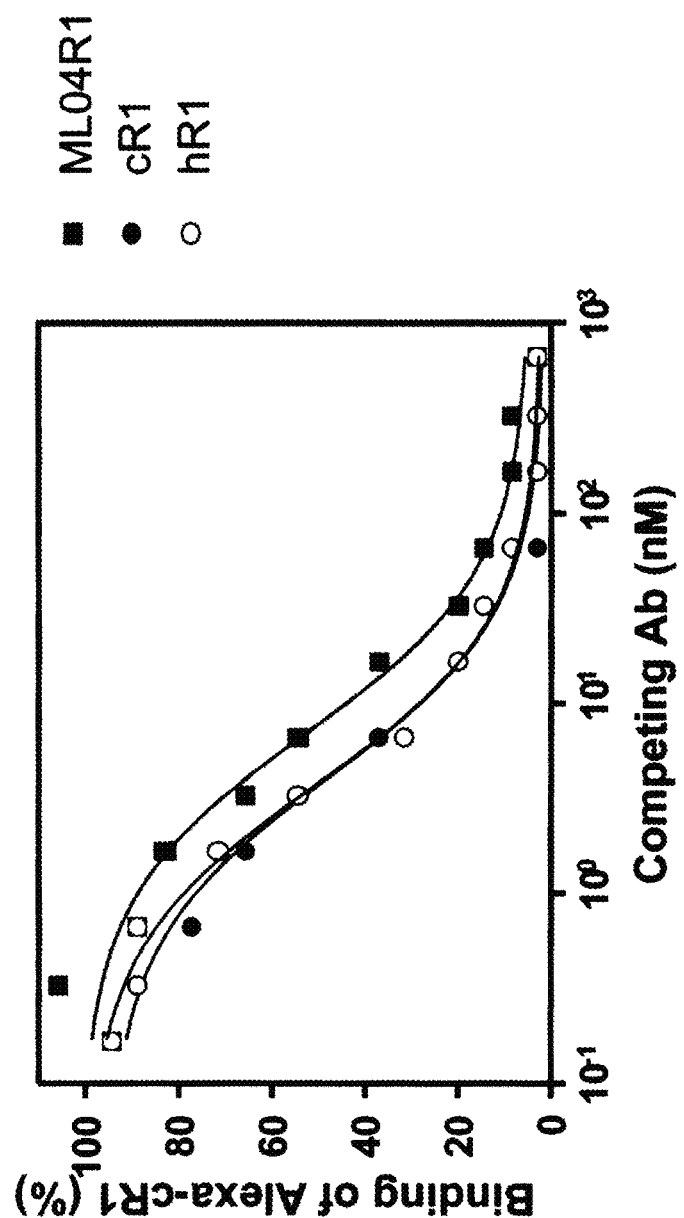
FIG. 5. Comparison of binding of humanized R1 (hR1), chimeric R1 (cR1) and murine R1 (ML04R1) antibodies to immobilized recombinant human IF-1R.

Successful humanization of cR1 to hR1 was achieved by grafting the CDRs onto the human framework regions of hMN-14 (U.S. Pat. Nos. 5,874,540 and 6,676,924, the Examples section of each incorporated herein by reference) in which certain human framework residues were replaced with murine counterparts of R1 at corresponding positions. Other selected residues were substituted for cloning purposes, resulting in the amino acid sequences of hR1 $V_H$ and hR1 $V_K$ as shown in SEQ ID NO:9 and SEQ ID NO:10, respectively. Genes encoding hR1 $V_H$ and hR1 Vk were then synthesized and engineered into pdHL2 to obtain hR1pdHL2, the expression vector for hR1. Subsequent efforts to secure the production clone (711.3C11) for hR1 were similar to those describe above for cR1. Positive clones were selected for binding activity to rhIGF-1R. As shown in FIG. 5, hR1 displayed virtually the same binding affinity as cR1 for rhIGF-1R immobilized on polystyrene beads.

Figure 6:
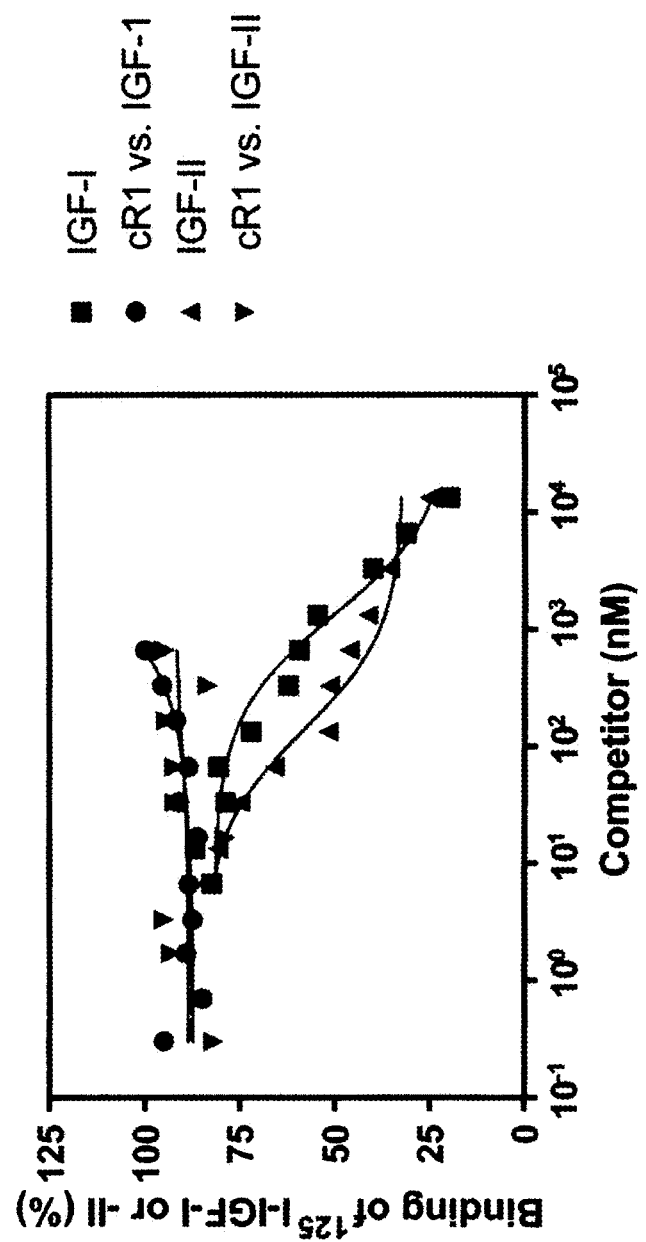
FIG. 6. Chimeric R1 (cR1) does not block binding of IGF-1 or IGF-2 to immobilized recombinant human IGF-1R. $^{125}$I-labeled IGF-1 or IGF-2 was incubated with unlabeled IGF-1, IGF-2 or cR1.
Figure 7:
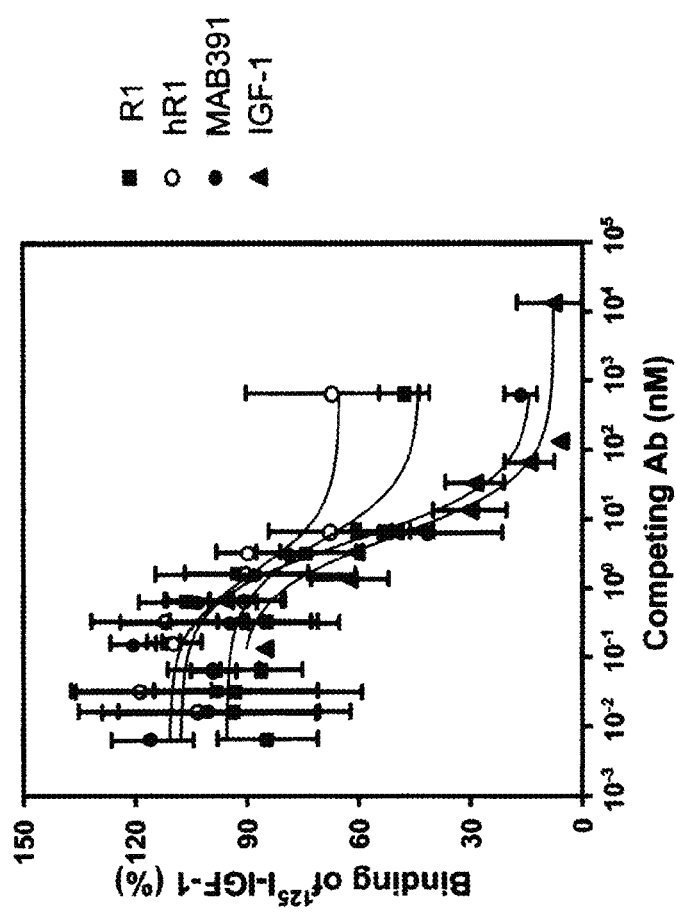
FIG. 7. Humanized R1 (hR1) and murine R1 do not block binding of IGF-1 to immobilized recombinant human IGF-1R. $^{125}$I-labeled IGF-1 was incubated with unlabeled IGF-1, MAb391, hR1 or R1.

To determine whether cR1 can block the binding of IGF-1 or IGF-2 to IGF-1R, we used polystyrene beads immobilized with rhIGF-1R as surrogates of cells expressing IGF-1R and performed the beads-competition assays as follows. Briefly, varying concentrations (0 to 670 nM) of cR1, IGF-1, or IGF-2 were mixed with a constant amount of $^{125}$I-IGF-1 or $^{125}$I-IGF-2. The rhIGF-1-coated beads were then added, incubated at room temperature for 1 h with gentle rocking, washed, and counted for radioactivity. The results shown in FIG. 6 indicate that cR1 failed to block the binding of either IGF-1 or IGF-2 to such immobilized rhIGF-1R under these conditions. The results of a similar experiment shown in FIG. 7 also indicate that binding of $^{125}$I-IGF-1 to the bead-immobilized IGF-1R was effectively blocked by IGF-1 or MAB391, but not by hR1 or R1. These findings suggest IGF-1 and MAB391 bind to the same epitope, or have overlapping epitopes of IGF-1R, and hR1 targets a different region of IGF-1R from MAB391 or IGF-1. As the primary binding site of IGF-1R for IGF-1 was reported to be located in the cysteine-rich (CR) domain between amino acids (aa) 223 and 274, and the same region (aa 223-274) has been assigned as the epitope to αIR-3, which like MAB391, competes for IGF-1 binding (Gustafson T A, Rutter W J. J Biol Chem 1990; 265:18663-7), it appeared that MAB391 also binds to the same region or interacts with sites in close proximity.

Example 2. Epitope Mapping Studies of R1, cR1, and hR1

To further locate the region of IGF-1R to which hR1 binds, a panel of commercially available anti-IGF-1R mAbs that have their epitopes to IGF-1R mapped, were evaluated for their ability to cross-block each other from binding to the IGF-1R-coated beads. The results of two typical experiments are provided in FIG. 8A, which shows the binding of R1 tagged with a fluorescent probe (PE) was not affected by MAB391 even at 100 μg/mL, and FIG. 8B, which shows the binding of MAB391 tagged with PE was only partially inhibited (50 to 60%) by R1 at 100 μg/mL. Additional results summarized in Table 3A indicate that the epitope of R1 is located in the CR domain between aa 151 and 282 and can be further located to the first half of the CR domain between aa 151 and 222 (Table 3B).

TABLE 3A

% binding of each labeled antibody (*) to rhIGF-1R-coated beads in the presence of the unlabeled antibody (24-31, 24-57, 17-69, 1-2, 1H7, 2C8, 3B7)

| Anti-IGF-1R | 24-31 | 24-57 | 17-69 | 1-2 | 1H7 | 2C8 | 3B7 |
|---|---|---|---|---|---|---|---|
| Epitope | 283-440 | 440-514 | 514-586 | 1323-1337 | ? | (301-450?) | (1-150?) |
| R1* | 100 | 100 | 100 | 100 | 150 | 100 | 117 |
| cR1* | 100 | 100 | 100 | 100 | 125 | 100 | 106 |
| hR1* | 100 | 100 | 100 | 100 | 131 | 100 | 100 |
| MAB391* | ND | ND | ND | ND | ND | ND | ND |
| 24-60* | 18 | 88 | 82 | 100 | 100 | 88 | 79 |
| αIR-3* | 52 | 87 | 89 | 95 | 115 | 97 | 76 |

TABLE 3B

% binding of each labeled antibody (*) to rhIGF-1R-coated beads in the presence of the unlabeled antibody (R1, cR1, hR1, 24-60, αIR-3, MAB391)

| Anti-IGF-1R | R1 | cR1 | hR1 | 24-60 | αIR-3 | MAB391 |
|---|---|---|---|---|---|---|
| Epitope | (151-282) | (151-282) | (151-282) 151-222 | 184-283 | 223-274 | (184-283) |
| R1* | 0 | 0 | 0 | 43 | 143 | 100 |
| cR1* | 0 | 0 | 0 | 40 | 128 | 108 |
| hR1* | 0 | 0 | 0 | 71 | 136 | 121 |
| 24-60* | 0 | 0 | 0 | 0 | 21 | 0 |
| αIR-3* | 86 | 97 | 107 | 0 | 0 | 0 |
| MAB391* | 40 | ND | ND | ND | ND | 0 |

Example 3. Additional Characterization of R1, cR1, and hR1

Figure 9:
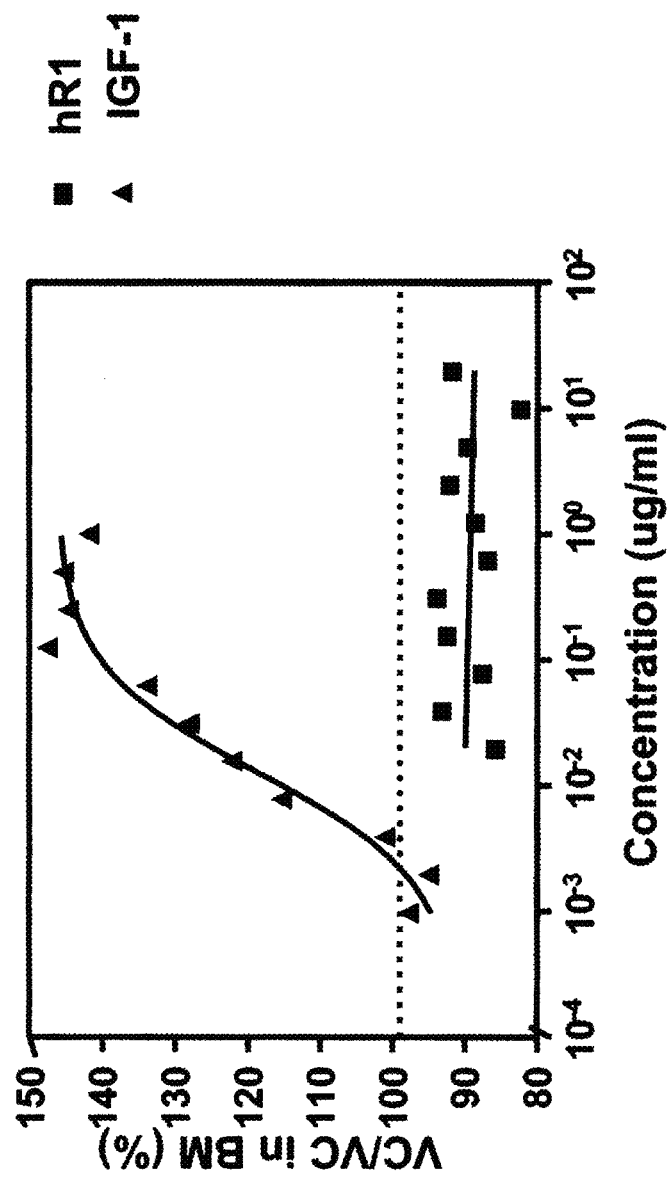
FIG. 9. Humanized R1 is not an agonist of the IGF-1R receptor. Unlike IGF-1, hR1 did not stimulate the proliferation of MCF-7 cells in serum-free medium.

Whereas IGF-1 stimulates proliferation of MCF-7 cells grown in serum-free medium, achieving a maximal effect of 50% increase in viable cell counts at 100 ng/mL when compared to the untreated control at 48 h, hR1 does not (FIG. 9). Thus hR1 is not agonistic upon binding to IGF-1R. Internalization of hR1 into MCF-7 was observed at 37° C. but not at 4° C. (not shown).

Example 4. Construction of Expression Vectors for hR1-IgG4(S228P) Variant

B13-24 cells containing an IgG4 gene are purchased from ATCC (ATCC Number CRL-11397) and genomic DNA is isolated. Briefly, cells are washed with PBS, resuspended in digestion buffer (100 mM NaCl, 10 mM Tris-HCl pH8.0, 25 mM EDTA pH8.0, 0.5% SDS, 0.1 mg/ml proteinase K) and incubated at 50° C. for 18 h. The sample is extracted with an equal volume of phenol/chloroform/isoamylalcohol and precipitated with 7.5 M NH.sub.4Ac/100% EtOH. Genomic DNA is recovered by centrifugation and dissolved in TE buffer. Using genomic DNA as template, the IgG4 gene is amplified by PCR using the following primers.

```
Primer-SacII
                                            (SEQ ID NO: 11)
CCGCGGTCACATGGCACCACCTCTCTTGCAGCTTCCACCAAGGGCCC Primer-EagI:
                                            (SEQ ID NO: 12)
CCGGCCGTCGCACTCATTTACCCAGAGACAGGG
```

Amplified PCR product is cloned into a TOPO-TA sequencing vector (Invitrogen) and confirmed by DNA sequencing. The SacII-EagI fragment containing the heavy chain constant region of IgG1 in hR1pdHL2 is replaced with SacII-EagI of the TOPO-TA-IgG4 plasmid to produce the hR1-pdHL2-IgG4 (hR1pdHL2-γ4) vector.

IgG4-Proline Mutation

A Ser228Pro mutation is introduced in the hinge region of IgG4 to avoid formation of half-molecules. A mutated hinge region 56 bp fragment (PstI-StuI) is synthesized

```
Top
                                            (SEQ ID NO: 13)
GAGTCCAAATATGGTCCCCCATGCCCACCGTGCCCAGGTAAGCCAACCCA

GG;

Bottom:
                                            (SEQ ID NO: 14)
CCTGGGTTGGCTTACCTGGGCACGGTGGGCATGGGGGACCATATTTGGAC

TCTGCA
``` annealed and replaced with the PstI-StuI fragment of IgG4. This construction results in a final vector hR1pdHL2-γ4P.

Example 5. Generation of Multivalent hR1-Based Antibodies by DNL

The DNL technique may be used to make multivalent, hR1-based antibodies in various formats that are either monospecific or bispecific. For certain preferred embodiments, Fab antibody fragments may be produced as fusion proteins containing either a DDD or AD sequence. Bispecific antibodies may be formed by combining a Fab-DDD fusion protein of a first antibody with a Fab-AD fusion protein of a second antibody. Alternatively, an IgG-AD module may be produced as a fusion protein and combines with a Fab-DDD module of the same or different specificity. Additional types of constructs may be made that combine the targeting capabilities of an antibody with the effector function of any other protein or peptide.

Independent transgenic cell lines are developed for each DDD- or AD-fusion protein. Once produced, the modules can be purified if desired or maintained in the cell culture supernatant fluid. Following production, any Fab-DDD module can be combined with any AD-module. DDD- or AD-modules may be produced synthetically such as linking an AD-sequence to polyethylene glycol or a DDD-sequence to an oligonucleotide. For different types of constructs, different AD or DDD sequences may be utilized.

```
DDD1:
                                            (SEQ ID NO: 15)
SHIQIPPGLTELLQGYTVEVLRQQPPDLVEFAVEYFTRLREARA

DDD2:
                                            (SEQ ID NO: 16)
CGHIQIPPGLTELLQGYTVEVLRQQPPDLVEFAVEYFTRLREARA

AD1:
                                            (SEQ ID NO: 17)
QIEYLAKQIVDNAIQQA

AD2:
                                            (SEQ ID NO: 18)
CGQIEYLAKQIVDNAIQQAGC
```

The plasmid vector pdHL2 has been used to produce a number of antibodies and antibody-based constructs. See, Gillies et al., J Immunol Methods (1989), 125:191-202; Losman et al., Cancer (Phila) (1997), 80:2660-6. The dicistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD, Fab-AD, or IgG-AD expression vectors, as described in detail below for Fab-DDD1 and Fab-AD1. To generate the expression vector for Fab-DDD1, the coding sequences for the hinge, $C_H2$ and $C_H3$ domains of the heavy chain are replaced with a sequence encoding the first 4 residues of the hinge, a 14 residue Gly-Ser linker and DDD1 (the first 44 residues of human RIIα). To generate the expression vector for Fab-AD1, the sequences for the hinge, $C_H2$ and $C_H3$ domains of IgG are replaced with a sequence encoding the first 4 residues of the hinge, a 15 residue Gly-Ser linker and AD1 (a 17 residue synthetic AD called AKAP-IS, which was generated using bioinformatics and peptide array technology and shown to bind RIIα dimers with a very high affinity (0.4 nM). See Alto, et al. Proc. Natl. Acad. Sci., U.S.A (2003), 100:4445-50).

To facilitate the conversion of IgG-pdHL2 vectors to either Fab-DDD1 or Fab-AD1 expression vectors, two shuttle vectors were designed and constructed as follows.

Preparation of $C_H1$

The $C_H1$ domain was amplified by PCR using the pdHL2 plasmid vector as a template. The left PCR primer consists of the upstream (5') end of the $C_H1$ domain and a SacII restriction endonuclease site, which is 5' of the $C_H1$ coding sequence. The right primer consists of the sequence coding for the first 4 residues of the hinge (PKSC) followed by four glycines and a serine, with the final two codons (GS) comprising a Bam HI restriction site.

```
5' of C_H1 Left Primer
                                            (SEQ ID NO: 19)
5'GAACCTCGCGGACAGTTAAG-3'

C_H1 + G_4S-Bam Right
("G_4S" disclosed as SEQ ID NO: 54)
                                            (SEQ ID NO: 20)
5'GGATCCTCCGCCGCCGCAGCTCTTAGGTTT

CTTGTCCACCTTGGTGTTGCTGG-3'
```

The 410 bp PCR amplimer was cloned into the pGemT PCR cloning vector (Promega, Inc.) and clones were screened for inserts in the T7 (5') orientation.

Construction of (G4S)2DDD1 ("(G4S)2" Disclosed as SEQ ID NO: 55)

A duplex oligonucleotide, designated (G4S)2DDD1 ("(G4S)2" disclosed as SEQ ID NO: 55), was synthesized by Sigma Genosys (Haverhill, UK) to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

```
                                        (SEQ ID NO: 21)
        GSGGGGSGGGGSHIQIPPGLTELLQGYT

VEVLRQQPPDLVEFAVEYFTRLREARA
```

The two oligonucleotides, designated RIIA1-44 top and RIIA1-44 bottom, that overlap by 30 base pairs on their 3' ends, were synthesized (Sigma Genosys) and combined to comprise the central 154 base pairs of the 174 bp DDD1 sequence. The oligonucleotides were annealed and subjected to a primer extension reaction with Taq polymerase.

```
RIIA1-44 top
                                        (SEQ ID NO: 34)
5'GTGGCGGGTCTGGCGGAGGTGGCAGCCACATCCAGATCCCGCCGGG

GCTCACGGAGCTGCTGCAGGGCTACACGGTGGAGGTGCTGCGACAG-3'

RIIA1-44 bottom
                                        (SEQ ID NO: 35)
5'GCGCGAGCTTCTCTCAGGCGGGTGAAGTACTCCACTGCGAATTCGAC

GAGGTCAGGCGGCTGCTGTCGCAGCACCTCCACCGTGTAGCCCTG-3'
```

Following primer extension, the duplex was amplified by PCR using the following primers:

```
G4S Bam-Left ("G4S" disclosed as SEQ ID NO: 54)
                                        (SEQ ID NO: 36)
5'-GGATCCGGAGGTGGCGGGTCTGGCGGAGGT-3'

1-44 stop Eag Right
                                        (SEQ ID NO: 37)
5'-CGGCCGTCAAGCGCGAGCTTCTCTCAGGCG-3'
```

This amplimer was cloned into pGemT and screened for inserts in the T7 (5') orientation.

Construction of (G4S)2-AD1 ("(G4S)2" Disclosed as SEQ ID NO: 55)

A duplex oligonucleotide, designated (G4S)2-AD1 ("(G4S)2" disclosed as SEQ ID NO: 55), was synthesized (Sigma Genosys) to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

```
                                        (SEQ ID NO: 38)
        GSGGGGSGGGGSQIEYLAKQIVDNAIQQA
```

Two complimentary overlapping oligonucleotides, designated AKAP-IS Top and AKAP-IS Bottom, were synthesized.

```
AKAP-IS Top
                                        (SEQ ID NO: 22)
5'GGATCCGGAGGTGGCGGGTCTGGCGGAGGTGG

CAGCCAGATCGAGTACCTGGCCAAGCAGATCGT

GGACAACGCCATCCAGCAGGCCTGACGGCCG-3'

AKAP-IS Bottom
                                        (SEQ ID NO: 23)
5'CGGCCGTCAGGCCTGCTGGATGGCGTTGTCCA

CGATCTGCTTGGCCAGGTACTCGATCTGGCTGCC

ACCTCCGCCAGACCCGCCACCTCCGGATCC-3'
```

The duplex was amplified by PCR using the following primers:

```
G4SBam-Left ("G4S" disclosed as SEQ ID NO: 54)
                                        (SEQ ID NO: 24)
5'-GGATCCGGAGGTGGCGGGTCTGGCGGAGGT-3'

AKAP-IS stop Eag Right
                                        (SEQ ID NO: 25)
5'-CGGCCGTCAGGCCTGCTGGATG-3'
```

This amplimer was cloned into the pGemT vector and screened for inserts in the T7 (5') orientation.

Ligating DDD1 with CH1

A 190 bp fragment encoding the DDD1 sequence was excised from pGemT with BamHI and NotI restriction enzymes and then ligated into the same sites in $C_H1$-pGemT to generate the shuttle vector $C_H1$-DDD1-pGemT.

Ligating AD1 with CH1

A 110 bp fragment containing the AD1 sequence was excised from pGemT with BamHI and NotI and then ligated into the same sites in CH1-pGemT to generate the shuttle vector CH1-AD1-pGemT.

Cloning CH1-DDD1 or CH1-AD1 into pdHL2-Based Vectors

With this modular design either $C_H1$-DDD1 or CH1-AD1 can be incorporated into any IgG-pdHL2 vector. The entire heavy chain constant domain is replaced with one of the above constructs by removing the SacII/EagI restriction fragment ($C_H1$-$C_H3$) from pdHL2 and replacing it with the SacII/EagI fragment of $C_H1$-DDD1 or $C_H1$-AD1, which is excised from the respective pGemT shuttle vector.

CH1-DDD2-Fab-hR1-pdHL2

$C_H1$-DDD2-Fab-hR1-pdHL2 is an expression vector for production of $C_H1$-DDD2-Fab-hR1, which possesses a dimerization and docking domain sequence of DDD2 appended to the carboxyl terminus of the Fd via a 14 amino acid residue Gly/Ser peptide linker.

The expression vector was engineered as follows. Two overlapping, complimentary oligonucleotides, which comprise the coding sequence for part of the linker peptide (GGGGSGGGCG, SEQ ID NO:26) and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

```
G4S-DDD2 top ("G4S" disclosed as SEQ ID NO: 54)
                                        (SEQ ID NO: 27)
5'GATCCGGAGGTGGCGGGTCTGGCGGAGGTTGCGGCCA

CATCCAGATCCCGCCGGGGCTCACGGAGCTGCTGCA-3'
```

-continued

G4S-DDD2 bottom ("G4S" disclosed as SEQ ID NO: 54)
(SEQ ID NO: 28)
5'GCAGCTCCGTGAGCCCCGGCGGGATCTGGATGTGGCC

GCAACCTCCGCCAGACCCGCCACCTCCG-3'

The duplex DNA was ligated with the shuttle vector CH1-DDD1-pGemT, which was prepared by digestion with BamHI and PstI, to generate the shuttle vector CH1-DDD2-pGemT. A 507 bp fragment was excised from CH1-DDD2-pGemT with SacII and EagI and ligated with the IgG expression vector hR1pdHL2, which was prepared by digestion with SacII and EagI. The final expression construct is $C_H1$-DDD2-Fab-hR1-pdHL2.

Generation of $C_H1$-AD2-Fab-h679-pdHL2

$C_H1$-AD2-Fab-h679-pdHL2 is an expression vector for the production of $C_{H1}$-AD2-Fab-h679 and is useful as a template for the DNA sequence encoding AD2. The expression vector is engineered as follows. Two overlapping, complimentary oligonucleotides (AD2 Top and AD2 Bottom), which comprise the coding sequence for AD2 and part of the linker sequence, are made synthetically. The oligonucleotides are annealed and phosphorylated with T4 polynucleotide kinase, resulting in overhangs on the 5' and 3' ends that are compatible for ligation with DNA digested with the restriction endonucleases BamHI and SpeI, respectively.

AD2 Top
(SEQ ID NO: 29)
5'GATCCGGAGGTGGCGGGTCTGGCGGATGTGGCCAGATCGAGTACCTG

GCCAAGCAGATCGTGGACAACGCCATCCAGCAGGCCGGCTGCTGAA-3'

AD2 Bottom
(SEQ ID NO: 30)
5'TTCAGCAGCCGGCCTGCTGGATGGCGTTGTCCACGATCTGCTTGGC

CAGGTACTCGATCTGGCCACATCCGCCAGACCCGCCACCTCCG-3'

The duplex DNA is ligated into the shuttle vector $C_H1$-AD1-pGemT, which is prepared by digestion with BamHI and SpeI, to generate the shuttle vector CH1-AD2-pGemT. A 429 base pair fragment containing $C_H1$ and AD2 coding sequences is excised from the shuttle vector with SacII and EagI restriction enzymes and ligated into h679-pdHL2 vector that is prepared by digestion with those same enzymes, resulting in $C_H1$-AD2-Fab-h679-pdHL2.

Generation of $C_H3$-AD2-IgG-pdHL2 for Expressing $C_{H3}$-AD2-IgG $C_H3$-AD2-IgG modules have an AD2 peptide fused to the carboxyl terminus of the heavy chain of IgG via a 9 amino acid residue peptide linker. The DNA coding sequences for the linker peptide (GSGGGGSGG, SEQ ID NO:31) followed by the AD2 peptide (CGQIEYLAKQIVDNAIQQAGC, SEQ ID NO:18) are coupled to the 3' end of the $C_H3$ (heavy chain constant domain 3) coding sequence by standard recombinant DNA methodologies, resulting in a contiguous open reading frame. When the heavy chain-AD2 polypeptide is co-expressed with a light chain polypeptide, an IgG molecule is formed possessing two AD2 peptides, which can therefore bind two Fab-DDD2 dimers. The $C_H3$-AD2-IgG module can be combined with any $C_H1$-DDD2-Fab module to generate a wide variety of hexavalent structures composed of an Fc fragment and six Fab fragments. If the $C_H3$-AD2-IgG module and the $C_H1$-DDD2-Fab module are derived from the same parental monoclonal antibody (MAb) the resulting complex is monospecific with 6 binding arms to the same antigen. If the modules are instead derived from two different MAbs then the resulting complexes are bispecific, with two binding arms for the specificity of the $C_H3$-AD2-IgG module and 4 binding arms for the specificity of the $C_H1$-DDD2-Fab module.

A plasmid shuttle vector was produced to facilitate the conversion of any IgG-pdHL2 vector into a $C_H3$-AD2-IgG-pdHL2 vector. The gene for the Fc ($C_H2$ and $C_H3$ domains) was amplified using the pdHL2 vector as a template and the oligonucleotides Fc BglII Left and Fc Bam-EcoRI Right as primers.

Fc BglII Left
(SEQ ID NO: 32)
5'-AGATCTGGCGCACCTGAACTCCTG-3'

Fc Bam-EcoRI Right
(SEQ ID NO: 33)
5'-GAATTCGGATCCTTTACCCGGAGACAGGGAGAG-3'

The amplimer was cloned in the pGemT PCR cloning vector. The Fc insert fragment was excised from pGemT with XbaI and BamHI restriction enzymes and ligated with AD2-pdHL2 vector that was prepared by digestion of $C_H1$-AD2-Fab-h679-pdHL2 with XbaI and BamHI, to generate the shuttle vector Fc-AD2-pdHL2.

To convert any IgG-pdHL2 expression vector to a $C_H3$-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the $C_H3$ domain and NdeI cuts downstream (3') of the expression cassette.

Generation of Hex-hR1

The DNL method is used to create Hex-hR1, a monospecific anti-IGF-1R with one Fc and six Fabs, by combining $C_{H3}$-AD2-IgGhR1 with $C_H1$-DDD2-Fab-hR1. Hex-hR1 is made in four steps.

Step 1, Combination:

$C_H1$-DDD2-Fab-hR1 is mixed with $C_H3$-AD2-IgG-hR1 in phosphate buffered saline, pH 7.4 (PBS) with 1 mM EDTA, at a molar ratio of 4.2 such that there are two $C_H1$-DDD2-Fab-hR1 for each AD2 on $C_H3$-AD2-IgG-hR1, allowing some excess of $C_H1$-DDD2-Fab-hR1 to ensure that the coupling reaction is complete.

Step 2, Mild Reduction:

Reduced glutathione (GSH) is added to a final concentration of 1 mM and the solution is held at room temperature (16-25° C.) for 1 to 24 hours.

Step 3, Mild Oxidation:

Following reduction, oxidized glutathione (GSSH) is added directly to the reaction mixture to a final concentration of 2 mM and the solution is held at room temperature for 1 to 24 hours.

Step 4, Isolation of the DNL Product:

Following oxidation, the reaction mixture is loaded directly onto a Protein-A affinity chromatography column. The column is washed with PBS and the Hex-hR1 eluted with 0.1 M Glycine, pH 2.5. The unreacted $C_H1$-DDD2-Fab-hR1 is removed from the desired product in the unbound fraction. Other hexavalent DNL constructs can be prepared similarly by mixing a selected pair of $C_H3$-AD2-IgG and $C_H1$-DDD2-Fab.

A list of such DNL constructs and structural controls related to the present invention is provided in Table 4. Each of these constructs was shown to retain the binding activities of the constitutive antibodies.

TABLE 4 hR1-containing DNL constructs and structural controls

| DNL code | IgG-AD2 | Fab-DDD2 | Valency 2 | Valency 4 | Valency 6 |
|---|---|---|---|---|---|
| Hex-hR1 | hR1 | hR1 | — | — | IGF-1R |
| Hex-hRS7 | hRS7 | hRS7 | — | — | EGP-1 |
| Hex-hPAM4 | hPAM4 | hPAM4 | — | — | MUC1 |
| Hex-hMN-14 | hMN-14 | hMN14 | — | — | CEACAM5 |
| Hex-hLL1 | hLL1 | hLL1 | — | — | CD74 |
| Hex-hL243 | hL243 | hL243 | — | — | HLA-DR |
| 1R-E1 | hR1 | hRS7 | IGF-1R | EGP-1 | — |
| 1R-14 | hR1 | hMN-14 | IGF-1R | CEACAM5 | — |
| 1R-15 | hR1 | hMN-15 | IGF-1R | CEACAM6 | — |
| 1R-31 | hR1 | hAFP | IGF-1R | AFP | — |
| 1R-74 | hR1 | hLL1 | IGF-1R | CD74 | — |
| 1R-C2 | hR1 | hL243 | IGF-1R | HLA-DR | — |
| 1R-M1 | hR1 | hPAM4 | IGF-1R | MUC1 | — |
| E1-1R | hRS7 | hR1 | EGP-1 | IGF-1R | — |
| M1-1R | hPAM4 | hR1 | MUC1 | IGF-1R | — |
| 14-1R | hMN-14 | hR1 | CEACAM5 | IGF-1R | — |
| 74-1R | hLL1 | hR1 | CD74 | IGF-1R | — |
| C2-1R | hL243 | hR1 | HLA-DR | IGF-1R | — |
| 22-20 | hLL2 | hA20 | CD22 | CD20 | — |

Example 7. IGF-1R Expression in Cancer Cell Lines

Figure 10A:
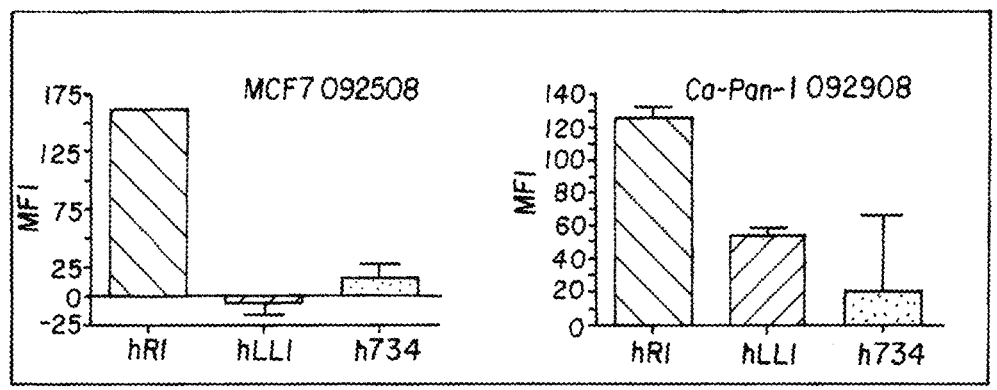
FIG. 10A. IGF-1R expression in cell lines determined by Guava Express analysis using Zenon-labeled antibodies. Expression of IGF-1R was confirmed by the binding of hR1 to MCF-7 (breast cancer).
Figure 10B:
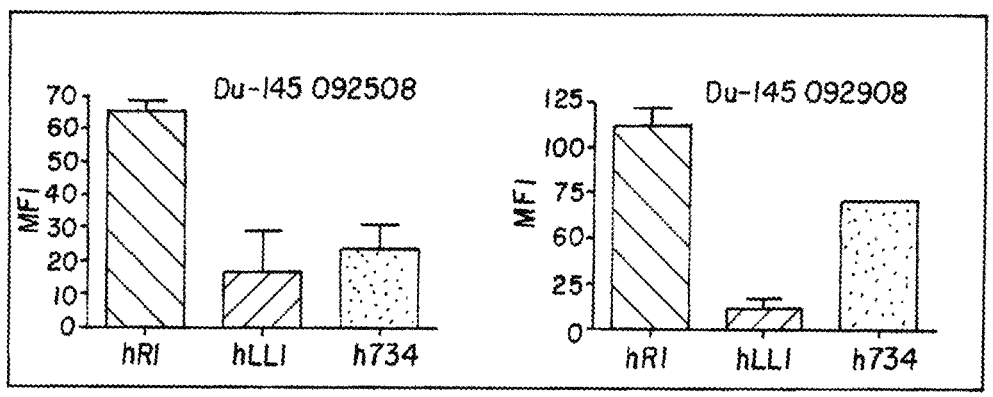
FIG. 10B. IGF-1R expression in cell lines determined by Guava Express analysis using Zenon-labeled antibodies. Expression of IGF-1R was confirmed by the binding of hR1 to CaPan1 (pancreatic cancer).
Figure 10C:
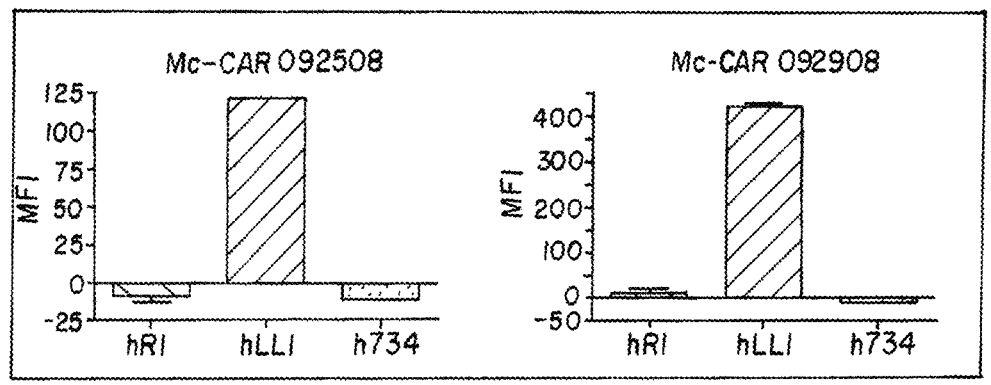
FIG. 10C. IGF-1R expression in cell lines determined by Guava Express analysis using Zenon-labeled antibodies. Expression of IGF-1R was confirmed by the binding of hR1 to DU-145 (prostate cancer).
Figure 11:
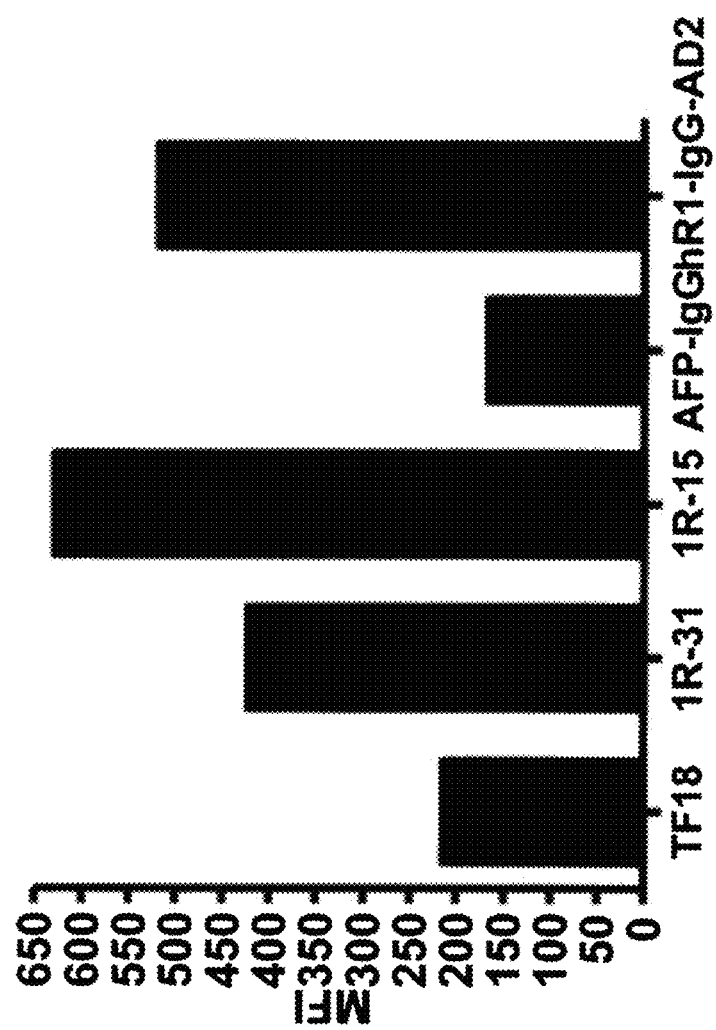
FIG. 11. Binding of DNL constructs comprising the hR1 antibody or Fab fragments thereof to cell lines expressing IGF-1R. Hep G2 liver cancer cells were incubated with the DNL constructs TF-18 (humanized anti-AFP), 1R-31 (humanized anti-AFP/humanized anti-IGF-1R), 1R-15 (humanized anti-IGF-1R/humanized anti-CEACAM6), 31-1R (humanized anti-AFP IgG and hR1-IgG-AD2).
Figure 12A:
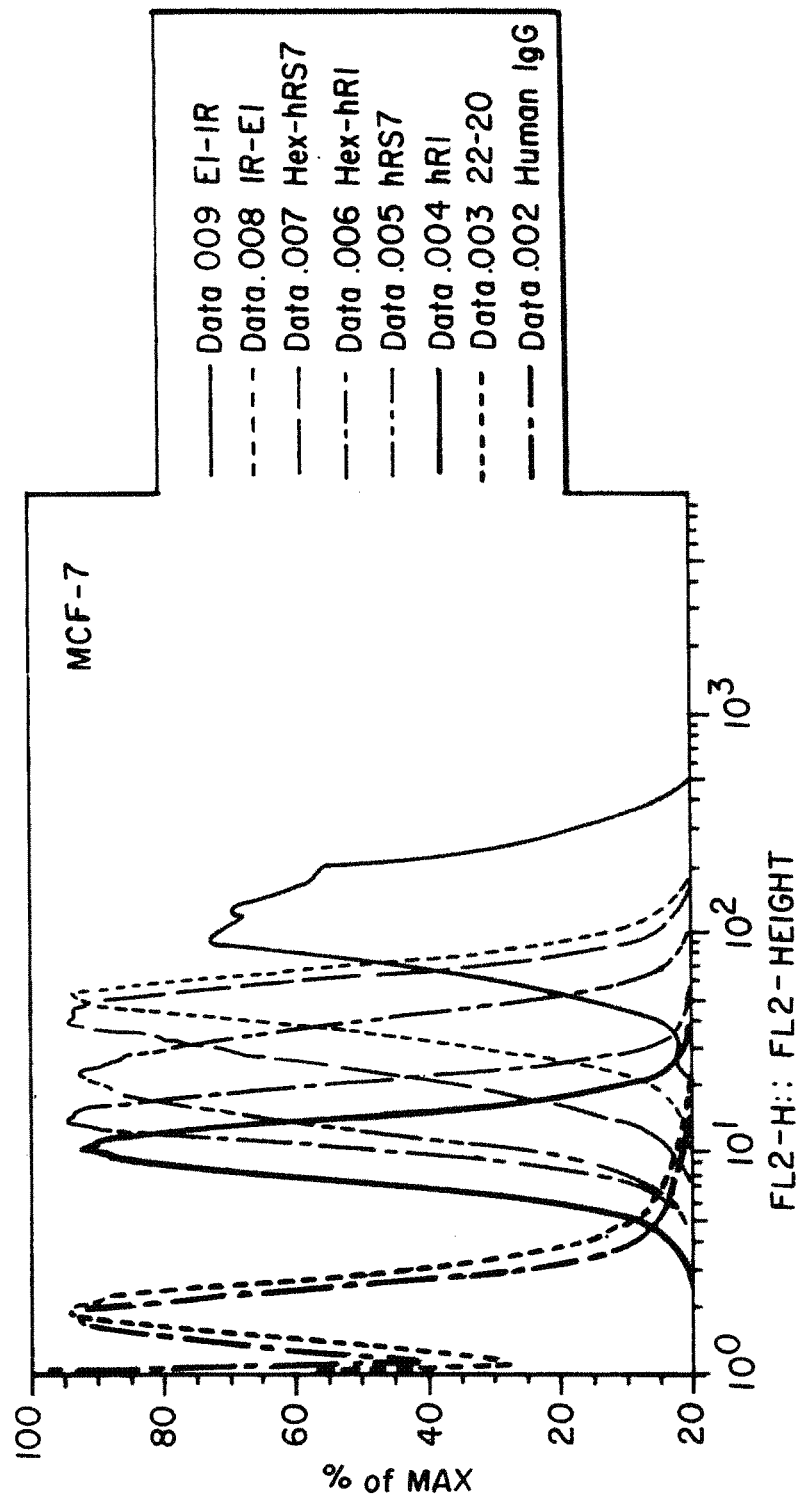
FIG. 12A. Binding of DNL constructs to MCF-7 cells determined on FACScan with DNL constructs or intact antibodies. Hex refers to hexavalent DNL constructs. hRS7 is a humanized anti-EGP-1 antibody.
Figure 12B:
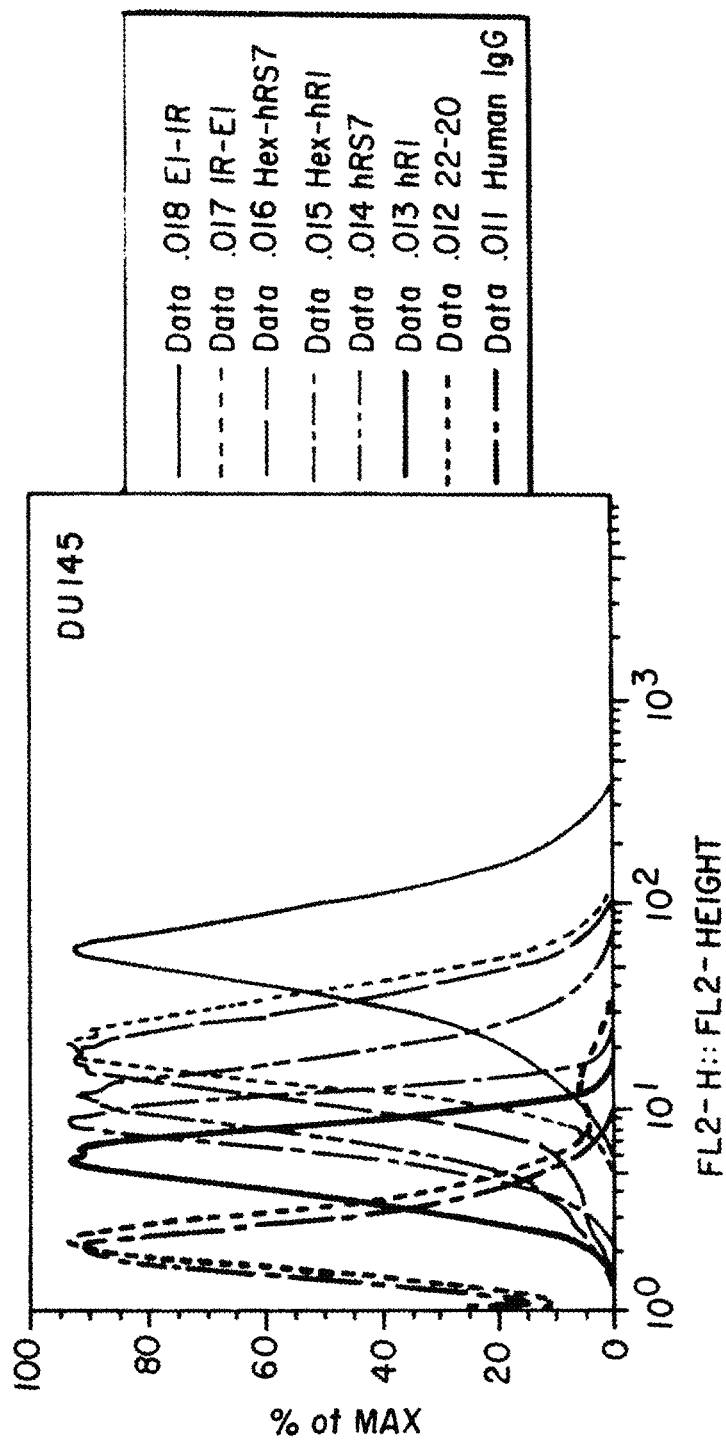
FIG. 12B. Binding of DNL constructs to DU-145 cells determined on FACScan with DNL constructs or intact antibodies. Hex refers to hexavalent DNL constructs. hRS7 is a humanized anti-EGP-1 antibody.
Figure 12C:
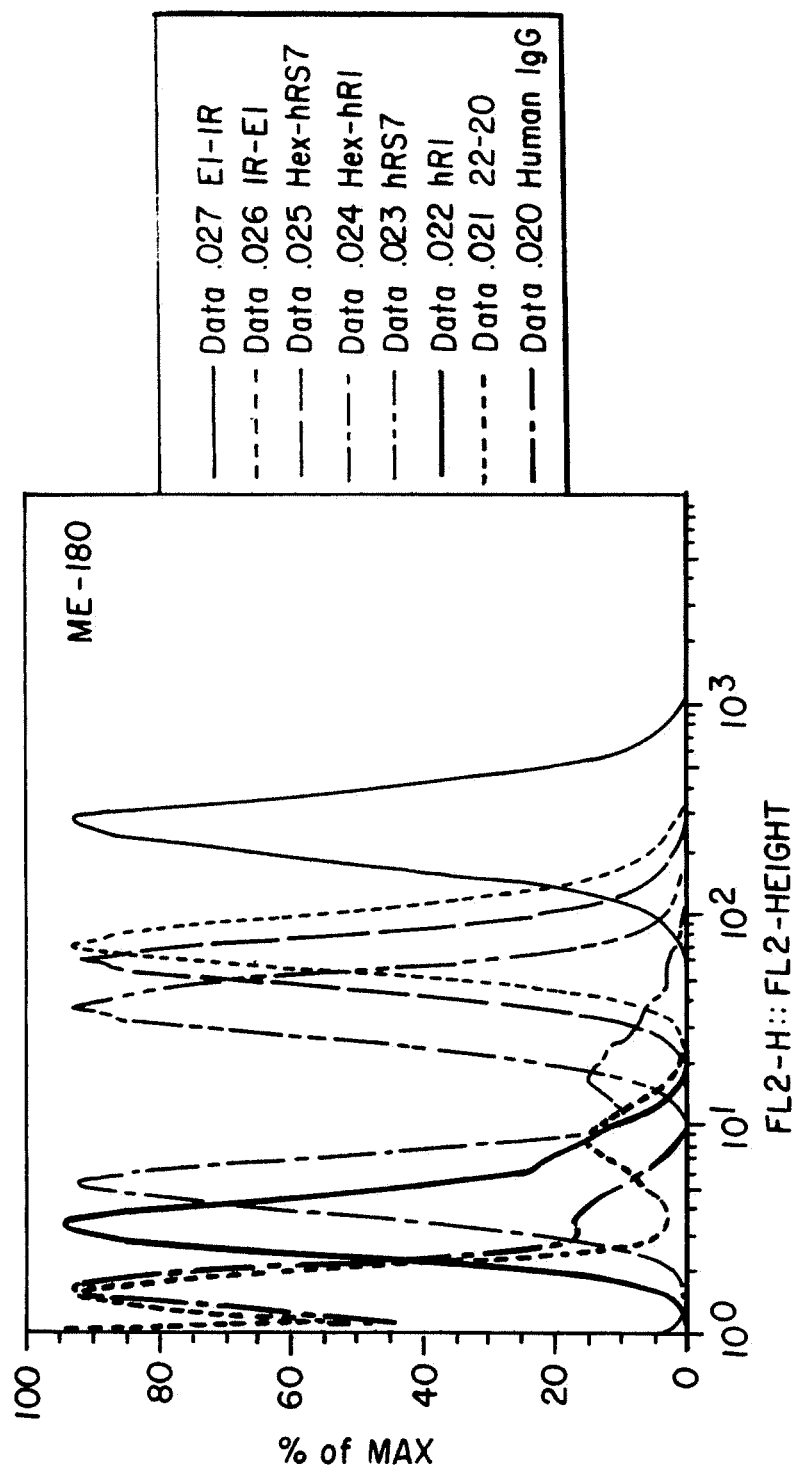
FIG. 12C. Binding of DNL constructs to ME-180 cells determined on FACScan with DNL constructs or intact antibodies. Hex refers to hexavalent DNL constructs. hRS7 is a humanized anti-EGP-1 antibody.

Zenon-labeled various parental antibodies as well as multivalent antibodies derived from these antibodies were used to assess the expression levels of cognate antigens in several cancer cell lines by flow cytometry performed on Guava instrument. Expression of IGF-1R was confirmed by the binding of hR1 to MCF-7 (breast cancer), CaPan1 (pancreatic cancer), and DU-145 (prostate cancer), as shown in FIG. 10. The dual expression of IGF-1R and AFP in HepG2 (liver cancer) was also shown in FIG. 11 by the binding of humanized anti-AFP IgG and TF18 (made by combining $C_{H}1$-DDD2-Fab-hAFP with $C_{H1}$-AD2-Fab-h679 to contain two Fab fragments of hAFP), as well as by the enhanced binding of hR1-IgG-AD2 (the dimer of $C_{H}3$-AD2-IgG-hR1) and 1R-31, suggesting a higher affinity of these multivalent DNL constructs. The expression of CEACAM6 in Hep G2 was noted by the observation of the enhanced binding of 1R-15. Additional studies performed with MCF-7, DU-145, and ME-180 (cervical cancer) on FACScan are presented in FIG. 12 and summarized in Table 5, which corroborate the findings by Guava that the multivalent DNL constructs exhibit enhanced binding to target cell lines compared to their parental antibodies. Interestingly, the multivalent, bispecific constructs appear to bind more avidly than their multivalent, monospecific counterparts in cell lines expressing differential levels of relevant antigens.

TABLE 5

Flow cytometry data obtained from FACScan

| | MCF-7 | | | DU145 | | | ME-180 | |
|---|---|---|---|---|---|---|---|---|
| Antibody | MFI | % Positive | Antibody | MFI | % Positive | Antibody | MFI | % Positive |
| | / | / | — | 2.4 | 1.96 | — | 1.86 | 2 |
| human IgG | 1.84 | 2.34 | human IgG | 2.21 | 1.44 | human IgG | 1.8 | 1.37 |
| 22-20 | 2.11 | 3.1 | DNL1 | 2.74 | 7.88 | DNL1 | 1.98 | 12.6 |
| hR1 | 9.93 | 89.15 | hR1 | 5.33 | 30.39 | hR1 | 3.65 | 10.74 |
| hRS7 | 21.42 | 99.15 | hRS7 | 10.58 | 82.82 | hRS7 | 35.54 | 99.96 |
| Hex-hR1 | 14.08 | 98.58 | Hex-hR1 | 7.83 | 72.56 | Hex-hR1 | 6.36 | 33.02 |
| Hex-hRS7 | 35.73 | 99.86 | Hex-hRS7 | 17.03 | 93.74 | Hex-hRS7 | 59.58 | 99.95 |
| 1R-E1 | 47.85 | 99.92 | 1R-E1 | 22.10 | 99.53 | 1R-E1 | 76.29 | 99.94 |
| E1-1R | 109.19 | 98.77 | E1-1R | 53.96 | 99.9 | E1-1R | 254.8 | 99.89 |

Example 8. Neutralizing Activity of Hex-hR1 and 1R-E1

Figure 13A:
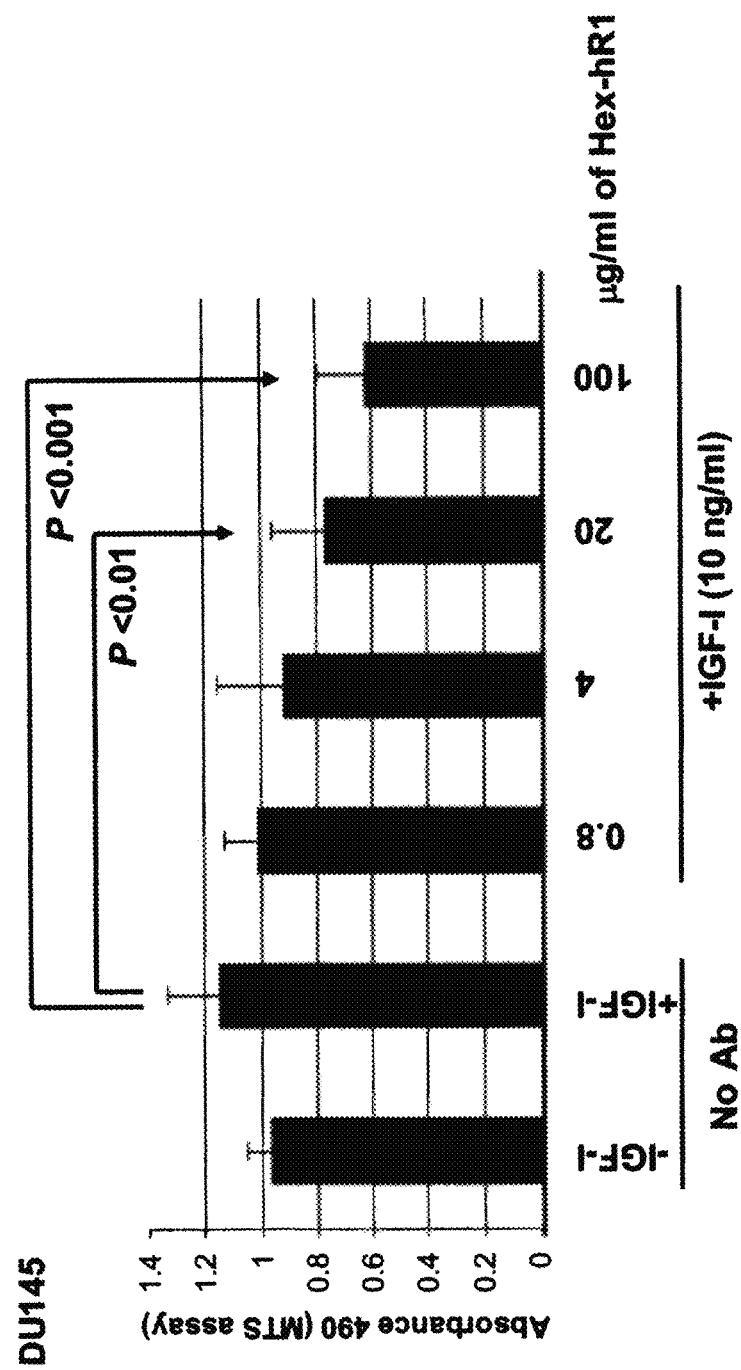
FIG. 13A. Effect of DNL constructs on neutralizing the growth stimulating activity of IGF-1 in DU-145 cells expressing both IGF-1R and EGP-1. The Hex-hR1 construct, comprising anti-IGF-1R, suppressed proliferation of DU-145.
Figure 13B:
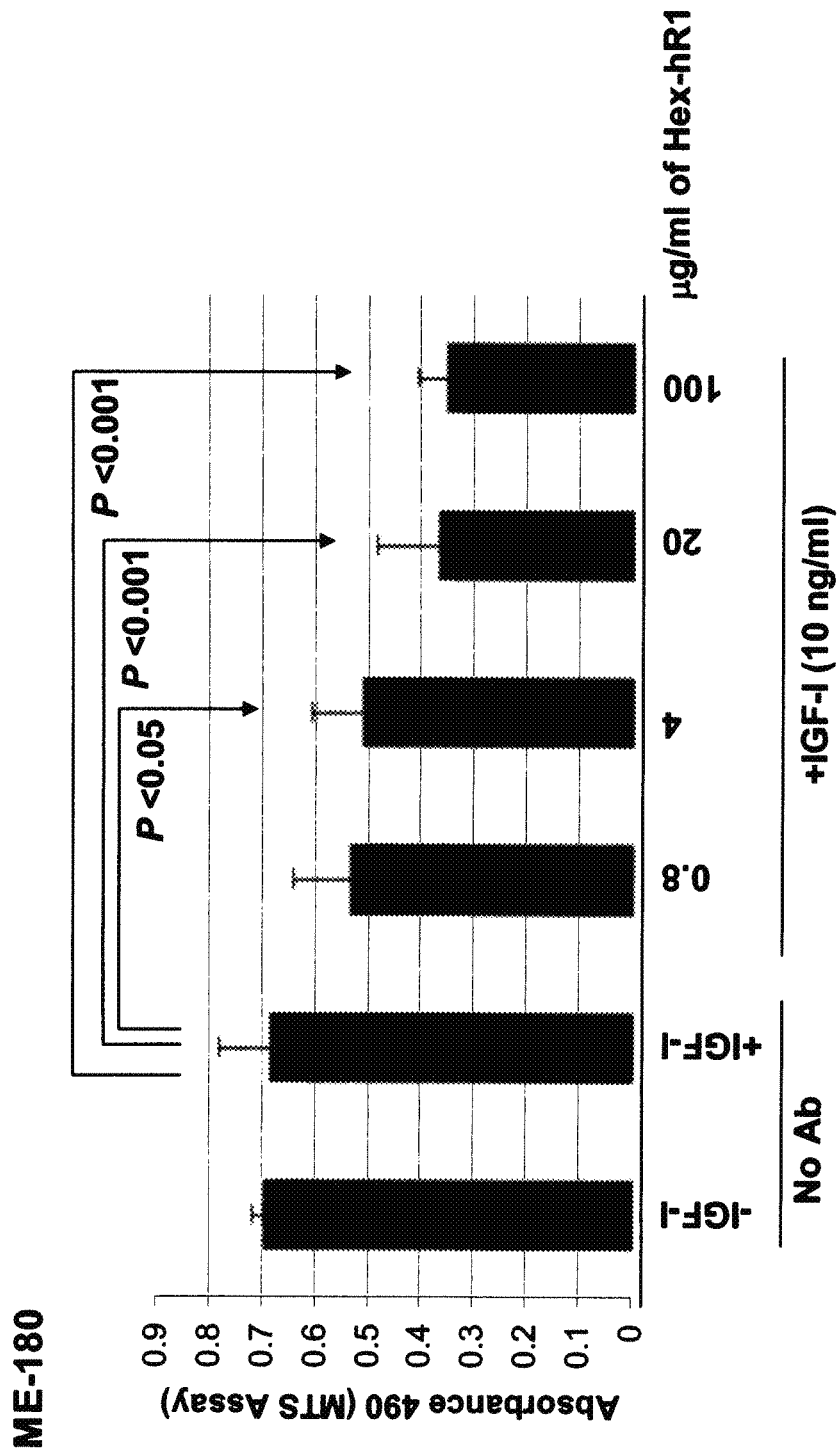
FIG. 13B. Effect of DNL constructs on neutralizing the growth stimulating activity of IGF-1 in ME-180 cells expressing both IGF-1R and EGP-1. The Hex-hR1 construct, comprising anti-IGF-1R, suppressed proliferation of ME-180.
Figure 13C:
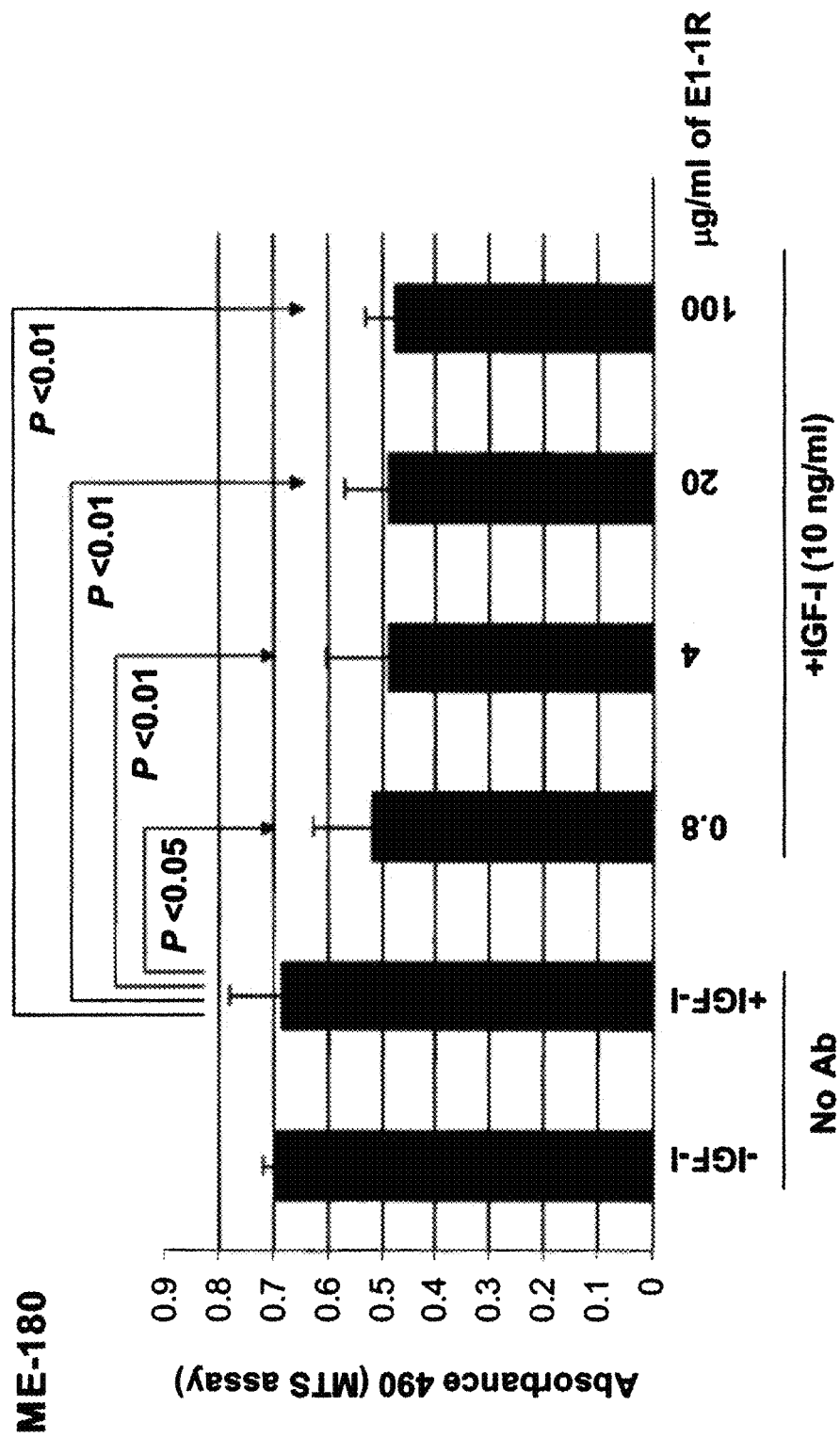
FIG. 13C. Effect of DNL constructs on neutralizing the growth stimulating activity of IGF-1 in ME-180 cells expressing both IGF-1R and EGP-1. The 1R-E1 construct comprising anti-IGF-1R and anti-EGP-1, suppressed proliferation of ME-180.

The following experiments were performed to determine the effect of Hex-hR1 or 1R-E1 on neutralizing the growth stimulating activity of IGF-1 in DU-145 and ME-180, both of which express IGF-1R and EGP-1. Target cells were seeded at 2000/well onto 96-well plates and grown overnight in complete medium. Cells were washed twice with serum free medium and exposed to a selected multivalent antibody at 0.8, 4, 20, and 100 µg/mL in serum free medium for 2 h, followed by the addition of IGF-1 to a final concentration of 10 ng/ml. Cells were incubated for 72 hours and then subjected to MTS assay. Under these conditions, Hex-hR1 suppressed the proliferation of DU-145 (FIG. 13A) and ME-180 (FIG. 13B) in a dose-dependent manner with statistical significance. Similar results were obtained with 1R-E1 in ME-180 (FIG. 13C).

Example 9. Downregulation of IGF-1R

Figures 14A, 14B:
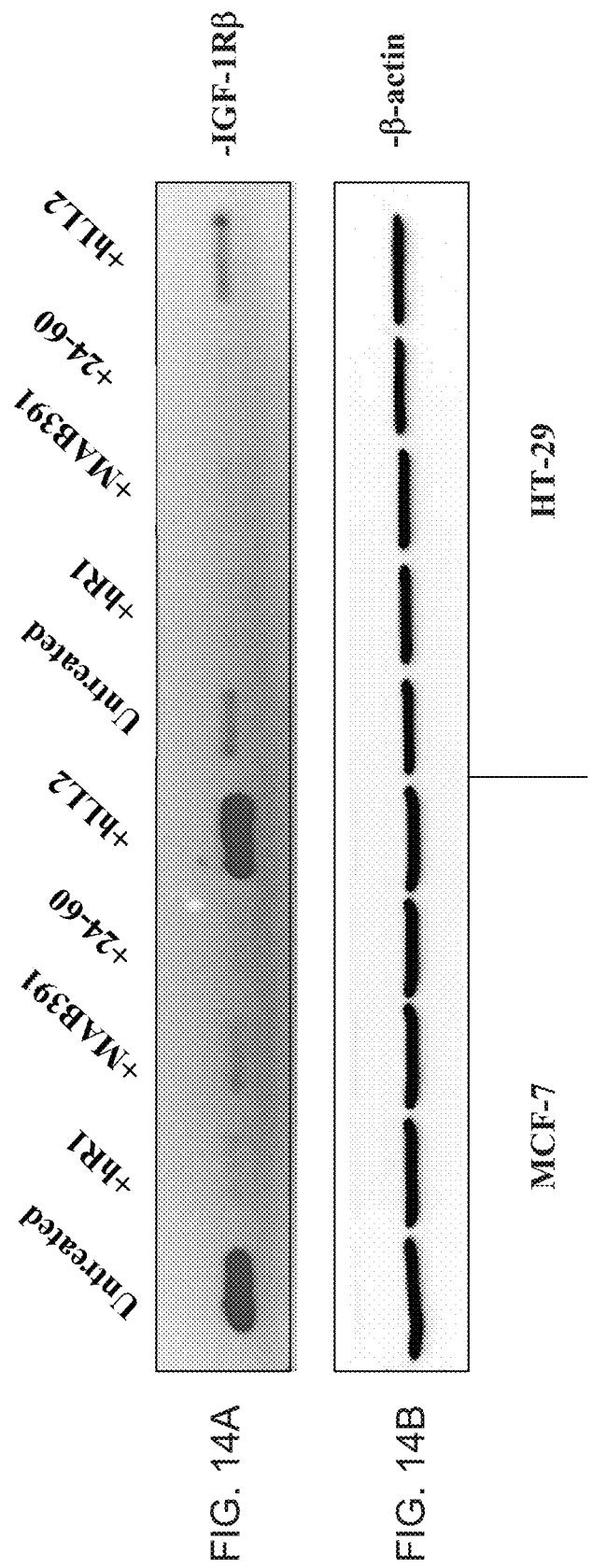
FIG. 14A. Down-regulation of IGF-1R in MCF-7 and HT-29 cells treated with hR1, MAB391 and 24-60 antibodies but not hLL2 control antibody.
FIG. 14B. Neither hR1, MAB391 nor hLL2 had any effect on expression of β-actin control in MCF-7 and HT-29 cells.
Figure 15A:
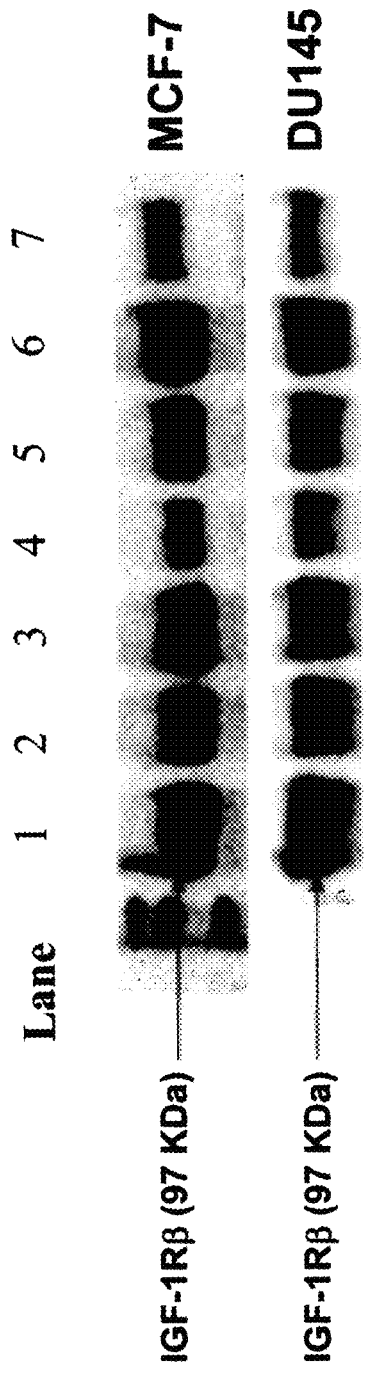
FIG. 15A. Down-regulation of IGF-1R in MCF-7 and DU-145 cells treated with Hex-hR1 or 1R-E1 DNL constructs.
Figure 15B:
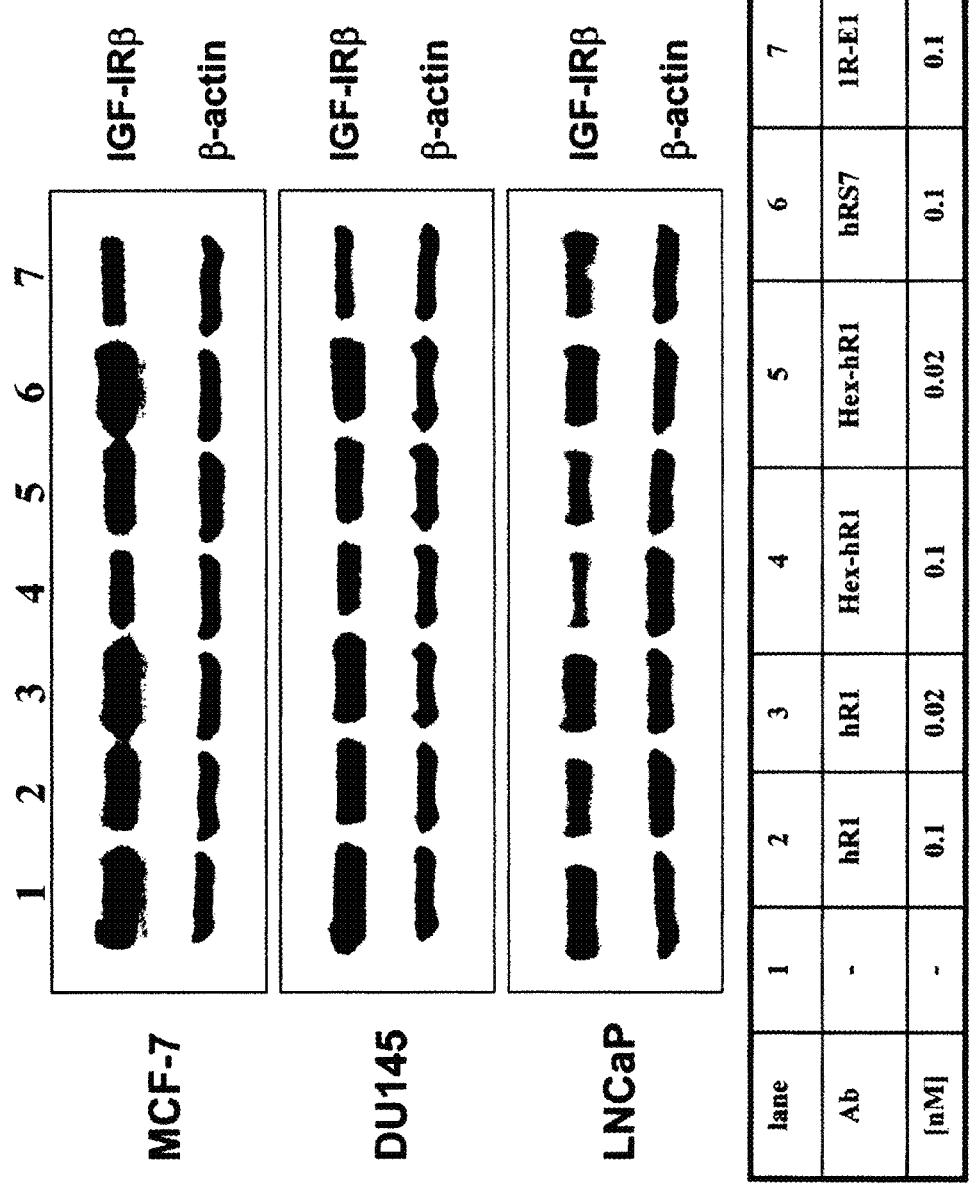
FIG. 15B. Down-regulation of IGF-1R in MCF-7, DU-145 and LNCaP cells treated with Hex-hR1 or 1R-E1 DNL constructs.
Figure 16:
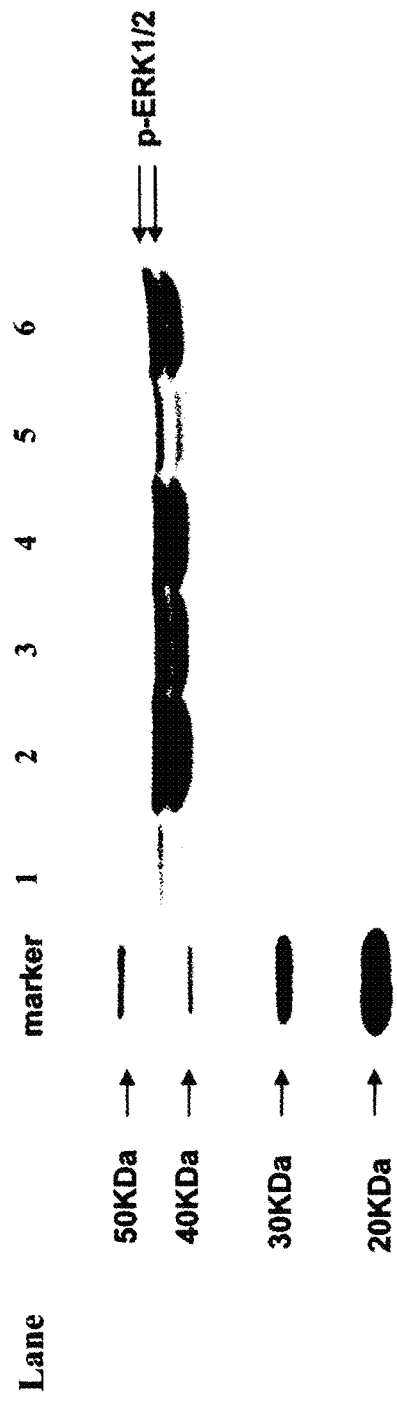
FIG. 16. Hex-hR1 blocks IGF-1 activation of ERK1/2 phosphorylation in MCF-7 cells. Hex-hR1 and control DNL construct Hex-hRS7 were added at 10 nM to cells treated with 100 ng/ml IGF-1.
Figure 17A:
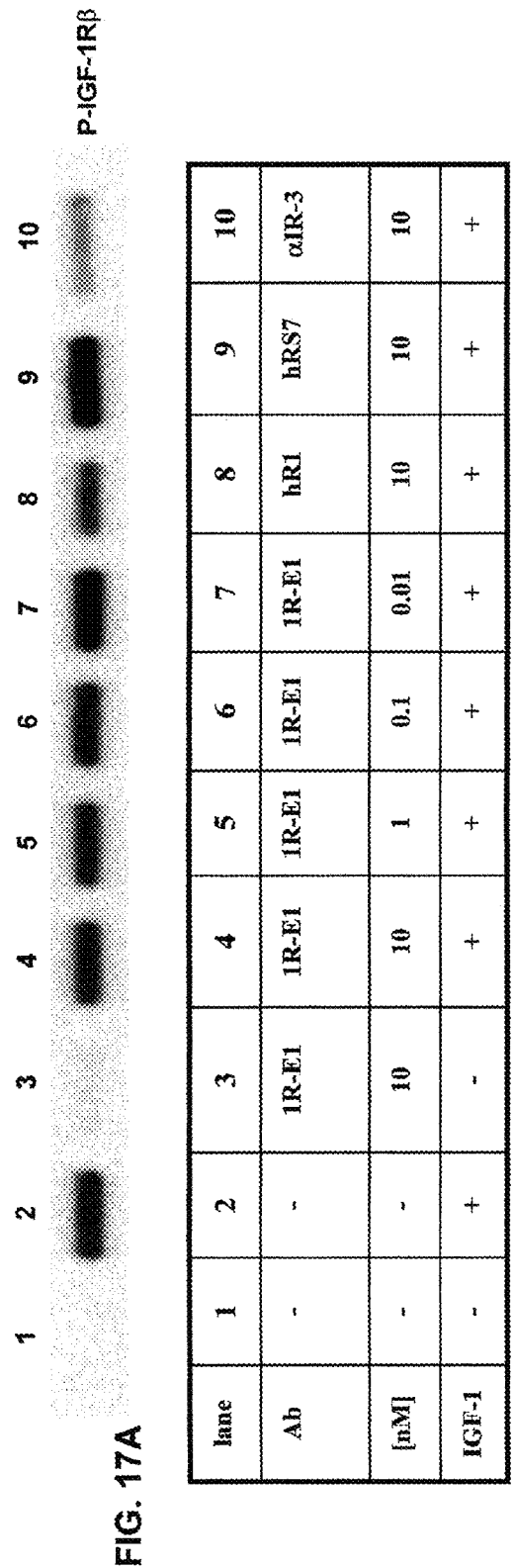
FIG. 17A. 1R-E1 and hR1 block IGF-1 activation of IGF-1R phosphorylation in ME-180 cells. The indicated concentrations of DNL construct 1R-E1, hR1 and control hRS7 antibodies were added to cells treated with 100 nM IGF-1.
Figure 17B:
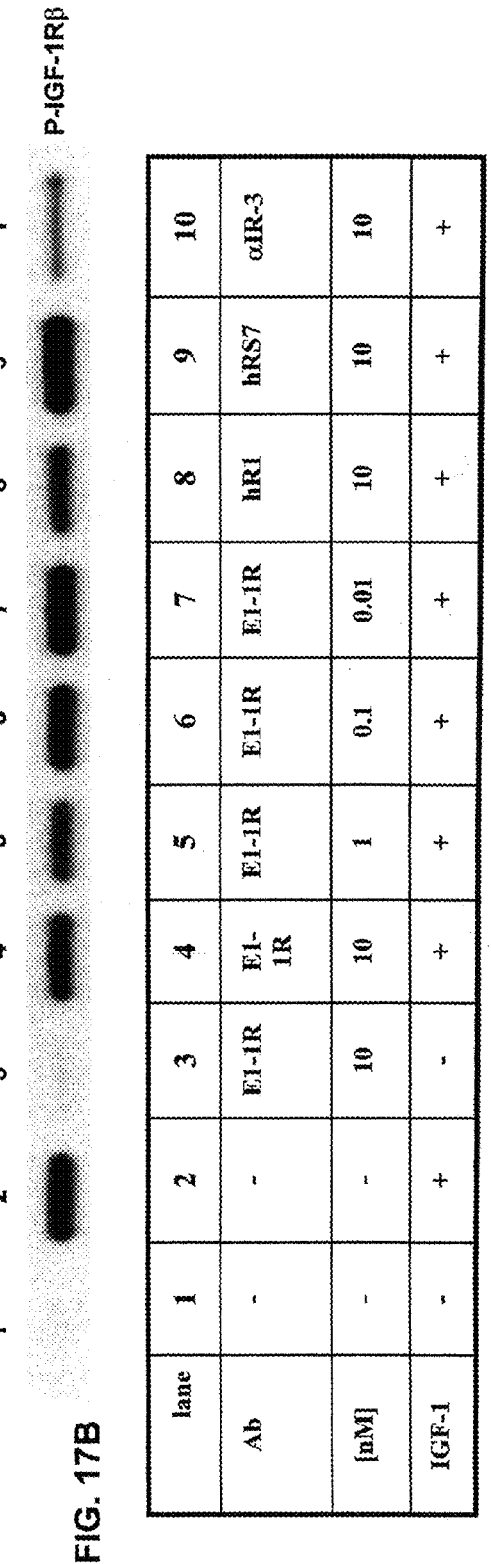
FIG. 17B. E1-1R and hR1 block IGF-1 activation of IGF-1R phosphorylation in ME-180 cells. The indicated concentrations of DNL construct E1-1R, hR1 and control hRS7 antibodies were added to cells treated with 100 nM IGF-1.
Figure 18:
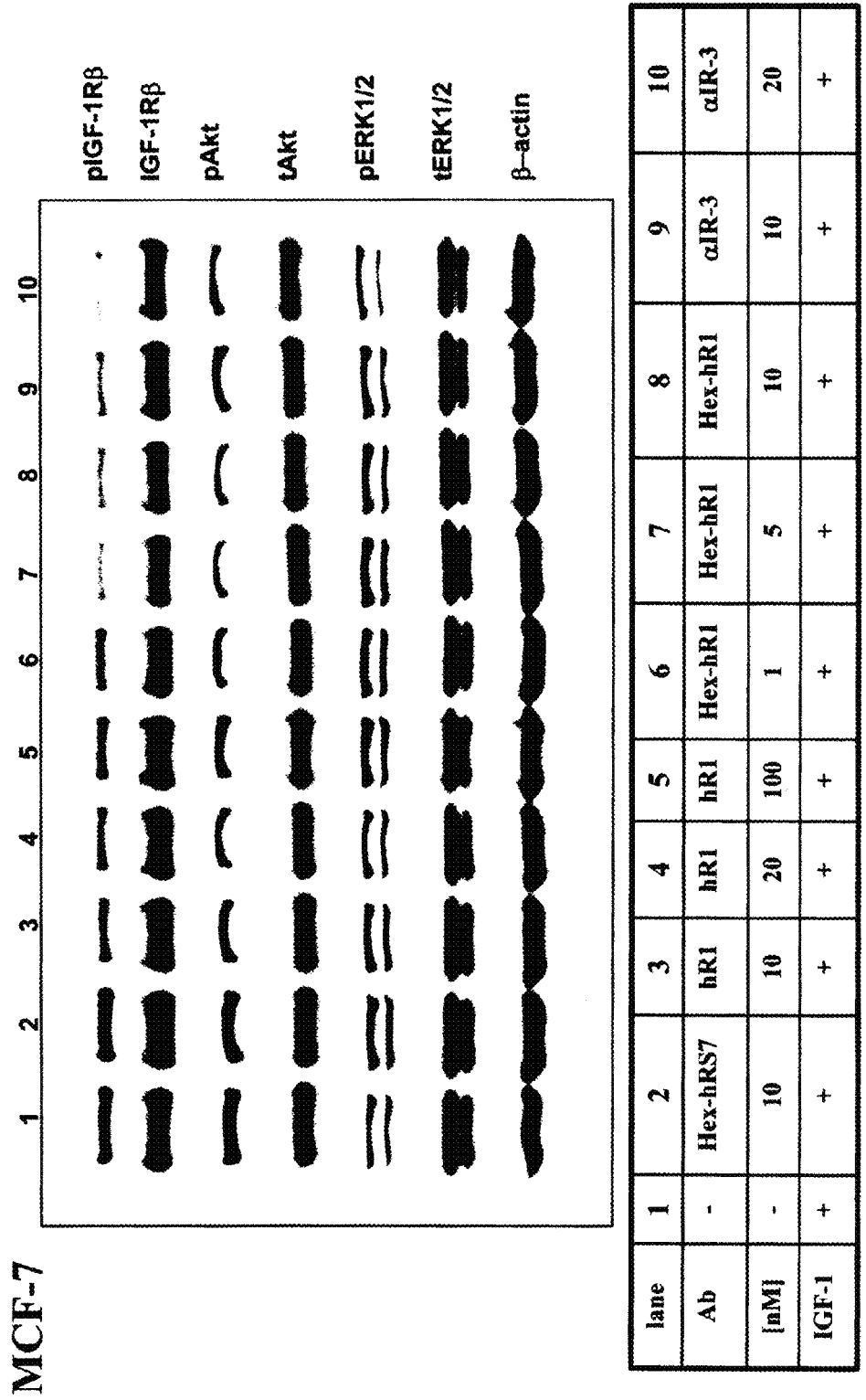
FIG. 18. Hex-hR1 blocks IGF-1 activation of the phosphorylation of IGF-1R, Akt and ERK1/2 in MCF-7 cells. The indicated concentrations of DNL construct Hex-hR1, control Hex-hRS7 or hR1 antibody were added to cells treated with 100 ng/ml IGF-1.
Figure 19:
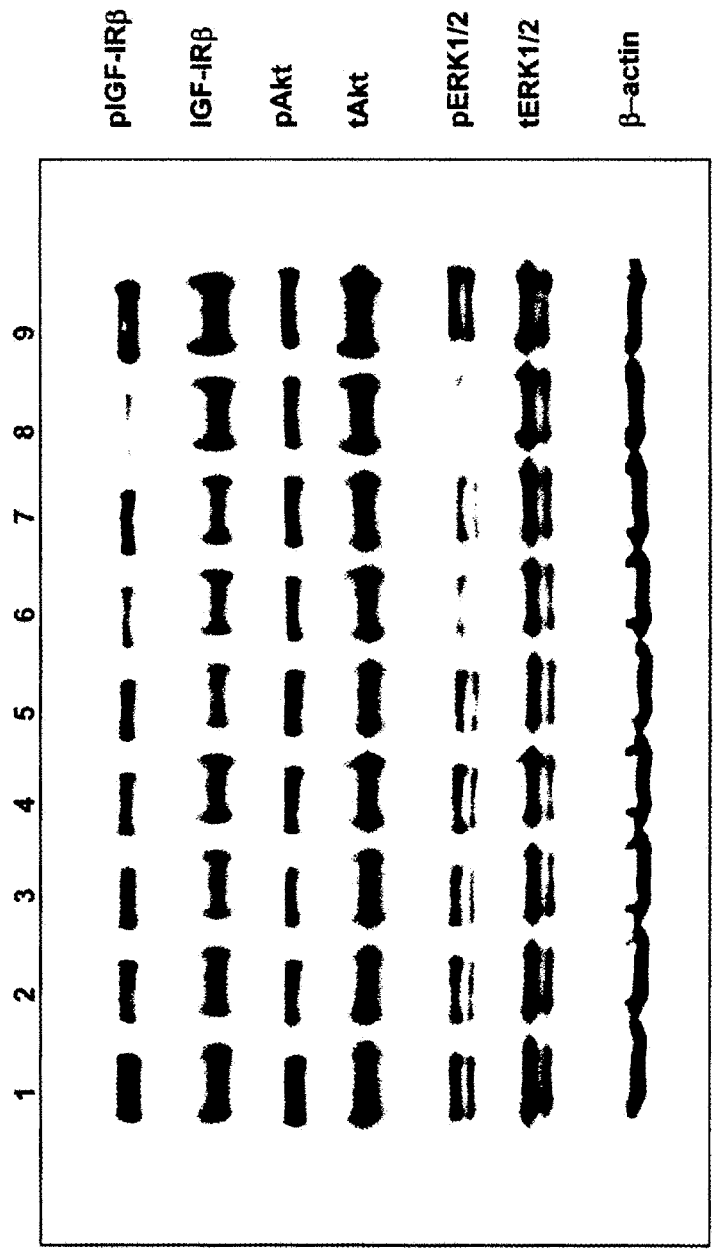
FIG. 19. Bispecific hexavalent constructs 1R-E1 or E1-1R inhibit phosphorylation of IGF-1R, Akt and ERK1/2 in MCF-7 cells stimulated with 100 ng/ml IGF-1.
Figure 20:
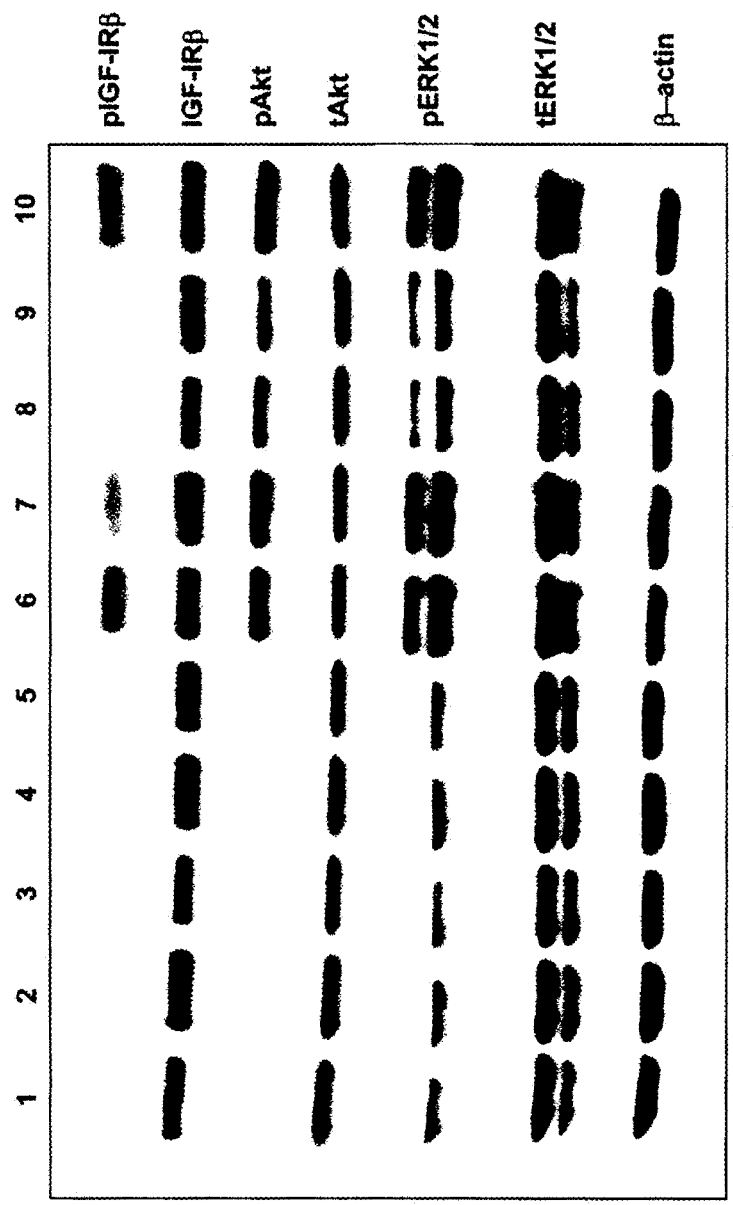
FIG. 20. Hex-hR1 inhibits phosphorylation of IGF-1R, Akt and ERK1/2 in DU-145 cells stimulated with 100 ng/ml IGF-1.

One major mechanism of anti-tumor actions induced by an anti-IGF-1R antibody, despite its being an agonist or antagonist, is to downregulate IGF-1R via endocytosis leading to subsequent degradation in endosomal vesicles. As shown in FIG. 14, efficient downregulation of IGF-1R in MCF-7 or HT-29 (colorectal cancer) was clearly demonstrated with hR1 at 100 nM as well as the two commercially available anti-IGF-1R antibodies (MAB391 and 24-60) serving as positive controls, but not with the anti-CD22 antibody, hLL2 (epratuzumab), which serves as a negative control. Further studies revealed that Hex-hR1 and 1R-E1 were capable of substantially reducing the level of IGF-1R at a concentration as low as 0.1 nM in MCF-7, DU-145, and LnCap (androgen-dependent prostate cancer), as shown in FIGS. 15A and B.

Example 10. Blocking the Signaling Pathways Induced by IGF-1

Although hR1 may not appear to prevent the binding of IGF-1 to bead-immobilized rhIGF-1R, it effectively blocks IGF-1 from activating various signaling molecules in three cell lines (MCF-7, DU-145, and ME-180), as collectively shown in FIGS. 16 to 20, by the reduced levels of phosphorylated IGF-1R (pIGF-1R), phosphorylated Akt (pAkt), and phosphorylated ERK1/2 (pERK1/2).

The described methods and compositions are of use for therapy of prostate cancer. The Examples disclosed above provide in vitro results, showing hR1, as well as its hexavalent derivatives made by DNL (Hex-hR1, 1R-E1, and E1-1R), can effectively downregulate IGF-1R and inhibit IGF-1 from stimulating the proliferation of androgen-independent DU-145 cells. The higher potency observed for the DNL constructs is presumably due to their enhanced avidity which may be further amplified for the bispecific counterparts because the increase in targetable antigens on the cell surface. As IGF-1R is expressed in various solid tumors and hematologic malignancies, the skilled artisan will realize that the claimed compositions and methods are also of use for therapy of other known IGF-1R expressing cancers, such as multiple myeloma and hepatoma. The combination of hR1 with other antibodies, such as anti-EGFR (C225) or anti-HER2 (Herceptin), is also of therapeutic use, as discussed above.

Example 11. Effects of Various hR1 Constructs in the MCF-7 Breast Cancer Xenograft Model Four-week old female athymic (nu/nu) mice are implanted with 60-day release pellets of 0.5 mg 17β-estradiol (Sachdev et al., Cancer Res. 2003; 63:627-35) and then injected with 10 million MCF-7 human breast cancer cells subcutaneously. When the tumors measure an average volume of 200 mm³, groups of 9 mice are randomized for intraperitoneal treatment with the following agents, twice per week for 4 consecutive weeks: (1) saline controls, same volume as test substances; (2) 400 µg hR1 IgG; (3) 800 µg hR1 IgG; (4) 400 µg hRS7 IgG (anti-EGP-1); (5) 800 µg hRS7 IgG; (6) 300 µg 1R-E1 hexavalent construct (hR1 IgG-hRS7-4 Fab's); (7) 600 µg 1R-E1; and (8) 800 µg 1R-E1. Tumor volumes are measured bidirectionally with a caliper twice weekly, beginning on the day of randomization and treatment; animal weights are also taken twice weekly. When mice become moribund or lose more than 20% of body weight, or when the tumors reach a size of 2.5 cm³, they are sacrificed, and tumors and normal tissues removed and preserved in formalin for histological and immunohistochemical analyses. By 60 days, the experiment is terminated, and shows continuous tumor growth of the controls, which are sacrificed as early as 5 weeks after therapy onset and then over the next 2 weeks. Evidence of inhibition of tumor growth is measured as 20% (relative to controls) for group 1, 35% for group 2, 54% for group 3, 11% for group 4, 26% for group 5, 32% for group 6, 51% for group 7, and 68% for group 8 at one week post therapy-end. These results indicate that the hR1 antibody doses are more inhibitory of tumor growth than those for the hRS7 (anti-EGP-1) antibody, but which also shows some antitumor activity. However, lower doses of the hexavalent bispecific antibody construct of hR1 and hRS7, at relatively lower doses, show equivalent to higher antitumor effects than the corresponding parental antibodies, suggesting greater potency for the bispecific antibody constructs made by DNL. No treatment-related toxicities, particularly more than a 20% body weight loss, is observed in the treatment groups.

When the same experiment is repeated with similar MCF-7-bearing mice, using an irrelevant isotype control antibody instead of saline, and including hexavalent hR1 and hexavalent hRS7 groups at doses of 400 µg and 800 µg i.p. each, twice weekly for 4 weeks, tumor growth inhibition is determined to range from 25-46% for hexavalent hR1 and 20-33% for hexavalent hRS7, suggesting that the hexavalent constructs are more potent than their bivalent parental counterparts.

Example 12. Effects of hR1 Constructs in BxPC3 Human Pancreatic and Colo205 Human Colonic Cancer Xenografts Tumor xenografts in 5-6-week-old female nu/nu athymic mice are injected s.c. with 2 million BxPC3 human pancreatic cancer or Colo205 human colonic cancer cells mixed in Matrigel, and allowed to grow to about 200 mm³ in size, and are randomized into groups of 11 each. Mice are treated by i.p. injection twice weekly of saline vehicle (control) or test substances at various doses for 4 consecutive weeks. Tumors are measured and the animals weighed and observed as per the prior Example. For each of the tumor models, the following doses are given, with the percentages of tumor growth-inhibition, GI (comparing mean volumes of treated vs. control groups before more than 20% of the control mice are sacrificed because of advanced tumor growth) in parentheses:

BxPC3 Human Pancreatic Cancer Model
  (1) 0.5 mg hR1 (39% GI)
  (2) 1.0 mg hR1 (68% GI)
  (3) 0.5 mg hPAM4 (15% GI)
  (4) 1.0 mg hPAM4 (24% GI)
  (5) 0.5 mg hRS7 (18% GI)
  (6) 1.0 mg hRS7 (29% GI)
  (7) 0.5 mg 1R-E1 (63% GI)
  (8) 0.5 mg 1R-1M (48% GI)
  (9) 1.0 mg hLL2 (anti-CD22 IgG) isotype control.

The results suggest a dose-dependent effect of hR1 in inhibiting growth of human pancreatic cancer xenografts, which appears superior to the hRS7 or hPAM4 antibodies, but the bispecific construct of hR1 and hRS7 (1R-E1) appears to show enhanced activity over the same doses of the parental antibodies given separately, and somewhat less enhanced efficacy for the bispecific antibody of hR1 and hPAM4 (1R-1M).

Colo205 Human Colonic Cancer Model
(1) 0.5 mg hR1 (46% GI)
(2) 1.0 mg hR1 (70% GI)
(3) 0.5 mg hMN-14 (14% GI)
(4) 1.0 mg hMN-14 (29% GI)
(5) 0.5 mg 14-1R (58% GI)
(6) 1.0 mg 14-1R (83% GI)
(7) 1.0 mg hLL2 control.

A dose-dependent growth-inhibition is observed for both anti-IGFR1 and anti-CEACAM5 (hMN-14) humanized antibodies, with the former being more potent in this model, but with the respective bispecific antibody constructs made by DNL showing improved efficacy compared to the equivalent doses of the bivalent parental antibodies.

Example 13. Effects of Effects of hR1 Constructs Alone and in Combination with Bortezomib in a Multiple Myeloma Xenografts Model CAG human myeloma cells are grown in cell culture to a density that allows 1 million cells to be harvested for transplantation to 6-8-week old female SCID mice obtained from Charles River Laboratories (Frederick, Md.). The mice are immunosuppressed by pretreatment with fludarabine and cyclophosphamide 3 days before intravenous injection of 5-10×16$^6$ myeloma cells as described in Stein et al. (Blood. 2004; 104:3705-11). Mice are examined daily for signs of distress or hind-leg paralysis, and weighed weekly. Paralysis of the hind legs or a weight loss of ≥20% is used as the survival endpoint, when the animals are euthanized. Groups of 8-10 mice are used. A dose-response study with hR1 given i.p. twice weekly for 4 weeks at 100, 300, 600, and 1,000 µg hR1 shows a significant (P<0.03) survival benefit compared to mice treated with the saline vehicle or with an unreactive isotype control antibody, which has a median survival of 40 days. The median survival of the hR1-treated mice ranged from 80 to 100 days, and shows a dose-response. The effects of combining bortezomib with hR1 are evaluated in the same myeloma model. Treatments are given as two i.p. doses/week for 3 weeks, initiated on day 5 after injection of the myeloma cells. Given as a single agent, 0.5 mg/kg bortezomib is well tolerated, with no body-weight loss. Median survival in untreated control mice is 33 days, for bortezomib alone 40 days (21.2% increase). Treatment with hR1 at 0.6 mg/mouse repeated twice weekly for 3 weeks increases the median survival time to 60 days. When bortezomib and hR1 treatments are combined, the median survival time is increased further to 79 days for 0.5 mg bortezomib+0.6 mg hR1, which is significant (P=0.04). Therefore, an agent that is active in treating myeloma shows enhanced activity when combined with this anti-IGFR1 antibody.

Example 14. Effects of Combination Therapy of $^{90}$Y-hPAM4 Radioimmunotherapy with Gemcitabine and Anti-IGFR1 Antibody (hR1) Immunotherapy in Pancreatic Cancer YS is a 61-year-old male diagnosed 2 months earlier with stage III/IV, metastatic, inoperable pancreatic adenocarcinoma, having a 6 cm diameter pancreatic lesion at the head of the pancreas and two metastases to the liver of about 3 and 4 cm in diameter. The patient has an elevated CA19.9 titer of 7,200, but with most other laboratory values either borderline or within the normal range. He is active, but is easily fatigued, has occasional abdominal pains requiring minimal medication, and has lost about 10 kg since diagnosis. He opts for an investigational treatment involving a 4-week therapy consisting of gemcitabine (GEMZAR®) given i.v. once weekly at 200 mg/m$^2$, $^{111}$In-DOTA-hPAM4 antibody (labeled as described in Sharkey et al. [J Nucl Med. 2003 December; 44(12):2000-18] given by infusion also on week 1 to assess antibody localization by immunoscintigraphy, followed by the next 3 consecutive weekly infusions of 12 mCi/m$^2$ of $^{90}$Y-DOTA-hPAM4 (labeled as per Sharkey et al., ibid). On days 1, 7, 14, and 21, doses of hR1 of 10 mg/kg, 16 mg/kg, 16 mg/kg, and 20 mg/kg are given by i.v. infusion. The patient experiences some grade 1-2 nausea, back pain, hypotension, anorexia and fatigue following each infusion, reducing severity with each one, which is mild because of being premedicated with 50 mg hydrocortisone, acetaminophen, and diphenylhydramine to control infusion reactions. At 4 weeks post therapy, the patient undergoes FDG-PET and CT scanning to compare the metabolism and size of the pancreatic cancer lesions before and after therapy, and blood is taken to measure the CA19-9 tumor biomarker titer. The SUV of the primary cancer changes to 3.3 from 8.9, and the two metastatic lesions in the liver shows a larger drop from 6.1 and 5.3 to 5.3 and 3.5, respectively. CT measurements indicate a 1-cm reduction of the primary tumor, and an approximately 33% reduction in the two liver metastases. At this time, the CA19.9 titer measures 930, representing a major drop from 7,200. Follow-up studies 4 weeks later confirm continued reductions of the SUV values and either stabilization or a slight reduction of the sizes of the tumors, as measured by CT. Three months later, since the patient has stable disease, the therapy is repeated, is tolerated well, and again shows stable disease, with no increase of the CA19.9 titer at the next, 4-week, follow-up. It is concluded that this combination therapy has, at the minimum, stabilized the disease, decreased the tumors' metabolic activity, and markedly reduced the pancreatic cancer blood biomarker, CA19-9. The patient has been normally active during this period, has no fatigue or pain, and has gained back 4 kg body weight. There are no hematological or other laboratory abnormalities.

Example 15. Combination FOLFIRI Therapy of Metastatic Colorectal Cancer with hR1

RS is a 71-year-old woman with no prior serious illness and presenting with metastatic colonic cancer post resection of a sigmoid colon B3 adenocarcinoma 6 months earlier. She refuses post-operative radiation or chemotherapy. Her blood CEA titer is elevated at 11 ng/ml. FDG-PET/CT imaging shows no recurrence at the primary resection, but 3 discrete lesions (2-4 cm in diameter) in the right liver lobe and 1 larger lesion (6 cm) in the left liver lobe. Not being a candidate for salvage liver resection, she undergoes a combination of FOLFIRI combined with hR1 therapy. On day 1, 180 mg/m$^2$ irinotecan is given in 500 ml normal saline as a 2-h infusion, and on days 1 and 2, 400 mg/m$^2$ of folinic acid is given as an i.v. bolus over 2 hours, followed by fluorouracil (2,400 mg/m$^2$) as a continuous 46-h infusion, every 2 weeks. Anti-IGF-1R antibody, hR1, is given at 10 mg/kg as a slow infusion weekly×2 weeks, including premedication as in the prior patient Example. Eight cycles of this combination therapy are given. Six weeks after completion of therapy, FDG-PET/CT scans indicate a 60% reduction of size and also an SUV reduction of the left lobe metastasis, while 2 of 3 right lobe metastases appear about 1 cm in diameter while the third is unchanged. SUV values for 2 of the 3 are reduced to almost 0, and the third is 3.2. No change in circulating CEA is noted. After another 6 weeks, 2 of 3

Example 16. Therapy of a Patient with Hepatocelluar Carcinoma with Radiolabeled hR1 Monoclonal Antibody A 57-year-old man presenting with jaundice, malaise, loss of weight, and general weakness, is diagnosed with an inoperable hepatocellular carcinoma that appears by computed tomography to extend about 6 cm in diameter in the right lobe of the liver, and to also appear as a single 3-cm lesion in the left lobe. The right lobe lesion is confirmed by biopsy to be hepatocellular carcinoma.

The patient is given two cycles of hR1 monoclonal antibody conjugated by DOTA with $^{90}$Y, as described in Sharkey et al. (J Nucl Med. 2003 December; 44(12):2000-18), so that an infusion is administered for each therapy dose of 25 mCi (100 mg antibody protein). The first therapy is given in an outpatient setting, and is repeated 6 weeks later. Prior to each therapy, a diagnostic dose of $^{111}$In conjugated by DOTA to the antibody (labeling also described in Sharkey et al, 2003, ibid), is also injected in order to demonstrate tumor targeting and to estimate the radiation dose delivered to the tumor and to other normal tissues, such as liver, kidney and bone marrow, so that the therapeutic dose with $^{90}$Y, given a week later, can be adjusted so as not to induce normal tissue/organ toxicity beyond what is considered tolerable (e.g., 2000 cGy to kidneys). The patient is then monitored for response by repeated computer tomography (CT) scans every 4-8 weeks post therapy, as well as by serum AFP, bilirubin, transaminase, and LDH levels.

Eight weeks after the second therapeutic administration of the $^{90}$Y-labeled antibody, his serum levels of bilirubin, transaminases, and LDH decrease to about 20% above normal, and his serum AFP titer is measured at 60 ng/mL, which also constitutes an improvement. CT measurements of his liver disease show an almost complete disappearance of the left lobe lesion and a 40% reduction of the larger mass in the right lobe. The patient then becomes a candidate for surgical resection of his right lobe, since it is considered that the remaining small lesion in the left lobe is not cancer, but scar tissue.

Example 17. Therapy of a Patient with $^{90}$Y-Labeled hR1 Antibody Combined with Naked hR1 Antibody A 62-year-old man has a history of Dukes' C rectal carcinoma that is resected 3 years earlier, followed by radiation therapy and 5-fluorouracil/folinic acid chemotherapy. The patient begins to show a rise in his plasma CEA titer, reaching a level of 30 ng/mL. The patient undergoes various diagnostic procedures because of a suspected recurrence. It is found, by computed tomography, that there are two metastases present in his liver, one being 3 cm in diameter in his right lobe, and the other being somewhat smaller in the left lobe, close to the interlobe ligament. The patient is first given 3 weekly infusions of 10 mg/kg hR1 antibody, followed by a dose of 25 mCi $^{90}$Y conjugated to hR1 antibody, given at a protein dose of 50 mg by intravenous infusion over a period of 2 hours, on the third week of naked hR1 therapy, prior to the third hR1 injection. This therapy is repeated two months later. The patient shows a drop of his white blood cells and platelets, measured 2-4 weeks after the last therapy infusion, but recuperates at the 8-week post-therapy evaluation. The computed tomography findings at 3 months post-therapy reveal 40% shrinkage of the major tumor metastasis of the right liver lobe, and a lesser reduction in the left-lobe tumor.

At the 6-month follow-up, his tumor lesions have been reduced, in two-diameter CT-measurements, by about 70 percent, his plasma CEA is at 8 ng/mL, and his general condition is improved, with no apparent toxicity or adverse events related to the therapy.

Example 18. Treatment of a Breast Cancer Patient with Y-90 hR1 MAb and with Naked hR1 MAb A 56-year-old woman with a history of recurrent adencarcinoma of the breast presents with cervical lymph node and left lung metastases. She relapses twice after chemotherapy and hormonal therapies. She is then given three therapeutic injections, each one week apart, of $^{90}$Y-conjugated hR1 MAb i.v., at a dose of 15 mCi $^{90}$Y each in a protein dose of antibody of 100 mg. Four weeks after therapy, her white blood cell and platelet counts decrease by approximately 50%, but recuperate by 9 weeks post-therapy. At a restaging 12 weeks post-therapy, an approximately 30% decrease in pulmonary and nodal metastases is measured by computed tomography. Thereafter, she receives 4 weekly infusions, over 4 hours each, of naked hR1 antibody, which is tolerated well, except for some transient rigors and chills, and without any adverse effects on her blood counts or blood chemistries. The naked antibody dose for each infusion is 12 mg/kg. Approximately 8 weeks later, restaging by computed tomography indicates an additional decrease in measurable lesions by about 20 percent. At the followup examination 3 months later, her disease appears to be stable (i.e., no evidence of additional or progressive growth).

All of the COMPOSITIONS and METHODS disclosed and claimed herein can be made and used without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated anti-IGF-1R (insulin-like growth factor type 1 receptor) antibody or antigen-binding fragment thereof comprising the heavy chain variable region complementarity determining region (CDR) sequences CDR1 (DYYMY, SEQ ID NO:1), CDR2 (YITNYGGSTYYPDT-VKG, SEQ ID NO:2) and CDR3 (QSNYDYDGWFAY, SEQ ID NO:3) and the light chain variable region CDR sequences CDR1 (KASQEVGTAVA, SEQ ID NO:4), CDR2 (WASTRHT, SEQ ID NO:5) and CDR3 (QQYSNYPLT, SEQ ID NO:6).

2. The anti-IGF-1R antibody or fragment thereof of claim 1, wherein said anti-IGF-1R antibody is a humanized R1 (hR1) antibody comprising the amino acid sequences of SEQ ID NO:9 (hR1 VH) and SEQ ID NO:10 (hR1 VK).

3. The anti-IGF-1R antibody or fragment thereof of claim 1, wherein said antibody exhibits at least one functional characteristic selected from the group consisting of: (i) binds to human IGF-1R and does not bind to human insulin receptor (IR); (ii) is not an agonist of IGF-1R; (iii) does not block binding of IGF-1 or IGF-2 to an isolated IGF-1R; and (iv) neutralizes the activation of IGF-1R by IGF-1 in intact cells.

4. The anti-IGF-1R antibody or fragment thereof of claim 1, wherein said anti-IGF-1R antibody does not compete for binding to isolated IGF-1R with the anti-IGF-1R antibodies 24-31, 24-57, 17-69, 1-2, 1H7, 2C8 or 3B7.

5. The anti-IGF-1R antibody or fragment thereof of claim 1, wherein said anti-IGF-1R antibody does not bind to amino acid residues 1-150, 223-274, 184-283, 283-440, 440-514, 514-586 or 1323-1337 of isolated human IGF-1R.

6. The anti-IGF-1R antibody or fragment thereof of claim 1, wherein said anti-IGF-1R antibody binds to an epitope of IGF-1R comprising the first half of the cysteine-rich domain of IGF-1R, between amino acid residues 151 and 222 of human IGF-1R.

7. The anti-IGF-1R antibody or fragment thereof of claim 1, wherein said antibody or fragment is a naked antibody or fragment or is conjugated to at least one diagnostic or therapeutic agent.

8. The anti-IGF-1R antibody or fragment thereof of claim 7, wherein said therapeutic agent is selected from the group consisting of a radionuclide, an immunomodulator, an anti-angiogenic agent, a cytokine, a chemokine, a growth factor, a hormone, a drug, a prodrug, an enzyme, an oligonucleotide, a pro-apoptotic agent, an interference RNA, a photoactive therapeutic agent, a cytotoxic agent, a chemotherapeutic agent, an EGFR inhibitor and a toxin.

9. The anti-IGF-1R antibody or fragment thereof of claim 7, wherein said therapeutic agent is selected from the group consisting of 5-fluorouracil, aplidin, azaribine, anastrozole, anthracyclines, bendamustine, bleomycin, bortezomib, bryostatin-1, busulfan, calicheamycin, camptothecin, carboplatin, 10-hydroxycamptothecin, carmustine, celecoxib, chlorambucil, cisplatinum, Cox-2 inhibitors, irinotecan (CPT-11), SN-38, carboplatin, cladribine, camptothecans, cyclophosphamide, cytarabine, dacarbazine, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, estramustine, epidophyllotoxin, estrogen receptor binding agents, etoposide (VP16), etoposide glucuronide, etoposide phosphate, floxuridine (FUdR), 3',5'-O-dioleoyl-FudR (FUdR-dO), fludarabine, flutamide, farnesyl-protein transferase inhibitors, gemcitabine, hydroxyurea, idarubicin, ifosfamide, L-asparaginase, lenolidamide, leucovorin, lomustine, mechlorethamine, melphalan, mercaptopurine, 6-mercaptopurine, methotrexate, mitoxantrone, mithramycin, mitomycin, mitotane, navelbine, nitrosurea, plicomycin, procarbazine, paclitaxel, pentostatin, PSI-341, raloxifene, semustine, streptozocin, tamoxifen, temazolomide, DTIC, transplatinum, thalidomide, thioguanine, thiotepa, teniposide, topotecan, uracil mustard, vinorelbine, vinblastine, vincristine and vinca alkaloids.

10. The anti-IGF-1R antibody or fragment thereof of claim 8, wherein the toxin is selected from the group consisting of ribonuclease (RNase), ranpirnase, DNase I, *Staphylococcal* enterotoxin-A, pokeweed antiviral protein, gelonin, diphtheria toxin, *Pseudomonas* exotoxin, and *Pseudomonas* endotoxin.

11. The anti-IGF-1R antibody or fragment thereof of claim 8, wherein the immunomodulator is selected from the group consisting of a cytokine, a stem cell growth factor, a lymphotoxin, an hematopoietic factor, a colony stimulating factor (CSF), an interferon (IFN), erythropoietin, and thrombopoietin.

12. The anti-IGF-1R antibody or fragment thereof of claim 11, wherein the cytokine is selected from the group consisting of human growth hormone, N-methionyl human growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, tumor necrosis factor-α, TNF-β, mullerian-inhibiting substance, mouse gonadotropin-associated peptide, inhibin, activin, vascular endothelial growth factor, integrin, thrombopoietin (TPO), NGF-β, platelet-growth factor, TGF-α, TGF-β, insulin-like growth factor-I, insulin-like growth factor-II, erythropoietin (EPO), interferon-α, interferon-β, interferon-γ, macrophage-CSF, G-CSF, GM-CSF, IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, kit-ligand, angiostatin, thrombospondin, endostatin, tumor necrosis factor and lymphotoxin.

13. The anti-IGF-1R antibody or fragment thereof of claim 8, wherein the chemokine is selected from the group consisting of RANTES, MCAF, MIP1-alpha, MIP1-Beta and IP-10.

14. The anti-IGF-1R antibody or fragment thereof of claim 8, wherein the radionuclide is selected from the group consisting of $^{111}$In, $^{177}$Lu, $^{212}$Bi, $^{213}$Bi, $^{211}$At, $^{62}$Cu, $^{67}$Cb, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th and $^{211}$Pb.

15. The anti-IGF-1R antibody or fragment thereof of claim 7, wherein said diagnostic agent is selected from the group consisting of a radioisotope, a dye, a radiological contrast agent, an ultrasound contrast agent, a fluorescent label, a chemiluminescent label, an enzyme, an enhancing agent and a paramagnetic ion.

16. The anti-IGF-1R antibody of claim 1, wherein said antibody comprises constant region sequences of a human IgG1 or IgG4 antibody.

17. The anti-IGF-1R antibody or fragment thereof of claim 1, wherein said anti-IGF-1R antibody is a chimeric antibody, a humanized antibody or a human antibody.

18. The anti-IGF-1R antibody or fragment thereof of claim 1, wherein said anti-IGF-1R antibody is a humanized antibody comprising framework and constant region sequences from a human antibody.

19. The anti-IGF-1R antibody or fragment thereof of claim 18, wherein the variable region sequences of said humanized anti-IGF-1R antibody have at least 90%, at least 95%, at least 98%, at least 99% or at least 99.5% sequence homology to SEQ ID NO:9 and SEQ ID NO:10.

20. The anti-IGF-1R antibody or fragment thereof of claim 1, wherein said anti-IGF-1R antibody is a chimeric R1 (cR1) antibody comprising the amino acid sequences of SEQ ID NO:7 (R1 VH) and SEQ ID NO:8 (R1 VK) attached to human antibody constant region sequences.

* * * * *

SEQUENCE LISTING

<160> NUMBER OF SEQ ID NOS: 56

<210> SEQ ID NO 1
<211> LENGTH: 5

-continued

```
<212> TYPE: PRT
<213> ORGANISM: Mus musculus

<400> SEQUENCE: 1

Asp Tyr Tyr Met Tyr
1               5

<210> SEQ ID NO 2
<211> LENGTH: 17
<212> TYPE: PRT
<213> ORGANISM: Mus musculus

<400> SEQUENCE: 2

Tyr Ile Thr Asn Tyr Gly Gly Ser Thr Tyr Tyr Pro Asp Thr Val Lys
1               5                   10                  15

Gly

<210> SEQ ID NO 3
<211> LENGTH: 12
<212> TYPE: PRT
<213> ORGANISM: Mus musculus

<400> SEQUENCE: 3

Gln Ser Asn Tyr Asp Tyr Asp Gly Trp Phe Ala Tyr
1               5                   10

<210> SEQ ID NO 4
<211> LENGTH: 11
<212> TYPE: PRT
<213> ORGANISM: Mus musculus

<400> SEQUENCE: 4

Lys Ala Ser Gln Glu Val Gly Thr Ala Val Ala
1               5                   10

<210> SEQ ID NO 5
<211> LENGTH: 7
<212> TYPE: PRT
<213> ORGANISM: Mus musculus

<400> SEQUENCE: 5

Trp Ala Ser Thr Arg His Thr
1               5

<210> SEQ ID NO 6
<211> LENGTH: 9
<212> TYPE: PRT
<213> ORGANISM: Mus musculus

<400> SEQUENCE: 6

Gln Gln Tyr Ser Asn Tyr Pro Leu Thr
1               5

<210> SEQ ID NO 7
<211> LENGTH: 121
<212> TYPE: PRT
<213> ORGANISM: Mus musculus

<400> SEQUENCE: 7

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30
```

```
Tyr Met Tyr Trp Val Arg Gln Thr Pro Glu Lys Arg Leu Glu Trp Val
            35                  40                  45

Ala Tyr Ile Thr Asn Tyr Gly Gly Ser Thr Tyr Tyr Pro Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Arg Leu Arg Ser Glu Asp Thr Ala Met Tyr Phe Cys
                 85                  90                  95

Ala Arg Gln Ser Asn Tyr Asp Tyr Asp Gly Trp Phe Ala Tyr Trp Gly
                100                 105                 110

Gln Gly Thr Thr Val Thr Val Ser Ser
            115                 120
```

<210> SEQ ID NO 8
<211> LENGTH: 108
<212> TYPE: PRT
<213> ORGANISM: Mus musculus

<400> SEQUENCE: 8

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Glu Val Gly Thr Ala
                 20                  25                  30

Val Ala Trp Tyr Gln Gln Lys Pro Gly Gln Ser Pro Lys Leu Leu Ile
             35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Gln Gln Tyr Ser Asn Tyr Pro Leu
                 85                  90                  95

Thr Phe Gly Ala Gly Ala Lys Leu Glu Leu Lys Arg
            100                 105
```

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Val Gln Leu Gln Glu Ser Gly Gly Gly Val Val Gln Pro Gly Arg
 1               5                  10                  15

Ser Leu Arg Leu Ser Cys Ser Ala Ser Gly Phe Thr Phe Ser Asp Tyr
                 20                  25                  30

Tyr Met Tyr Trp Val Arg Gln Ala Pro Gly Lys Gly Leu Glu Trp Val
             35                  40                  45

Ala Tyr Ile Thr Asn Tyr Gly Gly Ser Thr Tyr Tyr Pro Asp Thr Val
 50                  55                  60

Lys Gly Arg Phe Thr Ile Ser Arg Asp Asn Ala Lys Asn Thr Leu Phe
 65                  70                  75                  80

Leu Gln Met Asp Ser Leu Arg Pro Glu Asp Thr Gly Val Tyr Phe Cys
                 85                  90                  95

Ala Arg Gln Ser Asn Tyr Asp Tyr Asp Gly Trp Phe Ala Tyr Trp Gly
                100                 105                 110
```

```
Gln Gly Thr Pro Val Thr Val Ser Ser
        115                 120
```

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Glu Val Gly Thr Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln Tyr Ser Asn Tyr Pro Leu
                85                  90                  95

Thr Phe Gly Gln Gly Thr Lys Val Glu Ile Lys Arg
            100                 105
```

<210> SEQ ID NO 11
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccgcggtcac atggcaccac ctctcttgca gcttccacca agggccc                47

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccggccgtcg cactcattta cccagagaca ggg                               33

<210> SEQ ID NO 13
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gagtccaaat atggtccccc atgcccaccg tgcccaggta agccaaccca gg          52

<210> SEQ ID NO 14
<211> LENGTH: 56
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 14
cctgggttgg cttacctggg cacggtgggc atggggacc atatttggac tctgca          56

<210> SEQ ID NO 15
<211> LENGTH: 44
<212> TYPE: PRT
<213> ORGANISM: Homo sapiens

<400> SEQUENCE: 15

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Ile Glu Tyr Leu Ala Lys Gln Ile Val Asp Asn Ala Ile Gln Gln
1               5                   10                  15

Ala

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Gly Gln Ile Glu Tyr Leu Ala Lys Gln Ile Val Asp Asn Ala Ile
1               5                   10                  15

Gln Gln Ala Gly Cys
            20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaacctcgcg gacagttaag                                                   20

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatcctccg ccgccgcagc tcttaggttt cttgtccacc ttggtgttgc tgg             53

<210> SEQ ID NO 21
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 22
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggatccggag gtggcgggtc tggcggaggt ggcagccaga tcgagtacct ggccaagcag      60
atcgtggaca cgccatcca gcaggcctga cggccg                                 96

<210> SEQ ID NO 23
<211> LENGTH: 96
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cggccgtcag gcctgctgga tggcgttgtc cacgatctgc ttggccaggt actcgatctg      60
gctgccacct ccgccagacc cgccacctcc ggatcc                                96
```

```
<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatccggag gtggcgggtc tggcggaggt                                        30

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggccgtcag gcctgctgga tg                                                22

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Gly Gly Gly Ser Gly Gly Gly Cys Gly
1               5                   10

<210> SEQ ID NO 27
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gatccggagg tggcgggtct ggcggaggtt gcggccacat ccagatcccg ccggggctca      60
cggagctgct gca                                                         73

<210> SEQ ID NO 28
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcagctccgt gagccccggc gggatctgga tgtggccgca acctccgcca gacccgccac      60
ctccg                                                                  65

<210> SEQ ID NO 29
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
```

```
gatccggagg tggcgggtct ggcggatgtg gccagatcga gtacctggcc aagcagatcg    60
tggacaacgc catccagcag gccggctgct gaa                                 93
```

<210> SEQ ID NO 30
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
ttcagcagcc ggcctgctgg atggcgttgt ccacgatctg cttggccagg tactcgatct    60
ggccacatcc gccagacccg ccacctccg                                      89
```

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ser Gly Gly Gly Gly Ser Gly Gly
1               5

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
agatctggcg cacctgaact cctg                                           24
```

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
gaattcggat cctttacccg gagacaggga gag                                 33
```

<210> SEQ ID NO 34
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

```
gtggcgggtc tggcggaggt ggcagccaca tccagatccc gccggggctc acggagctgc    60
tgcagggcta cacggtggag gtgctgcgac ag                                  92
```

<210> SEQ ID NO 35
<211> LENGTH: 92
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 35
gcgcgagctt ctctcaggcg ggtgaagtac tccactgcga attcgacgag gtcaggcggc    60
tgctgtcgca gcacctccac cgtgtagccc tg                                  92

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggatccggag gtggcgggtc tggcggaggt                                     30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cggccgtcaa gcgcgagctt ctctcaggcg                                     30

<210> SEQ ID NO 38
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Val Ala Lys Gln Ile Val Asp Tyr Ala Ile His Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 40

Gln Ile Glu Tyr Lys Ala Lys Gln Ile Val Asp His Ala Ile His Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr His Ala Lys Gln Ile Val Asp His Ala Ile His Gln
1               5                   10                  15

Ala

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Val Ala Lys Gln Ile Val Asp His Ala Ile His Gln
1               5                   10                  15

Ala

<210> SEQ ID NO 43
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 44
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Glu Gln Tyr Ala Asn Gln Leu Ala Asp Gln Ile Ile Lys Glu Ala
1               5                   10                  15

Thr Glu

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 45

Phe Glu Glu Leu Ala Trp Lys Ile Ala Lys Met Ile Trp Ser Asp Val
1               5                   10                  15

Phe Gln Gln Cys
            20

<210> SEQ ID NO 46
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 47
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 48
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Cys Gly Phe Glu Glu Leu Ala Trp Lys Ile Ala Lys Met Ile Trp Ser
1               5                   10                  15

Asp Val Phe Gln Gln Gly Cys
            20

-continued

```
<210> SEQ ID NO 50
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
                20                  25                  30

Pro Met Ala Phe Leu Arg Glu Tyr Phe Glu Arg Leu Glu Lys Glu Glu
            35                  40                  45

Ala Lys
    50

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His His His His His His
1               5

<210> SEQ ID NO 52
<211> LENGTH: 15
<212> TYPE: PRT
<213> ORGANISM: Mus musculus

<400> SEQUENCE: 52

Glu Val Lys Leu Val Glu Ser Gly Gly Gly Leu Val Gln Pro Gly
1               5                   10                  15

<210> SEQ ID NO 53
<211> LENGTH: 15
<212> TYPE: PRT
<213> ORGANISM: Mus musculus

<400> SEQUENCE: 53

Asp Ile Val Met Thr Gln Ser His Lys Phe Met Ser Thr Ser Val
1               5                   10                  15

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Gly Gly Gly Ser
1               5

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 55

Gly Gly Gly Gly Ser Gly Gly Gly Ser
1               5                   10

<210> SEQ ID NO 56
<211> LENGTH: 1367
<212> TYPE: PRT
<213> ORGANISM: Homo sapiens

<400> SEQUENCE: 56

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
            35                  40                  45

Leu Glu Asn Cys Thr Val Ile Glu Gly Tyr Leu His Ile Leu Leu Ile
        50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
        275                 280                 285

Glu Ser Ser Asp Ser Glu Gly Phe Val Ile His Asp Gly Glu Cys Met
    290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
                325                 330                 335

Lys Thr Lys Thr Ile Asp Ser Val Thr Ser Ala Gln Met Leu Gln Gly

-continued

```
                340                 345                 350
Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
        435                 440                 445

Ala Phe Asn Pro Lys Leu Cys Val Ser Glu Ile Tyr Arg Met Glu Glu
        450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
        610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765
```

```
Glu Glu Leu Glu Thr Glu Tyr Pro Phe Phe Glu Ser Arg Val Asp Asn
    770                 775                 780
Lys Glu Arg Pro Val Ile Ser Asn Leu Arg Pro Phe Thr Leu Tyr Arg
785                 790                 795                 800
Ile Asp Ile His Ser Cys Asn His Glu Ala Glu Lys Leu Gly Cys Ser
                    805                 810                 815
Ala Ser Asn Phe Val Phe Ala Arg Thr Met Pro Ala Glu Gly Ala Asp
                820                 825                 830
Asp Ile Pro Gly Pro Val Thr Trp Glu Pro Arg Pro Glu Asn Ser Ile
            835                 840                 845
Phe Leu Lys Trp Pro Glu Pro Glu Asn Pro Asn Gly Leu Ile Leu Met
850                 855                 860
Tyr Glu Ile Lys Tyr Gly Ser Gln Val Glu Asp Gln Arg Glu Cys Val
865                 870                 875                 880
Ser Arg Gln Glu Tyr Arg Lys Tyr Gly Gly Ala Lys Leu Asn Arg Leu
                885                 890                 895
Asn Pro Gly Asn Tyr Thr Ala Arg Ile Gln Ala Thr Ser Leu Ser Gly
            900                 905                 910
Asn Gly Ser Trp Thr Asp Pro Val Phe Phe Tyr Val Gln Ala Lys Thr
        915                 920                 925
Gly Tyr Glu Asn Phe Ile His Leu Ile Ile Ala Leu Pro Val Ala Val
    930                 935                 940
Leu Leu Ile Val Gly Gly Leu Val Ile Met Leu Tyr Val Phe His Arg
945                 950                 955                 960
Lys Arg Asn Asn Ser Arg Leu Gly Asn Gly Val Leu Tyr Ala Ser Val
                965                 970                 975
Asn Pro Glu Tyr Phe Ser Ala Ala Asp Val Tyr Val Pro Asp Glu Trp
            980                 985                 990
Glu Val Ala Arg Glu Lys Ile Thr Met Ser Arg Glu Leu Gly Gln Gly
        995                 1000                1005
Ser Phe Gly Met Val Tyr Glu Gly Val Ala Lys Gly Val Val Lys
    1010                1015                1020
Asp Glu Pro Glu Thr Arg Val Ala Ile Lys Thr Val Asn Glu Ala
    1025                1030                1035
Ala Ser Met Arg Glu Arg Ile Glu Phe Leu Asn Glu Ala Ser Val
    1040                1045                1050
Met Lys Glu Phe Asn Cys His His Val Val Arg Leu Leu Gly Val
    1055                1060                1065
Val Ser Gln Gly Gln Pro Thr Leu Val Ile Met Glu Leu Met Thr
    1070                1075                1080
Arg Gly Asp Leu Lys Ser Tyr Leu Arg Ser Leu Arg Pro Glu Met
    1085                1090                1095
Glu Asn Asn Pro Val Leu Ala Pro Pro Ser Leu Ser Lys Met Ile
    1100                1105                1110
Gln Met Ala Gly Glu Ile Ala Asp Gly Met Ala Tyr Leu Asn Ala
    1115                1120                1125
Asn Lys Phe Val His Arg Asp Leu Ala Ala Arg Asn Cys Met Val
    1130                1135                1140
Ala Glu Asp Phe Thr Val Lys Ile Gly Asp Phe Gly Met Thr Arg
    1145                1150                1155
Asp Ile Tyr Glu Thr Asp Tyr Tyr Arg Lys Gly Gly Lys Gly Leu
    1160                1165                1170
```

-continued

```
Leu Pro Val Arg Trp Met Ser Pro Glu Ser Leu Lys Asp Gly Val
    1175            1180            1185

Phe Thr Thr Tyr Ser Asp Val Trp Ser Phe Gly Val Val Leu Trp
    1190            1195            1200

Glu Ile Ala Thr Leu Ala Glu Gln Pro Tyr Gln Gly Leu Ser Asn
    1205            1210            1215

Glu Gln Val Leu Arg Phe Val Met Glu Gly Gly Leu Leu Asp Lys
    1220            1225            1230

Pro Asp Asn Cys Pro Asp Met Leu Phe Glu Leu Met Arg Met Cys
    1235            1240            1245

Trp Gln Tyr Asn Pro Lys Met Arg Pro Ser Phe Leu Glu Ile Ile
    1250            1255            1260

Ser Ser Ile Lys Glu Glu Met Glu Pro Gly Phe Arg Glu Val Ser
    1265            1270            1275

Phe Tyr Tyr Ser Glu Glu Asn Lys Leu Pro Glu Pro Glu Glu Leu
    1280            1285            1290

Asp Leu Glu Pro Glu Asn Met Glu Ser Val Pro Leu Asp Pro Ser
    1295            1300            1305

Ala Ser Ser Ser Ser Leu Pro Leu Pro Asp Arg His Ser Gly His
    1310            1315            1320

Lys Ala Glu Asn Gly Pro Gly Pro Gly Val Leu Val Leu Arg Ala
    1325            1330            1335

Ser Phe Asp Glu Arg Gln Pro Tyr Ala His Met Asn Gly Gly Arg
    1340            1345            1350

Lys Asn Glu Arg Ala Leu Pro Leu Pro Gln Ser Ser Thr Cys
    1355            1360            1365
```